(12) United States Patent
Frey et al.

(10) Patent No.: US 9,375,349 B2
(45) Date of Patent: Jun. 28, 2016

(54) SYSTEM AND METHOD FOR PROVIDING LASER SHOT PATTERNS TO THE LENS OF AN EYE

(75) Inventors: Rudolph W. Frey, Maitland, FL (US); Steven E. Bott, Oviedo, FL (US); Gary P. Gray, Orlando, FL (US)

(73) Assignee: LENSAR, LLC, Orlando, FL (US)

( * ) Notice: Subject to any disclaimer, the term of this patent is extended or adjusted under 35 U.S.C. 154(b) by 637 days.

(21) Appl. No.: 12/842,870

(22) Filed: Jul. 23, 2010

(65) Prior Publication Data

US 2010/0292678 A1 Nov. 18, 2010

Related U.S. Application Data

(63) Continuation-in-part of application No. 12/217,285, filed on Jul. 2, 2008, which is a continuation-in-part of application No. PCT/US2007/001353, filed on Jan. 19, 2007, and a continuation-in-part of application No.
(Continued)

(51) Int. Cl.
*A61F 9/008* (2006.01)

(52) U.S. Cl.
CPC .............. *A61F 9/008* (2013.01); *A61F 9/00825* (2013.01); *A61F 9/00838* (2013.01); *A61F 2009/0087* (2013.01); *A61F 2009/00897* (2013.01)

(58) Field of Classification Search
CPC ................................ A61F 9/008–9/009; A61F 2009/008–2009/00897
USPC .......................................... 606/4–6; 128/898
See application file for complete search history.

(56) References Cited

U.S. PATENT DOCUMENTS

| | | |
|---|---|---|
| 3,074,407 A | 1/1963 | Moon et al. |
| 3,971,382 A | 7/1976 | Krasnov |
| 3,982,541 A | 9/1976 | L'Esperance, Jr. |
| 4,024,852 A | 5/1977 | L'Esperance et al. |
| 4,263,893 A | 4/1981 | Pavlak et al. |
| 4,306,546 A | 12/1981 | Heine et al. |
| 4,309,998 A | 1/1982 | Aron nee Rosa et al. |
| 4,334,736 A | 6/1982 | Herbert |
| 4,381,007 A | 4/1983 | Doss |
| 4,394,144 A | 7/1983 | Aoki |

(Continued)

FOREIGN PATENT DOCUMENTS

| | | |
|---|---|---|
| CA | 2553963 A1 | 8/2005 |
| CA | 2680072 A1 | 9/2008 |

(Continued)

OTHER PUBLICATIONS

U.S. Appl. No. 11/337,127, filed Jan. 20, 2006, Frey et al.
(Continued)

*Primary Examiner* — Lynsey Crandall
*Assistant Examiner* — Nathan J Jenness
(74) *Attorney, Agent, or Firm* — Steptoe & Johnson LLP

(57) ABSTRACT

There is provided a system, apparatus and methods for developing laser systems that can create precise predetermined shot patterns for providing areas of varying softness in the lens of an eye. These areas of varying softness may have shapes that correspond to instruments used to remove material from the lens of the eye. There is further provided a multiplicity of spheres pattern, which may provide for bubble formation which in turn lubricates the lens material for removal after sectioning.

24 Claims, 14 Drawing Sheets

Related U.S. Application Data

12/217,295, filed on Jul. 2, 2008, which is a continuation-in-part of application No. PCT/US2007/001486, filed on Jan. 19, 2007, said application No. 12/217,285 is a continuation-in-part of application No. 11/414,838, filed on May 1, 2006, now Pat. No. 8,262,646, which is a continuation-in-part of application No. 11/337,127, filed on Jan. 20, 2006, and a continuation-in-part of application No. 11/414,819, filed on May 1, 2006, now Pat. No. 9,180,051, said application No. 12/217,295 is a continuation-in-part of application No. 11/414,838, filed on May 1, 2006, now Pat. No. 8,262,646.

(60) Provisional application No. 61/228,560, filed on Jul. 25, 2009, provisional application No. 61/228,529, filed on Jul. 24, 2009.

(56) References Cited

U.S. PATENT DOCUMENTS

| | | | |
|---|---|---|---|
| 4,403,841 | A | 9/1983 | Lang et al. |
| 4,461,294 | A | 7/1984 | Baron |
| 4,477,159 | A | 10/1984 | Mizuno et al. |
| 4,502,816 | A | 3/1985 | Creter, Jr. et al. |
| 4,517,980 | A | 5/1985 | Tagnon |
| 4,537,193 | A | 8/1985 | Tanner |
| 4,538,608 | A | 9/1985 | L'Esperance, Jr. |
| 4,554,917 | A | 11/1985 | Tagnon |
| 4,561,436 | A | 12/1985 | Munnerlyn |
| 4,565,197 | A | 1/1986 | Daly |
| 4,573,778 | A | 3/1986 | Shapiro |
| 4,576,160 | A | 3/1986 | Tanaka |
| 4,579,430 | A | 4/1986 | Bille |
| 4,580,559 | A | 4/1986 | L'Esperance |
| 4,582,405 | A | 4/1986 | Muller et al. |
| 4,583,539 | A | 4/1986 | Karlin et al. |
| 4,588,505 | A | 5/1986 | Walley et al. |
| 4,601,037 | A | 7/1986 | McDonald |
| 4,601,288 | A | 7/1986 | Myers |
| 4,607,622 | A | 8/1986 | Fritch et al. |
| 4,628,416 | A | 12/1986 | Dewey |
| 4,633,866 | A | 1/1987 | Peyman et al. |
| 4,638,801 | A | 1/1987 | Daly et al. |
| 4,644,948 | A | 2/1987 | Lang et al. |
| 4,648,400 | A | 3/1987 | Schneider et al. |
| 4,657,013 | A | 4/1987 | Hoerenz et al. |
| 4,665,913 | A | 5/1987 | L'Esperance, Jr. |
| 4,669,466 | A | 6/1987 | L'Esperance, Jr. |
| 4,669,839 | A | 6/1987 | Muchel |
| 4,682,595 | A | 7/1987 | Hoerenz et al. |
| 4,686,979 | A | 8/1987 | Gruen et al. |
| 4,686,992 | A | 8/1987 | Dewey et al. |
| 4,702,245 | A | 10/1987 | Schroder et al. |
| 4,702,576 | A | 10/1987 | Magnante |
| 4,711,540 | A | 12/1987 | Yoshino et al. |
| 4,711,541 | A | 12/1987 | Yoshino et al. |
| 4,712,543 | A | 12/1987 | Baron |
| 4,715,703 | A | 12/1987 | Cornsweet et al. |
| 4,718,418 | A | 1/1988 | L'Esperance, Jr. |
| 4,719,912 | A | 1/1988 | Weinberg |
| 4,721,379 | A | 1/1988 | L'Esperance |
| 4,724,522 | A | 2/1988 | Belgorod |
| 4,729,372 | A | 3/1988 | L'Esperance, Jr. |
| 4,729,373 | A | 3/1988 | Peyman |
| 4,732,148 | A | 3/1988 | L'Esperance, Jr. |
| 4,732,460 | A | 3/1988 | Kele et al. |
| 4,736,744 | A | 4/1988 | Koike et al. |
| 4,741,612 | A | 5/1988 | Birngruber et al. |
| 4,744,362 | A | 5/1988 | Gründler |
| 4,758,081 | A | 7/1988 | Barnes |
| 4,765,336 | A | 8/1988 | Blaha et al. |
| 4,770,162 | A | 9/1988 | L'Esperance et al. |
| 4,770,172 | A | 9/1988 | L'Esperance, Jr. |
| 4,770,486 | A | 9/1988 | Wang et al. |
| 4,772,116 | A | 9/1988 | Schroder et al. |
| 4,773,414 | A | 9/1988 | L'Esperance, Jr. |
| 4,775,361 | A | 10/1988 | Jacques et al. |
| 4,776,687 | A | 10/1988 | Nakanishi et al. |
| 4,798,204 | A | 1/1989 | L'Esperance, Jr. |
| 4,820,264 | A | 4/1989 | Matsui et al. |
| 4,830,483 | A | 5/1989 | Kohayakawa et al. |
| 4,832,043 | A | 5/1989 | Ichihashi |
| 4,837,857 | A | 6/1989 | Scheller et al. |
| 4,838,266 | A | 6/1989 | Koziol et al. |
| 4,840,175 | A | 6/1989 | Peyman |
| 4,846,172 | A | 7/1989 | Berlin |
| 4,848,340 | A | 7/1989 | Bille et al. |
| 4,854,693 | A | 8/1989 | Ichihashi et al. |
| 4,856,513 | A | 8/1989 | Muller |
| 4,862,888 | A | 9/1989 | Yessik |
| 4,863,261 | A | 9/1989 | Flammer |
| 4,865,029 | A | 9/1989 | Pankratov |
| 4,865,441 | A | 9/1989 | Reis |
| 4,866,243 | A | 9/1989 | Sakane et al. |
| 4,870,952 | A | 10/1989 | Martinez |
| 4,881,808 | A | 11/1989 | Bille et al. |
| 4,883,351 | A | 11/1989 | Weiss |
| 4,884,884 | A | 12/1989 | Reis |
| 4,887,019 | A | 12/1989 | Reis et al. |
| 4,887,592 | A | 12/1989 | Loertscher |
| 4,891,043 | A | 1/1990 | Zeimer et al. |
| 4,900,143 | A | 2/1990 | Bessler et al. |
| 4,900,145 | A | 2/1990 | Akiyama |
| 4,901,718 | A | 2/1990 | Bille et al. |
| 4,902,124 | A | 2/1990 | Roy, Sr. et al. |
| 4,903,695 | A | 2/1990 | Warner et al. |
| 4,905,711 | A | 3/1990 | Bennett et al. |
| 4,907,586 | A | 3/1990 | Billie et al. |
| 4,911,160 | A | 3/1990 | Thyzel |
| 4,911,711 | A | 3/1990 | Telfair et al. |
| 4,917,486 | A | 4/1990 | Raven et al. |
| 4,931,053 | A | 6/1990 | L'Esperance, Jr. |
| 4,941,093 | A | 7/1990 | Marshall et al. |
| 4,951,663 | A | 8/1990 | L'Esperance, Jr. |
| 4,953,969 | A | 9/1990 | Fedorov |
| 4,966,577 | A | 10/1990 | Crosson et al. |
| 4,972,836 | A | 11/1990 | Schenck et al. |
| 4,973,330 | A | 11/1990 | Azema et al. |
| 4,976,709 | A | 12/1990 | Sand |
| 4,988,348 | A | 1/1991 | Bille |
| 4,994,058 | A | 2/1991 | Raven et al. |
| 5,000,561 | A | 3/1991 | Lawniczak et al. |
| 5,000,751 | A | 3/1991 | Schroder et al. |
| 5,002,571 | A | 3/1991 | O'Donnell, Jr. et al. |
| 5,013,311 | A | 5/1991 | Nouri |
| 5,019,074 | A | 5/1991 | Muller |
| 5,041,134 | A | 8/1991 | O'Donnell |
| 5,048,946 | A | 9/1991 | Sklar et al. |
| 5,049,147 | A | 9/1991 | Danon |
| 5,054,907 | A | 10/1991 | Skylar et al. |
| 5,057,102 | A | 10/1991 | Tomioka et al. |
| 5,067,951 | A | 11/1991 | Greve |
| 5,090,798 | A | 2/1992 | Kohayakawa |
| 5,092,863 | A | 3/1992 | Schanzlin |
| 5,094,521 | A | 3/1992 | Jolson et al. |
| 5,098,426 | A | 3/1992 | Sklar et al. |
| 5,102,409 | A | 4/1992 | Balgorod |
| 5,108,388 | A | 4/1992 | Trokel |
| 5,108,412 | A | 4/1992 | Krumeich et al. |
| 5,112,328 | A | 5/1992 | Taboada et al. |
| 5,116,114 | A | 5/1992 | Nakamura et al. |
| 5,122,135 | A | 6/1992 | Durr et al. |
| 5,123,902 | A | 6/1992 | Muller et al. |
| 5,128,509 | A | 7/1992 | Black et al. |
| 5,133,708 | A | 7/1992 | Smith |
| 5,137,530 | A | 8/1992 | Sand |
| 5,141,506 | A | 8/1992 | York |
| 5,147,349 | A | 9/1992 | Johnson et al. |
| 5,147,352 | A | 9/1992 | Azema et al. |
| 5,152,055 | A | 10/1992 | L'Esperance, III et al. |
| 5,152,759 | A | 10/1992 | Parel et al. |
| 5,163,934 | A | 11/1992 | Munnerlyn |

(56) References Cited

U.S. PATENT DOCUMENTS

| | | |
|---|---|---|
| 5,171,242 A | 12/1992 | Dewey et al. |
| 5,174,021 A | 12/1992 | L'Esperance, III et al. |
| 5,178,635 A | 1/1993 | Gwon et al. |
| 5,188,631 A | 2/1993 | L'Esperance, Jr. |
| 5,194,948 A | 3/1993 | L'Esperance, III et al. |
| 5,196,006 A | 3/1993 | Klopotek et al. |
| 5,196,027 A | 3/1993 | Thompson et al. |
| 5,201,730 A | 4/1993 | Easley et al. |
| 5,202,708 A | 4/1993 | Sasaki et al. |
| 5,203,353 A | 4/1993 | Easley et al. |
| 5,207,668 A | 5/1993 | L'Esperance, Jr. |
| 5,213,092 A | 5/1993 | Uram |
| 5,215,104 A | 6/1993 | Steinert |
| 5,217,459 A | 6/1993 | Kamerling |
| 5,219,343 A | 6/1993 | L'Esperance, Jr. |
| 5,219,344 A | 6/1993 | Yoder, Jr. |
| 5,222,981 A | 6/1993 | Werblin |
| 5,224,942 A | 7/1993 | Beuchat et al. |
| 5,226,903 A | 7/1993 | Mizuno |
| 5,246,435 A | 9/1993 | Billie et al. |
| 5,246,436 A | 9/1993 | Rowe |
| 5,257,988 A | 11/1993 | L'Esperance, Jr. |
| 5,258,025 A | 11/1993 | Fedorov et al. |
| 5,263,950 A | 11/1993 | L'Esperance, Jr. |
| 5,263,951 A | 11/1993 | Spears et al. |
| 5,275,593 A | 1/1994 | Easley et al. |
| 5,277,911 A | 1/1994 | Viegas et al. |
| 5,279,298 A | 1/1994 | Flower |
| 5,279,611 A | 1/1994 | McDonnell et al. |
| 5,281,211 A | 1/1994 | Parel et al. |
| 5,282,798 A | 2/1994 | Bruse et al. |
| 5,284,477 A | 2/1994 | Hanna et al. |
| 5,288,293 A | 2/1994 | O'Donnell, Jr. |
| 5,290,272 A | 3/1994 | Burstein et al. |
| 5,295,989 A | 3/1994 | Nakamura |
| 5,300,020 A | 4/1994 | L'Esperance, Jr. |
| 5,300,061 A | 4/1994 | Easley et al. |
| 5,300,062 A | 4/1994 | Ueno |
| 5,300,063 A | 4/1994 | Tano et al. |
| 5,300,114 A | 4/1994 | Gwon et al. |
| 5,304,168 A | 4/1994 | Sun |
| 5,304,169 A | 4/1994 | Sand |
| 5,311,224 A | 5/1994 | Enomoto |
| 5,312,320 A | 5/1994 | L'Esperance, Jr. |
| 5,312,393 A | 5/1994 | Mastel |
| 5,314,422 A | 5/1994 | Nizzola |
| 5,318,047 A | 6/1994 | Davenport et al. |
| 5,318,560 A | 6/1994 | Blount et al. |
| 5,323,788 A | 6/1994 | Silvestrini et al. |
| 5,324,281 A | 6/1994 | Muller |
| 5,325,134 A | 6/1994 | Kohayakawa |
| 5,334,190 A | 8/1994 | Seiler |
| 5,336,215 A | 8/1994 | Hsueh et al. |
| 5,336,216 A | 8/1994 | Dewey |
| 5,342,351 A | 8/1994 | Blaha et al. |
| 5,342,370 A | 8/1994 | Simon et al. |
| 5,345,948 A | 9/1994 | O'Donnell, Jr. |
| 5,346,491 A | 9/1994 | Oertli |
| 5,347,329 A | 9/1994 | Ota |
| 5,348,551 A | 9/1994 | Spears et al. |
| 5,350,374 A | 9/1994 | Smith |
| 5,354,331 A | 10/1994 | Schachar |
| 5,355,181 A | 10/1994 | Ashizaki et al. |
| 5,356,407 A | 10/1994 | Easley et al. |
| 5,356,409 A | 10/1994 | Nizzola |
| 5,360,424 A | 11/1994 | Klopotek |
| 5,364,388 A | 11/1994 | Koziol |
| 5,364,390 A | 11/1994 | Taboada et al. |
| 5,368,590 A | 11/1994 | Itoh |
| 5,370,641 A | 12/1994 | O'Donnell, Jr. |
| 5,372,595 A | 12/1994 | Gaasterland et al. |
| 5,374,265 A | 12/1994 | Sand |
| 5,376,086 A | 12/1994 | Khoobehi et al. |
| 5,391,165 A | 2/1995 | Fountain et al. |
| 5,395,356 A | 3/1995 | King et al. |
| 5,403,307 A | 4/1995 | Zelman |
| 5,408,484 A | 4/1995 | Weimel |
| 5,411,501 A | 5/1995 | Klopotek |
| 5,412,561 A | 5/1995 | Rosenshein et al. |
| 5,413,555 A | 5/1995 | McMahan |
| 5,423,798 A | 6/1995 | Crow |
| 5,423,800 A | 6/1995 | Ren et al. |
| 5,423,801 A | 6/1995 | Marshall et al. |
| 5,425,727 A | 6/1995 | Koziol |
| 5,425,729 A | 6/1995 | Ishida et al. |
| 5,425,730 A | 6/1995 | Luloh |
| 5,437,657 A | 8/1995 | Epstein |
| 5,437,658 A | 8/1995 | Muller et al. |
| 5,439,462 A | 8/1995 | Bille et al. |
| 5,441,496 A | 8/1995 | Easley et al. |
| 5,441,511 A | 8/1995 | Hanna |
| 5,442,412 A | 8/1995 | Frey et al. |
| 5,442,487 A | 8/1995 | Mizuno |
| 5,445,633 A | 8/1995 | Nakamura et al. |
| 5,460,627 A | 10/1995 | O'Donnell, Jr. |
| 5,461,212 A | 10/1995 | Seiler et al. |
| 5,462,739 A | 10/1995 | Dan et al. |
| 5,465,737 A | 11/1995 | Schachar |
| 5,470,329 A | 11/1995 | Sumiya |
| 5,474,548 A | 12/1995 | Knopp et al. |
| 5,476,511 A | 12/1995 | Gwon et al. |
| 5,480,396 A | 1/1996 | Simon et al. |
| 5,484,432 A | 1/1996 | Sand |
| 5,489,299 A | 2/1996 | Schachar |
| 5,503,165 A | 4/1996 | Schachar |
| 5,507,740 A | 4/1996 | O'Donnell, Jr. |
| 5,514,124 A | 5/1996 | Alpins |
| 5,514,125 A | 5/1996 | Lasser et al. |
| 5,520,679 A | 5/1996 | Lin |
| 5,527,774 A | 6/1996 | Girard |
| 5,529,076 A | 6/1996 | Schachar |
| 5,533,997 A | 7/1996 | Ruiz |
| 5,548,352 A | 8/1996 | Dewey |
| 5,556,395 A | 9/1996 | Shimmick et al. |
| 5,573,544 A | 11/1996 | Simon et al. |
| 5,594,753 A | 1/1997 | Frey et al. |
| 5,607,472 A | 3/1997 | Thompson |
| 5,616,139 A | 4/1997 | Okamoto |
| 5,618,284 A | 4/1997 | Sand |
| 5,620,435 A | 4/1997 | Belkin et al. |
| 5,627,162 A | 5/1997 | Gwon et al. |
| 5,632,742 A | 5/1997 | Frey et al. |
| 5,651,782 A | 7/1997 | Simon et al. |
| 5,656,186 A | 8/1997 | Mourou et al. |
| 5,684,560 A | 11/1997 | Roffman et al. |
| 5,699,142 A | 12/1997 | Lee et al. |
| 5,709,868 A | 1/1998 | Perricone |
| 5,722,952 A | 3/1998 | Schachar |
| 5,722,970 A | 3/1998 | Colvard et al. |
| 5,731,909 A | 3/1998 | Schachar |
| 5,738,677 A | 4/1998 | Colvard et al. |
| 5,752,950 A | 5/1998 | Frey et al. |
| 5,757,462 A | 5/1998 | Nanjo |
| 5,773,472 A | 6/1998 | Stjernschantz et al. |
| 5,828,686 A | 10/1998 | Frey et al. |
| 5,843,184 A | 12/1998 | Cionni |
| 5,849,006 A | 12/1998 | Frey et al. |
| 5,886,768 A | 3/1999 | Knopp et al. |
| 5,907,908 A | 6/1999 | Cunanan et al. |
| 5,912,915 A | 6/1999 | Reed et al. |
| 5,919,186 A | 7/1999 | Bath |
| 5,980,513 A | 11/1999 | Frey et al. |
| 5,984,916 A | 11/1999 | Lai |
| 5,993,441 A | 11/1999 | Muller et al. |
| 6,007,578 A | 12/1999 | Schachar |
| 6,013,101 A | 1/2000 | Israel |
| 6,019,472 A | 2/2000 | Koester et al. |
| 6,022,088 A | 2/2000 | Metzler |
| 6,027,494 A | 2/2000 | Frey |
| 6,055,259 A | 4/2000 | Frey et al. |
| 6,059,772 A | 5/2000 | Hsia et al. |
| 6,070,981 A | 6/2000 | Mihashi et al. |
| 6,099,522 A | 8/2000 | Knopp et al. |
| 6,114,651 A | 9/2000 | Schluter et al. |

(56) References Cited

U.S. PATENT DOCUMENTS

| | | |
|---|---|---|
| 6,132,424 A | 10/2000 | Tang |
| 6,186,148 B1 | 2/2001 | Okada |
| 6,190,375 B1 | 2/2001 | Frey |
| 6,197,018 B1 | 3/2001 | O'Donnell |
| 6,197,056 B1 | 3/2001 | Schachar |
| 6,252,595 B1 | 6/2001 | Birmingham et al. |
| 6,254,595 B1 | 7/2001 | Juhasz et al. |
| 6,261,220 B1 | 7/2001 | Frey et al. |
| 6,271,914 B1 | 8/2001 | Frey et al. |
| 6,271,915 B1 | 8/2001 | Frey et al. |
| 6,275,718 B1 | 8/2001 | Lempert |
| 6,280,435 B1 | 8/2001 | Odrich et al. |
| 6,280,468 B1 | 8/2001 | Schachar |
| 6,299,640 B1 | 10/2001 | Schachar |
| 6,302,879 B1 | 10/2001 | Frey et al. |
| 6,312,422 B1 | 11/2001 | Dubnack |
| 6,312,424 B1 | 11/2001 | Largent |
| 6,313,165 B1 | 11/2001 | Grunberger et al. |
| 6,315,773 B1 | 11/2001 | Frey et al. |
| 6,319,274 B1 | 11/2001 | Shadduck |
| 6,322,545 B1 | 11/2001 | Schachar |
| 6,322,556 B1 | 11/2001 | Gwon et al. |
| 6,324,191 B1 | 11/2001 | Horvath |
| 6,325,791 B1 | 12/2001 | Shimoji |
| 6,328,732 B1 | 12/2001 | Donitzky et al. |
| 6,344,040 B1 | 2/2002 | Juhasz et al. |
| 6,373,571 B1 | 4/2002 | Juhasz et al. |
| D459,806 S | 7/2002 | Webb |
| D459,807 S | 7/2002 | Webb |
| 6,413,262 B2 | 7/2002 | Saishin et al. |
| D462,442 S | 9/2002 | Webb |
| D462,443 S | 9/2002 | Webb |
| 6,451,008 B1 | 9/2002 | Frey et al. |
| 6,460,997 B1 | 10/2002 | Frey et al. |
| 6,467,906 B1 | 10/2002 | Alpins |
| 6,493,151 B2 | 12/2002 | Schachar |
| 6,494,910 B1 | 12/2002 | Ganem et al. |
| 6,497,483 B2 | 12/2002 | Frey et al. |
| 6,530,917 B1 | 3/2003 | Seiler et al. |
| 6,544,254 B1 | 4/2003 | Bath |
| 6,547,394 B2 | 4/2003 | Doherty |
| 6,554,825 B1 | 4/2003 | Murray et al. |
| 6,585,726 B2 | 7/2003 | Frey et al. |
| 6,588,902 B2 | 7/2003 | Isogai |
| 6,588,903 B2 | 7/2003 | Rathjen |
| 6,592,574 B1 | 7/2003 | Shimmick et al. |
| 6,610,686 B1 | 8/2003 | Enrico et al. |
| 6,623,476 B2 | 9/2003 | Juhasz et al. |
| 6,626,445 B2 | 9/2003 | Murphy et al. |
| 6,626,893 B2 | 9/2003 | Frey et al. |
| 6,626,894 B2 | 9/2003 | Frey et al. |
| 6,626,895 B2 | 9/2003 | Frey et al. |
| 6,626,896 B2 | 9/2003 | Frey et al. |
| 6,626,897 B2 | 9/2003 | Frey et al. |
| 6,626,898 B2 | 9/2003 | Frey et al. |
| 6,648,877 B1 | 11/2003 | Juhasz et al. |
| 6,669,342 B2 | 12/2003 | Liebermann et al. |
| 6,676,653 B2 | 1/2004 | Juhasz et al. |
| 6,693,927 B1 | 2/2004 | Horvath et al. |
| 6,726,679 B1 | 4/2004 | Dick et al. |
| 6,849,091 B1 | 2/2005 | Cumming |
| 6,863,667 B2 | 3/2005 | Webb et al. |
| 6,905,641 B2 | 6/2005 | Platt et al. |
| 6,923,955 B2 | 8/2005 | Till et al. |
| 6,962,583 B2 | 11/2005 | Kadziauskas et al. |
| 7,044,568 B2 | 5/2006 | Olivera et al. |
| 7,077,838 B2 | 7/2006 | Wong |
| 7,182,759 B2 | 2/2007 | Kadziauskas et al. |
| 7,188,949 B2 | 3/2007 | Bandhauer et al. |
| 7,220,255 B2 | 5/2007 | Lai |
| 7,252,662 B2 | 8/2007 | McArdle et al. |
| 7,264,355 B2 | 9/2007 | Rathjen |
| RE40,002 E | 1/2008 | Lin |
| RE40,184 E | 3/2008 | Lin |
| 7,338,167 B2 | 3/2008 | Zelvin et al. |
| 7,357,504 B2 | 4/2008 | Fischer et al. |
| 7,364,575 B2 | 4/2008 | Van Saarloos |
| 7,390,089 B2 | 6/2008 | Loesel et al. |
| RE40,420 E | 7/2008 | Dick et al. |
| 7,402,159 B2 | 7/2008 | Loesel et al. |
| 7,467,871 B2 | 12/2008 | Lawhorn et al. |
| 7,479,106 B2 | 1/2009 | Banik et al. |
| 7,540,613 B2 | 6/2009 | Severns |
| 7,655,002 B2 | 2/2010 | Myers |
| 7,717,908 B2 | 5/2010 | Ruiz et al. |
| 7,766,903 B2 | 8/2010 | Blumenkranz et al. |
| 7,836,894 B2 | 11/2010 | Brinkmann et al. |
| 7,959,289 B2 | 6/2011 | Cattin-Liebl |
| 8,262,553 B2 | 9/2012 | Weston et al. |
| 8,262,646 B2 | 9/2012 | Frey et al. |
| 8,382,745 B2 | 2/2013 | Naranjo-Tackman et al. |
| 8,465,478 B2 | 6/2013 | Frey et al. |
| 8,500,723 B2 | 8/2013 | Frey et al. |
| 8,556,425 B2 | 10/2013 | Frey et al. |
| 2001/0029363 A1 | 10/2001 | Lin |
| 2002/0004658 A1 | 1/2002 | Munnerlyn et al. |
| 2002/0025311 A1 | 2/2002 | Till |
| 2002/0029053 A1 | 3/2002 | Gordon |
| 2002/0049450 A1 | 4/2002 | Myers |
| 2002/0103478 A1 | 8/2002 | Gwon et al. |
| 2002/0110549 A1 | 8/2002 | Till |
| 2002/0138139 A1 | 9/2002 | Till |
| 2002/0140903 A1 | 10/2002 | Schachar |
| 2002/0159028 A1 | 10/2002 | Masaki |
| 2003/0050629 A1 | 3/2003 | Kadziauskas et al. |
| 2003/0055412 A1 | 3/2003 | Lieberman et al. |
| 2003/0076477 A1 | 4/2003 | Matsumoto |
| 2003/0076508 A1 | 4/2003 | Cornsweet |
| 2003/0109926 A1 | 6/2003 | Portney |
| 2003/0135272 A1 | 7/2003 | Brady et al. |
| 2003/0139737 A1 | 7/2003 | Lin |
| 2003/0212387 A1 | 11/2003 | Kurtz et al. |
| 2003/0220630 A1 | 11/2003 | Lin et al. |
| 2004/0054359 A1 | 3/2004 | Ruiz et al. |
| 2004/0059321 A1 | 3/2004 | Knopp et al. |
| 2004/0070761 A1 | 4/2004 | Horvath et al. |
| 2004/0143244 A1 | 7/2004 | Gray et al. |
| 2004/0156014 A1 | 8/2004 | Piers et al. |
| 2004/0199149 A1 | 10/2004 | Myers et al. |
| 2004/0199150 A1 | 10/2004 | Lai |
| 2004/0243111 A1 | 12/2004 | Bendett et al. |
| 2004/0249403 A1 | 12/2004 | Loomas et al. |
| 2005/0107773 A1 | 5/2005 | Bergt et al. |
| 2005/0107775 A1 | 5/2005 | Huang et al. |
| 2005/0165387 A1* | 7/2005 | Lubatschowski ....... A61F 9/008 606/5 |
| 2005/0197655 A1 | 9/2005 | Telfair et al. |
| 2005/0203492 A1 | 9/2005 | Nguyen et al. |
| 2005/0243276 A1 | 11/2005 | Van Heugten et al. |
| 2005/0270486 A1 | 12/2005 | Teiwes et al. |
| 2005/0286019 A1 | 12/2005 | Wiltberger et al. |
| 2006/0058682 A1 | 3/2006 | Miller et al. |
| 2006/0192921 A1 | 8/2006 | Loesel et al. |
| 2006/0195076 A1 | 8/2006 | Blumenkranz et al. |
| 2006/0215111 A1 | 9/2006 | Mijashi |
| 2006/0259022 A1 | 11/2006 | Lin |
| 2007/0010803 A1 | 1/2007 | Bischoff et al. |
| 2007/0078447 A1 | 4/2007 | Weinacht et al. |
| 2007/0093795 A1 | 4/2007 | Melcher et al. |
| 2007/0093796 A1 | 4/2007 | Raksi et al. |
| 2007/0129693 A1 | 6/2007 | Hunter et al. |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0265603 A1 | 11/2007 | Pinelli |
| 2008/0071254 A1 | 3/2008 | Lummis et al. |
| 2008/0111972 A1 | 5/2008 | Barth et al. |
| 2008/0186551 A1 | 8/2008 | Hanft et al. |
| 2008/0281303 A1 | 11/2008 | Culbertson et al. |
| 2008/0312675 A1 | 12/2008 | Newcott et al. |
| 2009/0012507 A1* | 1/2009 | Culbertson et al. ............... 606/6 |
| 2009/0069794 A1 | 3/2009 | Kurtz |
| 2009/0088734 A1 | 4/2009 | Mordaunt |
| 2009/0126870 A1 | 5/2009 | Zadoyan et al. |

(56) References Cited

U.S. PATENT DOCUMENTS

| | | |
|---|---|---|
| 2009/0131921 A1 | 5/2009 | Kurtz |
| 2009/0137988 A1 | 5/2009 | Kurtz |
| 2009/0137991 A1 | 5/2009 | Kurtz |
| 2009/0137993 A1 | 5/2009 | Kurtz |
| 2009/0157063 A1 | 6/2009 | Ruiz et al. |
| 2009/0161065 A1 | 6/2009 | Smith, III et al. |
| 2009/0171327 A1 | 7/2009 | Kurtz et al. |
| 2009/0177189 A1 | 7/2009 | Raksi |
| 2009/0187178 A1 | 7/2009 | Muller et al. |
| 2009/0192389 A1 | 7/2009 | Eilers et al. |
| 2009/0244482 A1 | 10/2009 | Eisener et al. |
| 2009/0281530 A1 | 11/2009 | Korn |
| 2010/0002837 A1 | 1/2010 | Gertner et al. |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0060855 A1 | 3/2010 | Graether |
| 2010/0114079 A1 | 5/2010 | Myers et al. |
| 2010/0256614 A1 | 10/2010 | Donitzky et al. |
| 2010/0256615 A1 | 10/2010 | Blumenkranz et al. |
| 2010/0274228 A1 | 10/2010 | Mrochen et al. |
| 2010/0292676 A1 | 11/2010 | Larsen |
| 2010/0312231 A1 | 12/2010 | Singh |
| 2010/0324542 A1 | 12/2010 | Kurtz |
| 2010/0331829 A1 | 12/2010 | Bor et al. |
| 2011/0022035 A1 | 1/2011 | Porter et al. |
| 2011/0022036 A1 | 1/2011 | Frey et al. |
| 2011/0028950 A1 | 2/2011 | Raksi et al. |
| 2011/0092965 A1 | 4/2011 | Slatkine |
| 2011/0118712 A1 | 5/2011 | Lubatschowski et al. |
| 2011/0137301 A1 | 6/2011 | Bartoli |
| 2011/0149240 A1 | 6/2011 | Alpins |
| 2011/0160710 A1 | 6/2011 | Frey et al. |
| 2011/0160711 A1 | 6/2011 | Naranjo-Tackman et al. |
| 2011/0166557 A1 | 7/2011 | Naranjo-Tackman et al. |
| 2011/0184395 A1 | 7/2011 | Schuele et al. |
| 2011/0187995 A1 | 8/2011 | Frey et al. |
| 2011/0190739 A1 | 8/2011 | Frey et al. |
| 2011/0190740 A1 | 8/2011 | Frey et al. |
| 2011/0292340 A1 | 12/2011 | Shimizu et al. |
| 2012/0016350 A1 | 1/2012 | Myers et al. |
| 2012/0089134 A1 | 4/2012 | Horvath et al. |
| 2012/0182522 A1 | 7/2012 | Frey et al. |
| 2012/0265181 A1 | 10/2012 | Frey |
| 2012/0271286 A1 | 10/2012 | Curatu et al. |
| 2012/0296321 A1 | 11/2012 | Frey et al. |
| 2012/0330290 A1 | 12/2012 | Gray et al. |
| 2013/0265542 A1 | 10/2013 | Frey et al. |

FOREIGN PATENT DOCUMENTS

| | | |
|---|---|---|
| EP | 0 397 962 A1 | 11/1990 |
| EP | 0 933 060 A1 | 8/1999 |
| EP | 1 970 034 A1 | 9/2008 |
| FR | 2 497 087 A1 | 7/1982 |
| WO | WO 91/19539 A1 | 12/1991 |
| WO | WO 01/13838 A1 | 3/2001 |
| WO | WO 03/002010 A1 | 1/2003 |
| WO | WO 2005/070358 A1 | 8/2005 |
| WO | WO 2006/074469 A1 | 7/2006 |
| WO | WO 2008/112292 A1 | 9/2008 |
| WO | WO 2012/051490 A1 | 4/2012 |

OTHER PUBLICATIONS

U.S. Appl. No. 11/414,819, filed May 1, 2006, Frey et al.
U.S. Appl. No. 12/217,285, filed Jul. 2, 2008, Frey et al.
U.S. Appl. No. 12/217,295, filed Jul. 2, 2008, Frey et al.
U.S. Appl. No. 12/509,021, filed Jul. 24, 2009, Frey et al.
U.S. Appl. No. 12/509,211, filed Jul. 24, 2009, Frey et al.
U.S. Appl. No. 12/509,412, filed Jul. 24, 2009, Frey et al.
U.S. Appl. No. 12/685,850, filed Jan. 12, 2010, Myers et al.
U.S. Appl. No. 12/831,845, filed Jul. 7, 2010, Naranjo-Tackman et al.
U.S. Appl. No. 12/831,859, filed Jul. 7, 2010, Naranjo-Tackman et al.
U.S. Appl. No. 12/831,783, filed Jul. 7, 2010, Frey et al.
U.S. Appl. No. 12/840,818, filed Jul. 21, 2010, Porter et al.
U.S. Appl. No. 29/377,018, filed Oct. 15, 2010, Bott et al.
U.S. Appl. No. 29/377,054, filed Oct. 15, 2010, Bott et al.
U.S. Appl. No. 13/016,593, filed Jan. 28, 2011, Frey et al.
U.S. Appl. No. 13/017,499, filed Jan. 31, 2011, Frey et al.
U.S. Appl. No. 13/017,702, filed Jan. 31, 2011, Frey et al.
U.S. Appl. No. 13/243,406, filed Sep. 23, 2011, Myers et al.
U.S. Appl. No. 13/273,653, filed Oct. 14, 2011, Frey et al.
U.S. Appl. No. 13/427,130, filed Mar. 22, 2012, Frey.
U.S. Appl. No. 13/427,149, filed Mar. 22, 2012, Frey et al.
U.S. Appl. No. 13/427,319, filed Mar. 22, 2012, Grey et al.
U.S. Appl. No. 13/435,103, filed Mar. 30, 2012, Curatu et al.
U.S. Appl. No. 13/681,004, filed Nov. 19, 2012, Frey et al.
FDA PMA P030002 titled "crystalens™ Model AT-45 Accomodating Posterior Chamber Intraocular Lens (OIO)", dated Nov. 14, 2003, 16 pgs.
FDA PMA P040020 titled "AcrySof® ResSTOR® Apodized Diffractive Optic Posterior Chamber Intraocular Lenses, Models MA60d3 and SA60D3", dated Mar. 21, 2005, 29 pgs.
Author unknown, "Statement of the Use of Animals in Opthalmic and Visual Research", The Association for Research in Vision and Opthalmology, Obtained from the Internet at: http"//www.arvo.org/aboutavro as of Nov. 18, 2010, 3 pgs.
Akchurin, Garif et al., "Evaluation of the degree of turbidity if cataract lens and its correlation with retinal visual acuity", *SPIE*, vol. 3591, Jan. 1999, pp. 74-81.
Al-Ghoul, K. J. et al., "Distribution and Type of Morphological Damage in Human Nuclear Age-Related Cataracts", *Department of Cell Biology and Anatomy, University of North Carolina and Duke University Eye Center*, 1996, pp. 237-251.
Al-Ghoul, Kristin J. et al., "Structural Evidence of Human Nuclear Fiber Compaction as a Function of Ageing and Cataractogenesis", *Exp. Eye Res.*, vol. 72, 2001, pp. 199-214.
Alio, et al., "Crystalline Lens Optical Dysfunction through Aging", *Ophthalmology*, vol. 112, No. 11, Nov. 2005, pp. 2022-2029.
Amann, Josef et al., "Increased Endothelial Cell Density in the Paracentral and Peripheral Regions of the Human Cornea", *American Journal of Ophthalmology*, vol. 135, No. 5, May 2003, pp. 584-590.
Amendt, M. Strauss et al., "Modeling of bubble dynamics in relation to medical applications", *Proc. of SPIE*, vol. 2975, 1997, pp. 362-373.
Ansari, Rafat R. et al., "Measuring lens opacity: combining quasi-elastic light scattering with Scheimpflug imaging system", *Proc. of SPIE*, vol. 3246, 1998, pp. 35-42.
Anschutz, Till, M.D., "Laser Correction of Hyperopia and Presbyopia", vol. 34, No. 4, 1994, pp. 107-137.
Apple, David J. et al., "Preparation and Study of Human Eyes Obtained Postmortem with the Miyake Posterior Photographic Technique", *Ophthalmology*, vol. 97, No. 6, Jun. 1990, pp. 810-816.
Armstrong, Larry "A cataract Breakthrough May Be on the Way", *Business Week*, Mar. 23, 1998, pp. 90-92.
Aston, Adam, "Why Settle for 20/20?", *Business Week*, Mar. 17, 2003, pp. 95-96.
Azzam, Naiel et al., "Long-term lens organ culture system to determine age-related effects of UV irradiation on the eye lens", *Experimental Eye Research*, vol. 79, 2004, pp. 903-911.
Back, Arthur P. et al., "Correction of Presbyopia with Contact Lenses: Comparative Success Rates with Three Systems", *Optometry & Vision Science*, 1989, vol. 66, No. 8, pp. 518-525.
Balaram, Mini et al., Noncontact Specular Microscopy of Human Lens Epithelium, *IOVS*, vol. 41, No. 2, Feb. 2000, pp. 474-481.
Barak, Adiel et al., "Anterior capsulotomy using the $CO_2$ laser", *Proc. of SPIE*, vol. 3246, 1998, pp. 196-198.
Bath, Patricia E. et al., "Endocapsular Excimer Laser Phakoablation Through a 1-mm Incision", *Opthalmic Laser Therapy*, vol. 2, No. 4, 1987, pp. 245-249.
Beers, A. P. A. et al. "Age-Related Changes in the Accommodation Mechanism", *Optometry and Vision Science*, 1996, vol. 73, No. 4, pp. 235-242.

(56) References Cited

OTHER PUBLICATIONS

Beers, A. P. A. et al., "In Vivo Determination of the Biomechanical Properties of the Component Elements of the Accommodation Mechanism", *Vision Res.*, vol. 34, 1994, pp. 2897-2905.
Bellows, John G., M.D. et al., "B. Cataracta Complicata", *Traumatic Cataract*, undated but prior to Jul. 2009, pp. 270-272.
Ben-Sira, I. et al., "Clinical method for measurement of light back scattering from the in vivo human lens", *Invest. Ophthalmol. Vis. Sci.*, vol. 19, No. 4 (Reports), Apr. 1980, pp. 435-437.
Benjamin, William J., "Borish's Clinical Refraction", W.B. Saunders, publishers, copyright 1998, p. 110.
Bettelheim, Frederick A. et al., "Syneretic Response of Aging Normal Human Lens to Pressure", *Investigative Ophthalmology & Visual Science*, vol. 44, No. 1, Jan. 2003, pp. 258-263.
Bigler, Emmanuel, "Depth of field and Scheimpflug's rule: a "minimalist" geometrical approach", published unknown, 2002, pp. 1-17.
Billie, J. F. et al., "3D Imaging of the Human Eye Using the laser Tomographic Scanner Lts", publisher unknown, undated but prior to Jul. 2009, 2 pgs.
Bito, L.Z. et al., "Age-dependent loss of accommodative amplitude in rhesus monkeys: an animal model for presbyopia", *Invest. Ophthalmol. Vis. Sci.*, vol. 23, No. 1, Jul. 1982, pp. 23-31.
Bliss, E. S., "Pulse Duration Dependence of laser Damage Mechamisms", *Opto-Electronics*, vol. 3, 1971, pp. 99-108.
Bor, Zs. PhD., et al., "Plume Emission, Shock Wave and Surface Wave Formation During Excimer Laser Ablation of the Cornea", *Supplement to Retroactive & Corneal Surgery*, vol. 9, Mar./Apr. 1993, pp. S111-S115.
Borja, David et al., "Crystalline Lens MTF Measurement During Simulated Accommodation", *Proc. of SPIE*, 2005, vol. 5688, pp. 26-32.
Borkman, Raymond F. et al., "Evidence for a Free Radical Mechanism in Aging and u.v.—Irradiated Ocular Lenses", *Exp. Eye Res.*, 1977, vol. 25, pp. 303-309.
Braham, Lewis, "Eye Surgery: It's Getting Sharper", *Business Week*, Oct. 18, 2004, pp. 142-143.
Breitenfeld, P. et al., "Finite Element Method-Simulation of the Human Lens During Accommodation", publiasher unknown, vol. 5863, 2005, 9 pgs.
Breitling, Detlef et al., "Fundamental aspects in machining of metals with short and ultrashort laser pulses", *Proc. of SPIE*, vol. 5339, 2004, pp. 1-15.
Brian, G. et al., "Cataract Blindness—Challenges for the 21$^{st}$ Century", *Bulletin of the World Health Organization*, vol. 79, No. 3, 2001, pp. 249-256.
Bron, A.J., "The Ageing Lens", *Opthalmologics*, vol. 214, 2000, pp. 86-104.
Brown, Nicholas, "Dating the onset of cataract", *Transactions of the Ophthalmological Society of the United Kingdom*, vol. 96, 1976, pp. 18-23.
Brown, Nicholas "The Change in Lens Curvature with Age", *Exp. Eye Res.* (1974), vol. 19, pp. 175-183.
Brown, Nicholas "The Change in Shape and Internal Form of the Lens of the Eye on Accommodation", *Exp. Eye Res.* (1973) vol. 15, pp. 441-459.
Burd, H.J. et al., "Can reliable values of Young's modulus be deduced from Fisher's (1971) spinning lens measurements?", *Vision Research*, volume unknown, 2005, pp. 1-15.
Burd, H.J. et al., "Numerical modeling of the accommodating lens", *Vision Research*, vol. 42, 2002, pp. 2235-2251.
Campbell, Melanie C. W., "Measurement of Refractive Index in an Intact Crystalline Lens", *Vision Research*, vol. 24, No. 5, 1984, pp. 409-415.
Carey, James et al., "Propagation and Characterization of Ultrashort Laser Pulses", Harvard University, 2003, pp. 1-30.
Chaker, M. et al., "Interaction of a 1 psec laser pulse with solid matter", *Phys. Fluids B 3*, vol. 1, Jan. 1991, pp. 167-175, plus cover page.
Charles, M. W. et al., "Dimensions of the Human Eye Relevant to Radiation Protection", *Phys. Med. Biol.*, 1975, vol. 20, No. 2, © 1975, pp. 202-218.
Chen, Wei-Li et al., Ultrasound Biomicroscopic Findings in Rabbit Eyes Undergoing Scleral Suction during Lamellar Refractive Surgery, *IOVS*, vol. 43, No. 12, Dec. 2002, pp. 3665-3672.
Chien, C. Y. et al., "Production of a high-density and high-temperature plasma with an intense high-contrast subpicosecond laser", *Optics Letters*, vol. 18, No. 18, Sep. 15, 1993, pp. 1535-1537.
Claflin, E. S. et al., "Configuring an electrostatic membrane mirror by least-squares fitting with analytically derived influence functions", *J. Opt. Soc. Am. A.*, vol. 3, No. 11, 1986, pp. 1833-1839.
Coleman, D. Jackson et al., "Presbyopia, Accommodation, and the Mature Catenary", *Ophthalmology*, vol. 108, No. 9, Sep. 2001, pp. 1544-1551.
Cook, Christopher A. et al., "Aging of the Human Crystalline Lens and Anterior Segment", *Vision Res.*, 1994, vol. 34, No. 22, pp. 2945-2954.
Corkum, P. B. et al., "Thermal Response of Metals to Ultrashort-Pulse Laser Excitation", *Physical Review Letters*, vol. 61, No. 25, Dec. 19, 1988, pp. 2886-2889.
Costagliola, Ciro et al., "ArF 193 nm Excimer Laser Corneal Surgery as a Possible Risk Factor in Cataractogenesis", *Exp. Eye Res.*, 1994, vol. 58, pp. 453-457.
Cotlier, Edward, M.D., "The Lens", *Adler's Physiology of the Eye*, copyright 2003, pp. 268-290.
Crawford, Kathryn S. et al., "The Role of the Iris in Accommodation of Rhesus Monkeys", *Investigative Ophthalmology & Visual Science*, vol. 31, No. 10, Oct. 1990, pp. 2185-2190.
Croft, Mary Ann et al., "Accommodation and Presbyopia", publisher unknown, vol. 41, 2001, pp. 33-46.
Croft, Mary Ann et al., "Accommodation and Presbyopia: The Ciliary Neuromuscular View", *Opthalmol Clin N Am*, vol. 19, 2006, pp. 13-24.
Croft, Mary Ann et al., Accommodative Ciliary Body and Lens Function in Rhesus Monkeys, I: Normal Lens, Zonule and Ciliary Process Configuration in the Iridectomized Eye, *IOVS*, vol. 47, No. 3, Mar. 2006, pp. 1076-1086.
Croft, Mary Ann et al., "The Zonula, Lens, and Circumlental Space in the Normal Iridectomized Rhesus Monkey Eye", *IOVS*, vol. 47, No. 3, Mar. 2006, pp. 1087-1095.
Cromie, William J., "Laser Makes History's Fastest Holes", *The Harvard University Gazette*, 1999, obtained at: http://www.news.harvard.edu/gazette/1999/10.07/laser.html, 6 pags.
Czygan, G. et al., "Mechanical testing of isolated senile human eye lens nuclei", *Med. Eng. Phys.*, vol. 18, No. 5, 1996, pp. 345-349.
Datta, Debajyoti, "Tissue Surgery and Subcellular Photodisruption with Femtosecond Laser Pulses", *Thesis for Dept. of Physics*, Harvard University, May 2002, pp. 1-74.
Dausinger, Friedrich et al., "Micro-machining with ultrashort laser pulses: From basic understanding to technical applications", publisher unknown, undated but prior to Jul. 2009, pp. 1-10.
Dholakia, Sheena A. et al., "Prospective evaluation of phacoemulsification in adults younger than 50 years", *J Cataract Refract Surg*, vol. 31, 2005, pp. 1327-1333.
Douven, Lucien F.A. et al., "Characterization of Mechanical Behaviour of Human Skin In Vivo", *Proc. of SPIE*, vol. 3914, 2000, pp. 618-629.
Du, D. et al., "Laser-induced breakdown by impact ionization in $SiO_2$ with pulse widths from 7 ns to 150 fs", *Appl. Phys. Lett.*, vol. 64, No. 23, Jun. 6, 1994, pp. 3071-3073.
Ehrmann, Klaus et al., "Evaluation of porcine crystalline lenses in comparison with molded polymer gel lenses with an improved ex vivo accommodation simulator", *Proc. of SPIE*, vol. 5688, 2005, pp. 240-251.
Ehrmann, Klaus et al., "Ex Vivo Accommodation Simulator II—Concept and Preliminary Results", *Proc. of SPIE*, vol. 5314, 2004, pp. 48-58.
Eisner, Georg, "Eye Surgery—An Introduction to operative technique", Springer-Verlag, Berlin, 1980, pp. 14-19.
Ei-Osta, Austen A.R. et al., "In vitro model for the study of human posterior capsule opacification", *J Cataract Refract Surg*, vol. 29, 2003, pp. 1593-1600.

(56) References Cited

OTHER PUBLICATIONS

Erpelding, Todd N. et al., "Bubble-Based Acoustic Radiation Force for Monitoring Intraocular Lens Elasticity", *IEEE Intl Ultrasonics Symposium*, volume unknown, 2004, pp. 732-735.
Fagerholm, Per P.P., "The Response of the Lens to Trauma", *Trans. Ophtal. Soc. U. K.*, 1982, vol. 102, p. 369-374.
Farnsworth, P.N. et al., "Anterior Zonular Shifts with Age", *Exp. Eye Res.*, vol. 28, 1979, pp. 291-297.
Findl, Oliver et al., "Laserinterferometric Assessment of Pilocarpine-Induced Movement of an Accommodating Intraocular Lens—A Randomized Trial", *Ophthalmology*, vol. 111, No. 8, Aug. 2004, pp. 1515-1521.
Fisher, R.F. et al., "Changes in lens fibres after damage to the lens capsule", publisher unknown, undated but prior to Jul. 2009, 4 pgs.
Fisher, R.F., "Elastic Constants of the Human Lens Capsule", *J. Physiol.*, vol. 201, 1969, pp. 1-19.
Fisher, R.F., "Presbyopia and the Changes With Age in the Human Crystalline Lens", *J. Physiol.*, vol. 228, 1973, pp. 765-779.
Fisher, R. F., "The Ciliary Body in Accommodation", *Trans. Opthalmol. Soc. U.K.*, vol. 105, 1986, pp. 208-219.
Fisher, R.F., "The Elastic Constants of the Human Lens", *J. Physiol.*, vol. 212, 1971, pp. 147-180.
Fisher, R. F. et al., "The elastic constants and ultrastructural organization of a basement membrane (lens capsule)", *Proc. R. Soc. Lond. B.*, vol. 193, 1976, pp. 335-358.
Fisher, R.F., "The Force of Contraction of the Human Ciliary Muscle During Accommodation", *J. Physiol.*, vol. 270, 1977, pp. 51-74.
Fisher, R. F., "The Mechanics of Accommodation in Relation to Presbyopia", *Eye*, vol. 2, 1988, pp. 646-649.
Fleck, Brian W. et al., "Q-switched Nd:YAG laser disruption of rabbit lens nucleus", *Laser and Light in Ophthalmology*, 1990, vol. 3. No. 3, pp. 227-232.
Foster, C. Stephen et al., "Smolin and Thoft's The Cornea: Scientific Foundations and Clinical Practice", *The New England Journal of Medicine*, vol. 353 No. 23, 2005, pp. 2519-2520.
Fujimoto, James et al., "Biomedical Optics", Photonics West, *Proc. of SPIE*, volume unknown, 2005, pp. 23-70.
Garner, LF et al., "Changes in Equivalent and Gradient Refractive Index of the Crystalline Lens with Accommodation", *Optom, Vis. Sci.*, vol. 74, No. 2, Feb. 1997, pp. 114-119.
Garner, LF et al., "Changes in Ocular Dimensions and Refraction with Accommodation", *Ophthal. Physiol. Opt.*, vol. 17, No. 1, 1997, pp. 12-17.
Garner, Margaret H. et al., "Selective oxidation of cysteine and methionine in normal and senile cataractous lenses", *Proc. Natl. Acad. Sci. USA*, vol. 77, No. 3, Mar. 1980, pp. 1274-1277.
Gayen, Tapan K. et al., "Near-infrared laser welding of aortic and skin tissues and microscopic investigation of welding efficacy", *Proc. of SPIE*, vol. 4949, 2003, pp. 182-185.
Gershenzon, A. et al., "Clinical and Epidemiology—New software for lens retro-illumination digital image analysis", *Australian and New Zealand Journal of Ophthalmology*, 1999, vol. 27, pp. 170-172.
Giblin, Frank J. et al., "Nuclear Light Scattering, Disulfide Formation and Membrane Damage in Lenses of Older Guinea Pigs Treated with Hyperbaric Oxygen", *Exp. Eye Res.*, 1995, vol. 60, pp. 219-235.
Gills, James P., "Treating astigmatism at the time of cataract surgery", *Current Opinion in Ophthalmology*, 2002, vol. 13, p. 2-6.
Gimbel, Howard V. et al., "Intrastromal Photorefractive Keratectomy with the Nd:YLF Laser", publisher unknown, vol. 34, Iss. 4, 1994, pp. 139-145.
Glasser, Adrian et al., "Accommodative Changes in Lens Diameter in Rhesus Monkeys", *IOVS*, vol. 47, No. 1, Jan. 2006, pp. 278-286.
Glasser, A. et al., "Biometric, optical and physical changes in the isolated human crystalline lens with age in relation to presbyopia", *Vision Research*, vol. 39, 1999, pp. 1991-2015.
Glasser, Adrian et al., "On modeling the causes of presbyopia", *Vision Research*, vol. 41, 2001, pp. 3083-3087.
Glasser, A. et al., "On the potential causes of presbyopia", *Vision Research*, vol. 39, 1999, pp. 1267-1272.
Glasser, Adrian et al., "Presbyopia and the Optical Changes in the Human Crystalline Lens with Age", *Vision Res.*, vol. 38, No. 2, 1998, pp. 209-229.
Glasser, Adrian et al., "Ultrasound Biomicroscopy of the Aging Rhesus Monkey Ciliary Region", *Optometry and Vision Science*, vol. 78, No. 6, 2001, pp. 417-424.
Goodenough, Daniel A., "Lens gap junctions: a structural hypothesis for nonregulated low-resistance intercellular pathways", *Invest. Ophthalmol. Visual Sci.*, vol. 18, No. 11, Nov. 1979, pp. 1104-1122.
Grace, Jeffery M. et al., "Repetitively Pulsed Ruby Lasers As Light Sources for High-Speed Photography", *Optical Engineering*, vol. 37, No. 8, Aug. 1998, pp. 1-26.
Gwon, Arlene et al., "Focal laser photophacoablation of normal and cataractous lenses in rabbits: Preliminary report", *J Cataract Refract Surg*, vol. 21, May 1995, pp. 282-286.
Habib, Maged S. et al., "Myopic Intrastromal Photorefractive Keratectomy With the Neodymium-Yttrium Lithium Fluoride Picosecond Laser in the Cat Cornea", *Arch Ophthalmol.*, vol. 113, Apr. 1995, pp. 499-505.
Hahn, D.W., "Dynamics of Ablation Plume Particles Generated During Excimer Laser Corneal Ablation", *Lasers in Surgery and Medicine*, vol. 16, 1995, pp. 384-389.
Hamaoui, Marie et al., "Ex-vivo testing of crystalline lens substitutes: a pilot study", *Proc. of SPIE*, vol. 3908, 2000, pp. 123-130.
Hammer, Daniel X. et al., "Dual OCT/SLO Imager with Three-Dimensional Tracker", *Proc. of SPIE*, vol. 5688, 2005, pp. 33-44.
Hammer, Daniel et al., "Shielding Properties of Laser-Induced Breakdown in Water for Pulse Durations From 5 ns to 125 fs", *Applied Optics*, 1997, vol. 36, No. 22, pp. 5630-5640.
Hanson, S.R.A. et al., "The major in vivo modifications of the human water-insoluble lens crystallins are disulfide bonds, deamidation, methionine oxidation and backbone cleavage", *Exp. Eye Res.*, vol. 71, 2000, pp. 195-207.
Hara, Tsutomu, M.D. et al., "Complications associated with endocapsular balloon implantation rabbit eyes", *J Cataract Refract Surg*, vol. 20, Sep. 1994, pp. 507 and 512.
Harding, J. J., "Disulphide Cross-linked Protein of High Molecular Weight in Human Cataractous Lens", *Exp. Eye Res.* (1973), vol. 17, pp. 377-383.
Hartwick, Andrew T. E. et al., "Ephitelial activity of hexokinase and glucose-6-phosphate dehydrogenase in cultured bovine lenses recovering from pharmaceutical-induced optical damage", *Molecular Vision*, vol. 9, 2003, pp. 594-600.
Heisterkamp, Alexander et al., "Nonlinear effects inside corneal tissue after fs-photodisruption", *Proc. of SPIE*, vol. 4433, 2001, pp. 55-60.
Heisterkamp, Alexander et al., "Pulse energy dependence of subcellular dissection by femtosecond laser pulses", *Optics Express*, vol. 13, No. 10, May 2005, pp. 3690-3696.
Hemenger, Richard P. et al., "Change With Age of the Refractive Index Gradient of the Human Ocular Lens", *Investigative Ophthalmology & Visual Science*, Mar. 1995. vol. 36, No. 3. pp. 703-707.
Heys, Karl Robert et al., "Massive increase in the stiffness of the human lens nucleus with age: the basis for presbyopia?", *Molecular Vision*, vol. 10, 2004, pp. 956-963.
Ho, A. et al., "Feasibility of simultaneous correction of ametropia by varying gel refractive index with phaco-ersatz", *Proc. of SPIE*, vol. 4245, 2001, pp. 119-128.
Hoffman, Richard S. et al., "Refractive lens exchange as a refractive surgery modality", Copyright© 2004 Lippincott Williams & Wilkins, pp. 22-28.
Holzer, Mike P. et al., "Corneal flap complications in refractive surgery—Part 1: Development of an experimental animal model", *J Cataract Refract Surg*, vol. 29, Apr. 2003, pp. 795-802.
Holzer, Mike P. et al., "Corneal flap complications in refractive surgery—Part 2: Postoperative treatments of diffuse lamellar keratitis in an experimental animal model", *J Cataract Refract Surg*, vol. 29, Apr. 2003, pp. 803-807.
Horwitz, Joseph, "α-Crystallin can function as a molecular chaperone", *Proc. Natl. Acad. Sci. USA*, vol. 89. Nov. 1992, pp. 10449-10453.

(56) References Cited

OTHER PUBLICATIONS

Hu, Tian-Sheng et al., "Reversal of Galactose Cataract with Sorbinil in Rats", *Investigative Ophthalmology & Visual Science*, May 1983, vol. 24, pp. 640-644.

Huber, G. et al., "Room-temperature 2-pm HO:YAG and 3-µm ER:YAG Lasers", *Journal de Physique*, undated but prior to Jul. 2009, 3 pgs.

Hunter, David, "First, Gather the Data", *New England Journal of Medicine*, vol. 354, No. 4, Jan. 26, 2006, pp. 329-331.

Jacques, Paul F. et al., "Long-term vitamin C supplement use and prevalence of early age-related lens opacities", *Am J Clin Nutr*, 1997; 66, pp. 911-916.

Johannesson, Mattias, "Active Range Imaging 2", PhD-Thesis: SIMD architectures for Range and Radar Imaging, *Linkoping Studies in Science and Technology*, Dissertations No. 399, 2005, pp. 1-34.

Jones, C.E. et al., "Refractive index distribution and optical properties of the isolated human lens measured using magnetic resonance imaging (MRI)", *Vision Research*, vol. 45, 2005, pp. 2352-2366.

Juhasz, Tibor, Ph.D. et al., "Dynamics of Shock Waves and Cavitation Bubbles Generated by Picosecond Laser Pulses in Corneal Tissue and Water", *Lasers in Surgery and Medicine*, vol. 15, 1994, pp. 91-98.

Juhasz, T. et al., "Time resolved observations of shock waves and cavitatin bubbles generated by femtosecond laser pulses in corneal tissue and water", *Lasers in Surgery and Med*, vol. 19, 1996, pp. 23-31.

Juhasz, T. et al., "Time-resolved Studies of Plasma-Mediated Surface Ablation of Soft Biological Tissue with Near-Infrared Picosecond Laser Pulses", *SPIE*, vol. 2975, 1997, pp. 271-281.

Kasthurirangan, Sanjeev et al., "Amplitude dependent accommodative dynamics in humans", *Vision Research*, vol. 43, 2003, pp. 2945-2956.

Kasthurirangan, Sanjeev, "Influence of Amplitude and Starting Point on Accommodative Dynamics in Humans", *IOVS*, vol. 46, No. 9, Sep. 2005, pp. 3463-3472.

Kaufman, Paul L., M.D., "Accommodation and Presbyopia: Neuromuscular and Biophysical Aspects", *Adler's Physiology of the Eye*, date unknown but prior to Jul. 2009, pp. 391-411.

Klem, D. E. et al., "The Interaction of Intense Femtosecond Laser Pulses with Solid Targets", paper prepared under the auspices of the U.S. Dept. of Energy for the Short Wavelength V: Physics with Intense Laser Pulses Second Topical Meeting on Mar. 29-31, published Dec. 30, 1992, 1993, 6 pgs.

Keeney, Arthur H., M.D., "Intralenticular Foreign Bodies", *Arch Ophthal.*, vol. 86, Nov. 1971, pp. 499-501.

König, Karsten et al., "Are Femtosecond Lasers Safe for Ophthalmic Applications?", *Fraunhofer Institute of Biomedical Technologies*, undated but prior to Jul. 2009, pp. 1-16.

König, Karsten et al., "Cornea surgery with nanojoule femtosecond laser pulses", *Proc. of SPIE*, vol. 5688, 2005, pp. 288-293.

König, Karsten et al., "First in vivo animal studies on intraocular nanosurgery and multiphoton tomography with low-energy 80 MHz near infrared femtosecond laser pulses", *Proc. of SPIE*, vol. 5314, 2004, pp. 262-269.

Koopmans, Steven A. et al., "Polymer Refilling of Presbyopic Human Lenses In Vitro Restores the Ability to Undergo Accommodative Changes", *IOVS*, vol. 44, No. 1, Jan. 2003, pp. 250-257.

Koretz, Jane F. et al., "A Model for Accommodation in The Young Human Eye: The Effects of Lens Elastic Anisotropy on the Mechanism", *Vision Res.*, vol. 23, No. 12, 1983, pp. 1679-1686.

Koretz, Jane F. et al., "Accommodation and Presbyopia in The Human Eye—Aging of the Anterior Segment", *Vision Res.*, vol. 29, No. 12, 1989, pp. 1685-1692.

Koretz, Jane F. et al., "Accommodation and Presbyopia in the Human Eye—Changes in the Anterior Segment and Crystalline Lens With Focus", *IOVS*, vol. 38, No. 3, Mar. 1997, pp. 569-578.

Koretz, Jane F. et al., "Analysis of Human Crystalline Lens Curvature as a Function of Accommodative State and Age", *Vision Res.*, vol. 24, No. 10, 1984, pp. 1141-1151.

Koretz, Jane F. et al., "How the Human Eye Focuses", *Scientific American*, Jul. 1988, pp. 92-99.

Koretz, Jane F. et al., "Model of the Accommodative Mechanism in The Human Eye", *Vis. Res.*, vol. 22, 1982, pp. 917-927.

Koretz, Jane F. et al., "Scheimpflug and high-resolution magnetic resonance imaging of the anterior segment: a comparative study", *J. Opt. Soc. Am. A*, vol. 21, No. 3, Mar. 2004, pp. 346-354.

Koretz, Jane F. et al., "The Zones of Discontinuity in the Human Lens: Development and Distribution with Age", *Vision Res.*, vol. 34, No. 22, 1994, pp. 2955-2962.

Krag, Susanne et al., "Biomechanical Characteristics of the Human Anterior Lens Capsule in Relation to Age", *Investigative Ophthalmology & Visual Science*, vol. 38, No. 2, Feb. 1997, pp. 357-362.

Krag, Susanne, "Biomechanical measurements of the lens capsule", *Scandinavian University Theses*, 1999, 3 pgs.

Krag, Susanne et al., "Mechanical Properties of the Human Posterior Lens Capsule", *IOVS*, vol. 44, No. 2, 2003, pp. 691-696.

Krauss, Joel et al., "Laser Interactions With the Cornea", *Survey of Ophthalmology A687*, vol. 31, No. 1, Jul./Aug. 1986, pp. 37-53.

Kronemyer, Bob, "Accommodating IOL? Impossible, Recent Study Seems to Say". *Ocular Surgery News*, http://www.slackmc.com, Sep. 15, 1996, 2 pgs.

Krueger, Ronald R. et al., "Experimental Increase in Accommodative Potential after Neodymium: Yttrium-Aluminum-Garnet Laser Photodisruption of Paired Cadaver Lenses", *Ophthalmology*, vol. 108, No. 11, 2001, pp. 2122-2129.

Krueger, Ronald R. et al., "First safety study of femtosecond laser photodisruption in animal lenses: Tissue morphology and cataractogenesis", *J Cataract Refract Surg*, vol. 31, Dec. 2005, pp. 2386-2394.

Krueger, Ronald R., M.D., et al., "Nonmechanical Microkeratomes Using Laser and Water Jet Technology", Publisher unknown, date unknown but prior to Jul. 2009, pp. 1-33.

Krueger, R.R., "Surf's Up—Catch a wave with a waterjet", *Jrn. Ref. Surg.*, vol. 14, No. 3, May/Jun. 1998, pp. 280-281.

Krueger, Ronald R., M.D. et al., "Ultrastructure of Picosecond Laser Intrastromal Photodisruption", *Journal of Retractive Surgery*, vol. 12, Jul./Aug. 1996, pp. 607-612.

Kuizenga, Dirk J., "FM-Laser Operation of the Nd:YAG Laser", *IEEE Journal of Quantum Electronics*, vol. 6, No. 11, 1970, pp. 673-677.

Kurapkienė, S. et al., "The relationship of ultrasonic and mechanical properties of human nuclear cataract. A pilot study", *Ultragarsas*, vol. 54, No. 1, 2005, pp. 39-43.

Kurtz, Ron et al., "Femtosecond Laser Corneal Refractive Surgery", *Proc. of SPIE*, vol. 3591, 1999, pp. 209-219.

Kurtz, Ron et al., "Ophthalmic Applications of Femtosecond Lasers", *Proc. f SPIE*, vol. 3616, 1999, pp. 51-65.

Kurtz, Ron M. et al., "Optimal Laser Parameters for Intrastromal Corneal Surgery", *Proc. of SPIE*, vol. 3255, 1998, pp. 56-66.

Kurtz, Ron M., MD, et al., "Photo-disruption in the Human Cornea as a Function of Laser Pulse Width", *Journal of Refractive Surgery*, vol. 13, Nov./Dec. 1997, pp. 653-658.

Kuszak, J. R. et al., "A Quantitative Analysis of Sutural Contributions to Variability in Back Vertex Distance and Transmittance in Rabbit Lenses as a Function of Development, Growth, and Age", *Optometry and Vision Science*, vol. 79, No. 3, Mar. 2002, pp. 193-204.

Kuszak, J. R. et al., "Anatomy of Aged and Senile Cataractous Lenses", from "Biochemistry of The Crystalline Lens", undated but prior to Jul. 2009, pp. 564-575.

Kuszak, J. R. et al., "Biochemistry of The Crystalline Lens; Anatomy of Aged and Senile Cataractous Lenses", pp. 564-575.

Kuszak, J. R. et al., "Development of lens sutures", *Int. J. Dev. Biol.*, vol. 48, 2004, pp. 889-902.

Kuszak, J. R. et al., "Electron Microscope Observations of the Crystalline Lens", *Microscopy Research and Technique*, 1996, vol. 33, pp. 441-479.

Kuszak, J. R. et al., "Fibre cell organization in crystalline lenses", *Experimental Eye Research*, vol. 78, 2004, pp. 673-687.

Kuszak, J. et al., "Gap Junctions of Chick Lens Fiber Cells", *Exp. Eye Res.*, vol. 27, 1978, pp. 495-498.

(56) References Cited

OTHER PUBLICATIONS

Kuszak, J. R. et al., "Lens Optical Quality and Lens Sutures", *Investigative Ophthalmology & Visual Science*, vol. 32, No. 7, Jun. 1991, pp. 2123-2129.
Kuszak, J. R. et al., "Lens Optical Quality is a Direct Function of Lens Sutural Architecture", *Investigative Ophthalmology & Visual Science*, vol. 32, No. 7, Jun. 1991, pp. 2119-2129.
Kuszak, J. R. et al., "Quantitative Analysis of Animal Model Lens Anatomy: Accommodative Range is Related to Fiber Structure and Organization", undated but prior to Jul. 2009, 26 pgs.
Kuszak, J. R. et al., "Suppression of Post-Vitrectomy Lens Changes in the Rabbit by Novel Benzopyranyl Esters and Amides", *Exp. Eye Res.*, vol. 75, 2002, pp. 459-473.
Kuszak, JR et al., "The interrelationship of lens anatomy and optical quality II Primate Lenses", *Exp. Eye Res.*, vol. 59, 1994, pp. 521-535.
Kuszak, J. R. et al., "The Relationship Between Rabbit Lens Optical Quality and Sutural Anatomy after Vitrectomy", *Exp. Eye Res.*, vol. 71, 2000, pp. 267-281.
Kuszak Jer R. et al., "The Structure of the Vertebrate Lens", Chapter 4, undated but prior to Jul. 2009, pp. 71-118.
Kuszak, J. et al., "The Surface Morphology of Embryonic and Adult Chick Lens-Fiber Cells", *The American Journal of Anatomy*, vol. 159, 1982, pp. 395-410.
Kuszak, J. R. et al., "The Use of an Ex Vivo Mechanical Stretching Apparatus to Examine Fiber Ultrastructure During Accommodation", undated but prior to Jul. 2009, 1 pg.
Kuwabara, Toichiro, et al., "Electron Microscopic Study of Galactose-Induced Cataract", *Investigative Ophthalmology*, vol. 8, No. 2, Apr. 1969, pp. 133-149.
L'Esperance, Jr. "Ophthalmic Lasers Photocoagulation, Photoradiation and Surgery", $2^{nd}$ Edition, The C.V. Mosby Company, copyright 1983, pp. 529-538.
Lerman, Sidney, et al., "A Method for Detecting 8-Methoxypsoralen in the Ocular Lens", *Science*, vol. 197, Sep. 23, 1977, 1287-1288.
Lerman, Sidney, et al., "Photosensitization of the lens by 8-methoxypsoralen", *Invent. Ophthalmol. Visual Sci.*, vol. 16, No. 11, Nov. 1977, pp. 1065-1068.
Lerman, Sidney, M.D., "Photosensitizing Drugs and Their Possible Role in Enhancing Ocular Toxicity", *Ophthalmology*, vol. 93, No. 3, Mar. 1986, pp. 304-318.
Lerman, Sidney, et al., "Psoralen-long-wave Ultraviolet Therapy and Human Cataractogenesis", *Invent. Ophthalmol. Visual Sci.*, vol. 23, No. 6, Dec. 1982, pp. 801-804.
Lerman, Sidney, et al., "Spectroscopic Evaluation and Classification of the Normal, Aging, and Cataractous Lens", *Ophthl. Res.*, vol. 8, 1976, pp. 335-353.
Lim, Seung Jeong, M.D. et al., "Analysis of zonular-free zone and lens size in relation to axial length of eye with age", *J Cataract Refract Surg*, vol. 24, Mar. 1998, pp. 390-396.
Liu, X. et al., "Competition between Ponderomotive abd Thermal Forces in Short-Scale-Length Laser Plasmas", *Physical Review Letters*, vol. 69, No. 13, Sep. 28, 1992, pp. 1935-1938.
Liu, Xinbing et al., "In vivo plasma-mediated ablation as a function of laser pulse width", *SPIE*, vol. 2975, 1997, pp. 282-288.
Loerscher, Hanspeter et al., "Noncontact Trephination of the Cornea Using a Pulsed Hydrogen Floride Laser", *American Journal of Ophthalmology*, vol. 104, Nov. 1987, pp. 471-475.
Loesel, Frieder H. et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.
Lou, Marjorie F., et al., "Protein-Thiol Mixed Disulfides in Human Lens", published by Academic Press Limited, 1992, pp. 889-896.
Lubatschowski, Holger, "Surgical Laser System for the Treatment of Presbyopia", $7^{th}$ *Biotech in Europe Investor Forum*, Switzerland, Oct. 2-3, 2007, 9 pgs.
Lutze, Margaret et al., "Lenses of Diabetic Patients "Yellow" at an Accelerated Rate Similar to Older Normals", *Investigative Ophthalmology & Visual Science*, vol. 32, No. 1, Jan. 1991, pp. 194-199.

Maguen, Ezra, et al., "Excimer Laser Ablation of the Human Lens at 308 nm with a Fiber Delivery System", *J. Cataract Refract Surg.*, vol. 15, Jul. 1989, pp. 409-414.
Manns, Fabrice et al., "Radius of Curvature and Aspericity of the Anterior and Posterior Surface of Human Cadaver Crystalline Lenses", *Experimental Eye Research*, 2004, vol. 78, pp. 39-51.
Marion, II, John E. et al., "Medical Applications of Ultra-Short Pulse Lasers", *Proc. of SPIE*, vol. 3616, 1999, pp. 42-50.
Masters, B.R., "Three-dimensional Microscopic Tomographic Imaging of the Cataract in a Human Lens In Vivo", *Optics Express* 332, vol. 3, No. 9, Oct. 1998, pp. 332-338.
Mathias, R.T. et al., "Physiological Properties of the Normal Lens", *Physiological Reviews*, vol. 77, No. 1, Jan. 1997, pp. 21-50.
McBrien, N. A et al., "Experimental Myopia in a Diurnal Mammal (Sciurus Carolinesis) with No Accommodative Ability", *J. Physiol.*, vol. 469, 1993, pp. 427-441.
McCourt, M. E et al., Refractive State, Depth of Focus, and Accommodation of the Eye of the California ground squirrel (Spermophiliu Beecheyi), *Vision Res*, vol. 24, No. 10, 1984, pp. 1261-1266.
McDonald, Marguerite B., et al., "Central Photorefractive Keratectomy for Myopia, The Blind Eye Study", *Arch Ophthalmol*, vol. 108, Jun. 1990, pp. 799-808.
Michael, Ralph et al., "Refractive Index of Lens Fiber Membranes in Different Parts of the Crystalline Lens", *Proceedings of SPIE*, vol. 4611, 2002, pp. 159-164.
Moffat, B.A. et al., "Age-Related Changes in Refractive Index Distribution and Power of the Human Lens as Measured by Magnetic Resonance Micro-Imaging In Vitro", *Vision Research*, vol. 42, 2002, pp. 1683-1693.
Müller, F. et al., "A Comparative Study of Deposition of Thin Films by Laser Induced PVD with Femtosecond and Nanosecond Laser Pulses", *SPIE*, vol. 1858, 1993, pp. 464-474.
Mutti, Donald O., et al., "A Video Technique for Phakometry of the Human Crystalline Lens", *Investigative Ophthalmology, & Visual Science*, vol. 33, No. 5, Apr. 1992, pp. 1771-1781.
Myers, Raymond I. et al., "Feasibility of Using Lasers to Retard Cataract Development in the Ocular Lens by Restoring Lens Movement"; undated but prior to Jul. 2009, pp. 1-22.
Myers, Raymond I. et al., "Novel Approaches to Correction of Presbyopia With Laser Modification of the Crystalline Lens", *Journal of Refractive Surgery*, vol. 14, Mar./Apr. 1998; pp. 136-139.
Nanevicz, Tania M., et al., "Excimer Laser Ablation of the Lens", *Arch Ophthamol*, vol. 104, Dec. 1986, pp. 1825-1829.
Naranjo-Tackman, Ramon et al., "Subepithelial arquate (sic) incisions, using the femtosecond surgical laser, in post-phaco astigmatism: Preliminary visual and refractive results", a powerpoint presentation shown at ESCRS meeting held in London England in Sep. 2006, 8 pgs.
Neev, Joseph, "Ultrashort Pulse Lasers: A New Tool for Biomedical Applications", *SPIE*, vol. 3255; pp. 2-7.
Nichamin, Louis D., "Treating astigmatism at the time of cataract surgery", *Current Opinion in Ophthalmology*, 2003, vol. 14, p. 35-38.
Oberheide, Uwe et al., "Therapy Monitoring of Laser Cyclophotocoagulation", *Proceedings of SPIE*, vol. 4611, 2002, pp. 48-53.
O'Donnell, Colleen B., et al., "Ablation Smoothness as a Function of Excimer Laser Delivery System", *J. Cataract Refract Surg.*, vol. 22, Jul./Aug. 1996, pp. 682-685.
O'Donnell, Colleen B., et al., "Surface Roughness in PMMA is Linearly Related to the Amount of Excimer Laser Ablation", *Journal of Refractive Surgery*, vol. 12, Jan./Feb. 1996, pp. 171-174.
Oriowo, Olanrewaju Matthew, "A Study of Ultraviolet Radiation Effects on Procine Crystalline Lens and Development of a New Assay Methodology for UV Cataractogenesis Investigation", *A Thesis Presented to the University of Waterloo*, 2000, pp. i-xix and 1-218.
Ostrin, Lisa A. et al., "Comparisons Between Pharmacologically and Edinger-WestphalStimulated Accommodation in Rhesus Monkeys", *Investigative Ophthalmology & Visual Science*, 2005, vol. 46, No. 2, pp. 609-617.
Ostrin, Lisa A. et al., "Effects of Pirenzepine on Pupil Size and Accommodation in Rhesus Monkeys", *Investigative Ophthalmology & Visual Science*, Oct. 2004, vol. 45, No. 10, pp. 3620-3628.

(56) References Cited

OTHER PUBLICATIONS

Ostrin, Lisa A. et al., "The Effects of Phenylephrine on Pupil Diameter and Accommodation in Rhesus Monkeys"; *Investigative Ophthalmology & Visual Science*, 2004, vol. 45, No. 1, pp. 215-221.
Parel, Jean-Marie et al., "Intraocular Implants for The Surgical Correction of Presbyopia"; *In Ophthalmic Technologies X*, Proceedings of SPIE, vol. 3908, 2000, pp. 115-122.
Patel, C.K. et al., "The Ageing Lens", *Association of Optometrists, City University, London*; undated, www.optometry.co.uk; pp. 27-31.
Pau, Hans et al., "The increasing sclerosis of the human lens with age and its relevance to accommodation and presbyopia", *Graefe's Arch Clin Exp. Ophthalmol.*, (1991) vol. 229, pp. 294-296.
Payne, Peter A. et al., "Ophthalmic Applications of Laser-Generated Ultrasound"; *SPIE*, 2000, vol. 3908, pp. 13-22.
Peterson, Jennifer A. et al., "Intraocular Pressure Measurement in Cynomolgus Monkeys, Tono-Pen Versus Manometry", *Investigative Ophthalmology & Visual Science*, 1996, vol. 37, No. 6, pp. 1197-1199.
Prokofeva, G. I et al., "Effects of Low-Intensity Infrared Laser Irradiation on the Eye, (An Experimental Study)", *Vestn. Oftalmol.*, vol. 112, No. 1, 1996, pp. 31-32, with English Abstract, 5 pgs.
Puliafito, Carmen A., M.D. et al., "High-Speed Photography of Excimer Laser Ablatio of the Cornea", *Arch Ophthalmol*, vol. 105, Sep. 1987, pp. 1255-1259.
Qian, Wen et al., "3 Year Simvastatin Treatment and Lens Nuclear Back Scattering"; *J Ophthalmol*, vol. 84, 2000, pp. 512-516.
Qian, Wen et al., "Universal Opacity Standard for Scheimpflug Photography", *Ophthalmic Res*, 2000, vol. 32, pp. 292-298.
Rafferty, Nancy et al., "Lens Wound Healing and Cataractogenesis in a Pigmented Eye", *Exp. Eye Res.* (1984), vol. 38, pp. 267-277.
Riley, Michael V., et al., "The Effects of UV-B Irradiation on the Corneal Endothelium", *Eye Research Institute of Oakland University*, 1987, pp. 1021-1033.
Ripken, T. et al., "FEM Simulation of the Human Lens Compared to Ex-Vivo Porcine Lens Cutting Pattern: A Possible Treatment of Presbyopia"; undated, 11 pgs.
Ripken T. et al., "First in-vivo studies of Presbyopia treatment with ultrashort laser pulses", *Proc. SPIE* 5142, vol. 137, 2003, 9 pgs.
Ripken, T. et al., "Fs-laser Induced Elasticity Changes to Improve Presbyopic Lens Accommodation", undated, 10 pgs.
Ripken T. et al., "Investigations for the correction of Presbyopia by fs-laser induced cuts", *Proc. SPIE* 5314, vol. 27, 2004, 9 pgs.
Rockwell, B.A. et al., "Safe Use of Ultra-short Lasers"; *SPIE*, vol. 3616, 1999, pp. 32-39.
Roesner, C.A.D. et al., "Light-Matter Interactions on the Femtosecond Time Scale", *Department of Physics and Division of Engineering and Applied Sciences, Harvard University*; undated, pp. 1-27.
Rol, Pascal et al., "An Optomechanical Eye Model for Observation of Lens Photoablation"; *SPIE*, 1997, vol. 2971, pp. 171-174.
Sacks, Zachary S. et al., "Laser Spot Size as a Function of Tissue Depth and Laser Wavelength in Human Sclera", *SPIE*, 1998, vol. 3255, pp. 67-76.
Sauteret, C. et al., "Laser designers eye petawatt power", *Laser Focus World*, Oct. 1990, pp. 85-92 with cover page.
Scammon, Richard J. et al., "Simulations of Shock Waves and Cavitation Bubbles Produced in Water by Picosecond and Nanosecond Laser Pulses", *SPIE*, 1998, vol. 3254, pp. 264-275.
Schachar, Ronald A. MD, PhD., et al., "A Revolutionary Variable Focus Lens", *Annals of Ophthalmology*, vol. 28, No. 1, Jan./Feb. 1996, pp. 11-18.
Schachar, Ronald A., M.D., "Cause and Treatment of Presbyopia With a Method for Increasing the Amplitude of Accommodation", *Annals of Ophthalmol*, 1992, vol. 24, pp. 445-452.
Schachar, Ronald A., M.D. et al., "Experimental Destruction of Cataractous Lenses by Laser", *Ophthalmic Surgery*, Surgical Forum, pp. 506-509.
Schachar, Ronald A., M.D. et al., "Experimental Support for Schachar's Hypothesis of Accommodation", *Ann Ophthalmol*, 1993; vol. 25, pp. 404-409.
Schachar, Ronald A., MD, PhD, "Histology of the Ciliary Muscle-Zonular Connections", *Annals of Ophthalmology*, vol. 28, No. 2, Mar./Apr. 1996, pp. 70-79.
Schachar, Ronald A. MD et al., "Mechanism of Human Accommodation as Analyzed by Nonlinear Finite Element Analysis", *Ann Ophthalmol*; 2001; vol. 33, No. 2, pp. 103-112.
Schachar, Ronald A., MD, PhD, "Pathophysiology of Accommodation and Presbyopia, Understanding the Clinical Implications", *J. Florida M.A.*, vol. 81, No. 4, Apr. 1994, pp. 268-271.
Schaeffel, Frank, "Kappa and Hirschberg Ratio Measured With an Automated Video Gaze Tracker", *Optometry and Vision Science*, 2002, vol. 79, No. 5, pp. 329-334.
Schaffer, Chris B. et al., "Dynamics of Femtosecond Laser-Induced Breakdown in Water From Femtoseconds to Microseconds", *Optics Express*, 2002, vol. 10, No. 3, pp. 196-203.
Schaffer, Chris B. et al., "Morphology of Femtosecond Laser-Induced Structural Changes in Bulk Transparent Materials", *Applied Physics Letters*, vol. 84, No. 9, 2004, pp. 1441-1443.
Shen, Nan, et al., "Ablation of Cytoskeletal Filaments and Mitochondria In Live Cells Using a Femtosecond Laser Nanoscissor", *MCB*, 2005, vol. 2, No. 1, pp. 17-25.
Shen, Nan; "Photodisruption in Biological Tissues Using Femtosecond Laser Pulses", *A Thesis Presented to the Department of Physics*, Harvard University, 2003, pp. 1-125.
Shen, Nan, et al., "Photodisruption in Biological Tissues and Single Cells Using Femtosecond Laser Pulses", undated, 2 pgs.
Shen, Nan, et al., "Surface and Bulk Photodisruption in Turbid Tissue Using Femtosecond Laser Pulses", *Department of Physics and Division of Engineering and Applied Sciences, Harvard University* undated, pp. 1-24.
Sher, Neal A., MD, "Hyperopic Refractive Surgery", *Current Opinion in Ophthalmology*, 2001, vol. 12, pp. 304-308.
Sivak, Jacob G., "Through the Lens Clearly: Phylogeny and Development, The Proctor Lecture", *Ophthalmology & Visual Science*, 2004, vol. 45, No. 3, pp. 740-747.
Sliney, D. H et al., "Medical Lasers and Their Safe Use", *Springer Verlag*, New York, 1993, pp. 42-50.
Slingsby, Christine, "Lens Crystallin Crystal Structures", undated article, 3 pgs.
Söderberg, Per G., et al., "Angular Dependence of The Intensity of Back Scattered Light From Human Lenses With Nuclear Cataract, Implications for Measurement", *SPIE*, 2000, vol. 3908, pp. 34-37.
Söderberg, Per G., et al., "External Standard for Measurements with the Scheimpflug Slitlamp Microscope", *SPIE*, 1997, vol. 2971, pp. 8-13.
Soileau, M. J. et al., "Temporal Dependence of laser-Induced Breakdown in NaCl and Si02", prepared for Dept. of Physics, North Texas State University, publication date unknown, 19 pgs.
Solomon, Ira Seth, M.D., "Aqueous Humor Dynamics", undated, 17 pgs.
Spector, Abraham, "Aging of the Lens and Cataract Formation", *Aging and Human Visual Function*, pp. 27-43.
Srinivasan, R., "Ablation of Polymers and Biological Tissue by Ultraviolet Lasers", Oct. 1986, pp. 932-935.
Srinivasan R. et al., "Excimer Laser Surgery of the Cornea", *American Journal of Ophthalmology*, vol. 96, 1993, pp. 710-715.
Stitzel, Joel D., et al., "A Nonlinear Finite Element Model of the Eye With Experimental Validation for the Prediction of Globe Rupture", *Stapp Car Crash Journal*, 2002, vol. 45, 24 pgs.
Stitzel, Joel D., et al., "Blunt Trauma of the Aging Eye", *Arch Ophthalmol*, 2005, vol. 123, pp. 789-794.
Strauss, Moshe, et al., "Two-Dimensional Rayleigh Model of Vapor Bubble Evolution", *SPIE*, 1999, vol. 3601, pp. 212-224.
Strenk, Susan A., et al, "Age-Related Changes in Human Ciliary Muscle and Lens: A Magnetic Resonance Imaging Study", *Investigative Ophthalmology & Visual Science*, 1999, vol. 40, No. 6, pp. 1162-1169.
Strenk, Susan A. et al., "Magnetic Resonance Imaging Study of the Effects of Age and Accommodation on the Human Lens Cross-Sectional Area", *IOVS*, 2004, Vo. 45, No. 2, pp. 539-545.
Strenk, Susan A., et al, "The Mechanism of Presbyopia", *Progress in Retinal and Eye Research*, 2004 vol. 11, pp. 1-15.

(56) References Cited

OTHER PUBLICATIONS

Stuart, B. C. et al., "Laser-Induced Damage in Dielectrics with Nanosecond to Subpicosecond Pulses", *Physical Review Letters*, vol. 74, No. 12, Mar. 20, 1995, pp. 2248-2251.
Sweeney, Matthew H.J., et al., "Movement of Cysteine in Intact Monkey Lenses: The Major Site of Entry is the Germinative Region", *Experimental Eye Research*, 2003, vol. 77. pp. 245-251.
Swegmark, Gunnar, "Studies With Impedance Cyclography on Human Ocular Accommodation At Different Ages", *ACTA Ophthalmologica*, vol. 47, 1969, pp. 1186-1206.
Taboada, J., et al., "Optically Coupled Technique for Photorefractive Surgery of the Cornea", *Optics Letters*, vol. 15, No. 9, May 1, 1990, pp. 458-460.
Taboada, J. et al., "Response of the Corneal Epithelium to KrF Excimer Laser Pulses", *Health Physics*, vol. 30, 1981, pp. 677-683.
Tahi, Hassan, et al., "Restoring Accommodation: Surgical Technique and Preliminary Evaluation in Rabbits", *SPIE*, 1999, vol. 3591, pp. 267-269.
Tamm, Svenja, et al., "Age-Related Changes of the Human Ciliary Muscle. A Quantitative Morphometric Study", *Mechanisms of Aging and Development*, vol. 62, 1992, pp. 209-221.
Tang, Daxin; "Influence of Age, Diabetes, and Cataract on Calcium, Lipid-Calcium, and Protein-Calcium Relationships in Human Lenses", *Investigative Ophthalmology & Visual Science*, 2003, vol. 44, No. 5, pp. 2059-2066.
Taylor, Virginia L. et al., "Morphology of the Normal Human Lens", *Investigative Ophthalmology & Visual Science*, Jun. 1996, vol. 37, No. 7, pp. 1396-1410.
Topilow, Harvey W, M.D., "Vitreous Changes in Retinal Branch Vein Occlusion", *Arch Ophthalmol*, vol. 105, Sep. 1987, 2 pgs.
Trokel, Stephen L., M.D., et al., "Excimer Laser Surgery of the Cornea", *American Journal of Ophthalmology*, vol. 96, No. 6, Dec. 1983, pp. 710-715.
Tsai, Philbert S., "All-Optical, In-Situ Histology of Neuronal Tissue with Femtosecond Laser Pulses", *Imaging in Neuroscience and Development*, CSHL Press, undated, 12 pgs.
Tsubota, Kazuo, "Application of Erbium: Yag Laser in Ocular Ablation", *Ophthalmologica*, 1990, vol. 200, pp. 117-122.
Van Alphen, G.W.H.M. et al., "Elasticity of Tissues Involved in Accommodation", *Vision Res.*, vol. 31, No. 7/8, 1991, pp. 1417-1438.
Venugopalan, V. et al., "The Thermodynamic Response of Soft Biological Tissues to Ultraviolet Laser Irradiation", *Biophysical Journal*, vol. 60, Oct. 1995, pp. 1258-1271.
Vilupuru, Abhiram S., "Optical and Biometric Relationships of the Isolated Pig Crystalline Lens", *Ophthal. Physiol. Opt.*, 2001, vol. 21, No. 4, pp. 296-311.
Vilupuru, Abhiram S., "Spatially Variant Changes in Lens Power During Ocular Accommodation in a Rhesus Monkey Eye", *Journal of Vision*, 2004, vol. 4, pp. 299-309.
Vogel, Alfred et al., "Factors Determining the Refractive Effects of Intrastromal Photorefractive Keratectomy with the Picosecond Laser", *J. Cataract Refract Surg.*, vol. 23, Nov. 1997, pp. 1301-1310.
Vogel, Alfred et al., "Interaction of Laser-Produced Cavitation Bubbles With an Elastic Tissue Model", *SPIE*, 2001, vol. 4257, pp. 167-177.
Vogel, Alfred et al., "Intraocular Photodisruption With Picosecond and Nanosecond laser Pulses: Tissue Effects in Cornea, Lens and Retina", *Investigative Ophthalmology & Visual Science*, Jun. 1994, No. 7, vol. 35, pp. 3032-3044.
Vogel, Alfred et al., "Kinetics of Phase Transitions in Pulsed IR Laser Ablation of Biological Tissues", *SPIE*, 2003, vol. 4961, pp. 66-74.
Vogel, Alfred et al., "Laser-Induced Breakdown in The Eye At Pulse Durations From 80 ns to 100 fs", *SPIE*, 1998, vol. 3255, pp. 34-49.
Vogel, Alfred et al., "Numerical Simulation of Optical Breakdown for Cellular Surgery At Nanosecond to Femtosecond Time Scales", *SPIE*, 2001, vol. 4433, pp. 70-80.
Vrensen, G. F. J. M., "Aging of the human eye lens—A morphological point of view", *Comp. Biochem. Physiol.*, vol. 111A, 1995. pp. 519-53.
Waring III, George O., M.D., "Presbyopia and Accommodative Intraocular Lenses—the Next Frontier in Refractive Surgery?", *Refractive & Corneal Surgery*, vol. 8, Nov./Dec. 1992, pp. 421-423.
Weale, Robert D., Sc., "Presbyopia Toward the End of the 20th Century", *Survey of Ophthalmology*, vol. 34, No. 1, Jul.-Aug. 1989, pp. 15-29.
Werblin, Theodore P., M.D., "Should We Consider Clear Lens Extraction for Routine Refractive Surgery?", *Refractive & Corneal Surgery*, vol. 8, Nov./Dec. 1992, pp. 480-481.
Werner, Liliana, MD, et al., "Capsular Bag Opacification After Experimental Implantation of a New Accommodating Intraocular Lens in Rabbit Eyes", *J Cataract Refract Surg.*, 2004, vol. 30, pp. 1114-1123.
Werner, Liliana, MD. et al., "Posterior Capsule Opacification in Rabbit Eyes Implanted With 1-Piece and 3-Piece Hydrophobic Acrylic Intraocular Lenses", *J Cataract Refract Surg*, 2005, vol. 31, pp. 805-811.
Wilks, S. C. et al., "Absorption of ultra-Intense Laser Pulses", *Physical Review Letters*, vol. 69, No. 9, Aug. 31, 1992, pp. 1383-1386.
Wyatt, Harry J., "Application of a Simple Mechanical Model of Accommodation to the Aging Eye", *Eye Res.*, vol. 33, No. 5/6, 1993, pp. 731-738.
Ziebarth, Nöel, et al; "Non-contact Optical Measurement of Lens Capsule Thickness During Simulated Accommodation", *SPIE*, 2005, vol. 5688, pp. 19-25.
Zuclich, Joseph A. et al., "A comparison of laser-induced retinal damage from infrared wavelengths to that from visible wavelengths", *Lasers and Light*, vol. 8, No. 1, 1997, pp. 15-29.
Zuclich, Joseph A. et al., "In Situ Measurements of Lens Fluorescence and its Interference With Visual Function", *Investigative Ophthalmology & Visual Science*, vol. 33, No. 2, 1993, pp. 410-415.
Zuclich, Joseph, "In Vivo Measurements of Optical Properties of the Ocular Lens", Reprinted from Proceedings of Ultraviolet Radiation Hazards, Jan. 26-27, 1994, *SPIE—The International Society for Optical Engineering*, Vo. 2134B Ultraviolet Radiation Hazards, 1994, pp. 99-112.
Zuclich, J.A., et al., "Ocular Effects of Penetrating IR Laser Wavelengths", Reprinted from Proceedings of Laser-Tissue Interaction VI, Feb. 6-9, 1995, *SPIE—The International Society for Optical Engineering*, vol. 2391, 1995, pp. 111-125.
Zuclich, Joseph A., et al., "Rapid Noninvasive Optical Characterization of the Human Lens", *Lasers in the Life Sciences*, 6(1), 1994, pp. 39-53.
Zuclich, Joseph A., "Research on the Ocular Effects of Laser Radiation", Published by *Technology Incorporated: Life Sciences Division*, publication date unknown, 59 pgs.
Zuclich, Joseph A., "Ultraviolet-Induced Photochemical Damage in Ocular Tissues", *Health Physics*, vol. 56, No. 5, May 1989, pp. 671-681.
Zuclich, Joseph A., "Workshop on Long-Term Visual Health Risks of Optical Radiation—Thermal Cataracts Induced by UV Laser Radiation", *Workshop Report, Cataract Working Group*, publisher unknown, publication date unknown, 13 pgs.
Agrahari, S. et al., "The Potential of Photodisruption Laser Treatment of the Crystalline Lens to Rupture the Lens Capsule", *ARVO* Abstract No. 07-A-6800, 2006, 1 pg.
Faraggi, E. et al., "Stress confinement, shock wave formation and laser induced damage", Conference 5695: Optical Interactions with Tissue and Cells XVI, *Photonics West*, undated, 1 pg.
Fisher, R F, "The ciliary body in accommodation", *Trans Ophthalmol. Soc. UK*, 1989, vol. 105,1 pg.
Fisher, RF. "The mechanics of accommodation in relation to presbyopia", *Eye*, 1988, vol. 2, 1 pg.
Frey, R. W. et al., "Modification of Lens Mechanics of Human Cadaver and Porcine Lenses Using Photodisruption Laser to Change Lens Power and Increase Flexibility", *ARVO* Abstract No. 07-A-06652, 2006, 1 pg.
Garner, LF et al., "Changes in equivalent and gradient refractive index of the crystalline lens with accommodation", *Optom Vis. Sci.*, 1997, vol. 74,1 pg.
Garner LF et al., "Changes in ocular dimensions and refraction with accommodation", *Ophthalmic Physiol. Opt.*, 1997, vol. 17, 1 pg.

(56) References Cited

OTHER PUBLICATIONS

Gray, G. et al., "Constructions of a Computer Mesh Model of the Anatomical Human Crystalline Lens Fiber Ultrastructure", *Arvo Abstract*, 2006, 1 pg.

Helsterkamp, A. et al., "Nanosurgery in live cells using ultrashort laser pulses", Conference 5695: Optical Interactions with Tissue and Cells XVI, *Photonics West*, undated, 1 pg.

Kuszak, J.R., "Progressively More Complex Star Sutures Formed in Primate Lenses During Periods of Development, Growth and Aging Are Related to Accommodation", Abstracts Online, obtained from the Internet on Apr. 19, 2006 at: http://www.abstractsonline.com/viewer/viewAbstractPrintFriendly.asp?CKey={C8FDF5D . . . Apr. 19, 2006, I page.

Kuszak, J. R. et al., "Results From a Finite Element Model Analysis of the Accommodative Process Based on the Human Crystalline Lens Fiber Ultrastructure", *ARVO Abstract*, 2006, 1 pg.

McBrien NA et al., "Experimental myopia in a diurnal mammal (Sciurus carolinensis) with no accommodative ability", *J Physiol.*, 1993, vol. 469, 1 pg.

McCourt ME et al., "Refractive state, depth of focus and accommodation of the eye of the California ground squirrel (*Spermophilus beecheyi*)", *Vision Res.*, 1984, vol. 24, 1 pg.

Oberheide, U. et al., "Flexibility Increase of Human Donor Lenses After Femosecond Laser Treatment (fs-Lentotomy)", *ARVO Abstract* No. 3833/B571, 2007, 2 pgs.

Olmstead, T. et al., "The Use of an Off Axis Slit Laser Camera System for Determining Photodisruptive Laser Placement in Lenses", *ARVO Abstract* No. 07-A-5967, 2006, 1 pg.

Rafferty, NS et al., "Comparative study of actin filament patterns in lens epithelial cells, Are these determined by the mechanisms of lens accommodation?", *Curr Eye Res.*, 1989, vol. 8, 1 pg.

Roa, Ch. Mohan et al., "Level of Reduced Nucleotides and Lens Photodamage", *National Eye Institute*, undated, 1 pg.

Subramaniam, H. et al., "Finite Element Analysis of the Accommodative Process in the Whole Globe", *ARVO Abstract* No. 07-A-6249, 2006, 1 pg.

Van Alphen GW et al., "Elasticity of tissues involved in accommodation", *Vision Res.*, 1991, vol. 31, 1 pg.

Wang, B. et al., "In-vivo animal studies on intraocular nanosurgery with low-energy 80 MHZ near infrared femtosecond laser pulses", Conference 5695: Optical Interactions with Tissue and Cells XVI, *Photonics West*, undated, 1 pg.

Yeilding, R. H. et al., "Lens Culture System for Long Term Study of Porcine Lenses Pre and Post Laser Photodisruption Treatment", *ARVO Abstract* No. 01-A-6495, 2006, 1 pg.

Zepkin, N. et al., "Measurement of Temperature Rise in Porcine Crystalline Lenses from a Photodisruption Laser", *ARVO Abstract* No. 07-A-6709, 2006, 1 pg.

Zoltoski, R. K. et al., "Reverse Engineering of Human Lenses", *ARVO Abstract* No. 2018/B159, 2007, 2 pgs.

Avro, "Statement for the Use of Animals in Ophthalmic and Visual Research", *The Association for Research in Vision and* Ophthalmology, copyright © 2002, obtained from the Internet on Jan. 15, 2005 at: http://www.avro.org/AboutAvro/animalst.asp, 3 pgs.

Gattass, Rafael et al., "Femtosecond laser micromaching Applications in Technology and Biology", Photonics West conference Jan. 2005, 78 pgs.

Hermans, E. et al., "Estimating the External Force Acting on the Human Eye Lens During Accommodation Using Finite Elements Modeling", presentation on Accommodation & Presbyopia, May 2005, 1 pg.

Kuszak et al., "Light, scanning and electron micrographs have lead to the following interpretations of secondary fiber formation", 2004, 16 pgs.

Lubatschowski, H. et al., "Treatment of Presbyopia by Cutting the Cystaline Lens: A Comparison of FEM Simulation and Ex vivo Studies", *Lazer Zentrum Hannover e.V.*, Publication date unknown, 22 pgs.

Mazur, Eric, "An Introduction to Femtosecond Laser Science", Photonics West conference Jan. 2005, 291 pgs.

Nebel, Achim et al., "Fast Micromachining using Picosecond Lasers", Photonics West conference Jan. 2005, 37 pgs.

OSN SuperSite, "Increase in lens stiffness with age may cause presbyopia, study suggests", 2005, 1 pg.

"Presbyopia—preconditions", *Laser Zentrum Hannover*, undated, 11 pgs.

"Principles of Ultrafast Laser Surgery Femtosecond Laser-Tissue Interaction", copyright © Center for Ultrafast Optical Sciences, Un. of Michigan, undated, 3 pgs.

Roundy, Carlos—"Propagation factor qualifies leaser bean performance", *Laser World Focus*, undated, 3 pgs.

Shen, J. et al. "Measurement of the Lens Capsule Contraction Force in the Radial Direction", presentation on Accommodation & Presbyopia, May 2005, 1 pg.

Figure 4.2—Optical constants for a "standard eye", publication unknown, undated, 1 pg.

Picture of an eye obtained from the Internet on Mar. 28, 2005 at: http://www.opt.uh.edu/research/aglasser/aao/gonioani.gif, 1 pg.

Pictures of eyes, date and publisher unknown, 5 pgs.

Loesel paper graphs, date and publisher unknown, 2 pgs.

European Search Report, Application No. 07718200, mailed Mar. 4, 2015.

\* cited by examiner

SYSTEM AND METHOD FOR PROVIDING LASER SHOT PATTERNS TO THE LENS OF AN EYE

This application claims the benefit of priority under 35 U.S.C. §119(e)(1) of 1) U.S. Provisional Application Ser. No. 61/228,560 titled System and Method for Providing Laser Shot Patterns to the Lens of an Eye, filed Jul. 25, 2009 and 2) U.S. Provisional Application Ser. No. 61/228,529 titled System and Method for Providing Laser Shot Patterns to the Lens of an Eye, filed Jul. 24, 2009, and this application is a continuation-in-part application of both 1) U.S. patent application Ser. No. 12/217,285, titled System and Method for Improving the Accommodative Amplitude and Increasing the Refractive Power of the Human Lens with a Laser, filed Jul. 2, 2008 (now pending), which is a continuation-in-part of PCT/US2007/001353 filed Jan. 19, 2007, and 2) U.S. patent application Ser. No. 12/217,295 titled System and Apparatus for Delivering a Laser Beam to the Lens of an Eye, filed Jul. 2, 2008 (now pending), which is a continuation-in-part of PCT/US2007/001486 filed Jan. 19, 2007, wherein U.S. patent application Ser. No. 12/217,285 is a continuation-in-part application of both 1) U.S. patent application Ser. No. 11/414,838 titled System and Method for Providing the Shaped Structural Weakening of the Human Lens with a Laser, filed May 1, 2006 (now pending), which is a continuation-in-part application of U.S. patent application Ser. No. 11/337,127 titled System and Method for Treating the Structure of the Human Lens, filed Jan. 20, 2006 (now pending), and 2) U.S. patent application Ser. No. 11/414,819 titled System and Apparatus for Treating the Lens of an Eye, filed May 1,2006 (now pending), which is a continuation-in-part application of U.S. patent application Ser. No. 11/337,127 titled System and Method for Treating the Structure of the Human Lens, filed Jan. 20, 2006 (now pending), and wherein U.S. patent application Ser. No. 12/217,295 is a continuation-in-part application of both 1) U.S. patent application Ser. No. 11/414,838 titled System and Method for Providing the Shaped Structural Weakening of the Human Lens with a Laser, Filed May 1, 2006 (now pending), which is a continuation-in-part application of U.S. patent application Ser. No. 11/337,127 titled System and Method for Treating the Structure of the Human Lens, filed Jan. 20, 2006 (now pending), and 2) U.S. patent application Ser. No. 11/414,819 titled System and Apparatus for Treating the Lens of an Eye, filed May 1, 2006 (now pending), which is a continuation-in-part application of U.S. patent application Ser. No. 11/337,127 titled System and Method for Treating the Structure of the Human Lens, filed Jan. 20, 2006 (now pending), the entire contents of each of which is incorporated herein by reference.

BACKGROUND OF THE INVENTION

The present invention relates to methods and systems for improving procedures that address cataracts, opacifications in the lens, clear lens extraction, removal of natural lens material, use of lens replacement materials and combinations of these. The present invention additionally relates to systems and methods that provide predetermined, precise and reproducible laser shot patterns for creating incisions in the natural human crystalline lens that are reproducible from patient-to-patient and surgeon-to-surgeon.

In general, presbyopia is the loss of accommodative amplitude. In general, cataracts are areas of opacification within the crystalline lens, which are sufficient to interfere with vision. Other conditions, for which the present invention is directed, include but are not limited to the opacification of the crystalline lens.

Presbyopia most often presents as a near vision deficiency, the inability to read small print, especially in dim lighting after about 40-45 years of age. Presbyopia, or the loss of accommodative amplitude with age, relates to the eyes inability to change the shape of the natural crystalline lens, which allows a person to change focus between far and near, and occurs in essentially 100% of the population over age 45. Accommodative amplitude has been shown to decline with age steadily through the fifth decade of life.

Cataracts, or the condition when the natural crystalline lens becomes opaque and clouds vision, occurs in millions of people per year and are treated effectively with surgical techniques, such as ultrasonic phacoemulsification pioneered by Kelman about 40 years ago. Although the techniques have been refined over the years, safety concerns from ocular trauma, especially to the corneal endothelium from the ultrasonic energy required to break up a hardened cataract is undesirable, especially for those with a compromised corneal endothelium, such as those with Fuchs Dystrophy.

Several difficulties arise in the use of lasers in the treatment of cataracts. Cataracts scatter light, including laser light, and thus can prevent a laser treatment beam from having the desired effect on the tissue being treated. Moreover, the light scattering effect of cataracts and other opacifications can make determining the position and shape of the lens by optical means difficult.

The established treatment for cataracts is the removal of the opacified human crystalline lens and its replacement with an intra ocular lens (IOL). In general, IOLs consist of a small plastic lens with plastic side struts, called haptics, to hold the lens in place within the capsular bag inside the eye. Exemplary types of IOLs include monofocal lenses, multifocal IOLs, which provide the patient with multiple-focused vision at far and reading distances, and accommodative IOLs, which provide the patient with visual accommodation. The flexible nature of many IOLs enables them to be rolled and/or folded up for insertion into the capsule. Examples of IOLs are found in U.S. Pat. Nos. 7,188,949, 6,849,091, 5,699,142 and 5,607,472, the entire disclosures of each of which are incorporated herein by reference. Commercially available IOLs that, by way of example, may benefit from the present invention are CRYSTALENS and ACRYSOF RESTOR.

The CRYSTALENS IOL was developed by Eyeonics and is presently provided by Bausch & Lomb. It is at least in part believed to be disclosed in U.S. Pat. No. 6,849,091. Further information regarding its structure and efficacy is provided by the Food and Drug Administration (FDA) PMA P030002 and related documents to that PMA file. The FDA approved indicated use for CRYSTALENS was in part: "The Crystalens™ Model AT-45 Accommodating IOL is intended for primary implantation in the capsular bag of the eye for visual correction of aphakia in adult patients in whom a cataractous lens has been removed and is intended to provide near, intermediate, and distance vision without spectacles. The Crystalens™ IOL provides approximately one diopter of monocular accommodation." (Nov. 14, 2003 PMA P030002 at Part 2, Summary of Safety and Effectiveness Data, ¶INDICATIONS FOR USE).

Thus, the CRYSTALENS is an example of an FDA approved accommodating IOL. The term "FDA approved accommodating IOL" refers to any IOL that has obtained FDA approval having an indicated use that provides for accommodation, regardless whether such IOL is actually being employed for such an approved use.

The ACRYSOF RESTOR IOL is provided by Alcon and is at least in part believed to be disclosed in U.S. Pat. No. 5,669,142. Further information regarding its structure and efficacy is provided by FDA PMA P040020 and related documents to that PMA file. The FDA approved use for RESTOR was in part: "AcrySOF® ReSTOR® IOLs are indicated for the visual correction of aphakia secondary to removal of a cataractous lens in adult patients with and without presbyopia, who desire near, intermediate and distance vision with increased spectacle independence. The lens is intended to be placed in the capsular bag." (Apr. 24, 2004, PMA PO40020, at Part 2, Summary of Safety and Effectiveness Data, ¶INDICATIONS).

Thus, the RESTOR is an example of an FDA approved IOL for near, intermediate and distance vision. The term "FDA approved IOL for near, intermediate and distance vision" refers to any IOL that has obtained FDA approval having an indicated use that provides for near, intermediate and distance vision, regardless of whether such IOL is actually being employed for such an approved use. The CRYSTALENS would also be an example of an FDA approved IOL for near, intermediate and distance vision. Moreover, the RESTOR and CRYSTALENS are examples of an FDA approved IOLs that reduce and/or eliminate the need for spectacles.

A schematic representation of the shape and general structure of an example of an accommodating IOL, along the lines of a CRYSTALENS, is provided in FIG. 8. This IOL has a lens structure 202, hinges 203 located adjacent to the lens structure 202 and haptics 204, which contact the lens capsule 201. The overall shape of this IOL would be non-geometric. As used herein the term "non-geometric shape" refers to shapes other than circles, ellipses, squares and rectangles. As used herein the term "geometric shape" refers to circles, ellipses, squares and rectangles.

The removal of the natural crystalline lens and replacement with a lens replacement material employ the use of a small initial incision or incisions in the limbal area of the eye, which is the transition area between the cornea and sclera. This initial incision is typically made with a small triangular blade that is pushed through the outer clear cornea of the eye. It is through this initial incision that other instruments for use in the removal and replacement of natural lens material are inserted. It is also through this incision that the natural lens material is removed from the eye and replacement lens material is inserted into the eye.

Once the initial incision has been made the removal of the opacified natural crystalline lens and replacement with a lens replacement material, such as an FDA approved IOL, presently employees a capsulorhexis and/or a capsulotomy. A capsulorhexis generally consists of the removal of a part of the anterior lens capsule and the creation of a hole or opening in the lens capsule, that results at least in part from a tearing action. A capsulotomy generally consists of a cutting of the lens capsule, without or with minimum tearing of the capsule. Thus, to remove the opacified natural lens material, the lens capsule is opened. There are several known techniques for performing a capsulorhexis and a capsulotomy.

One of these capsulorhexis techniques is a can opener approach. This approach uses a small bent needle to make small incisions around the anterior lens capsule to create an opening in the lens through which the lens could be removed. This technique quite often results in the opening in the lens capsule having ragged edges. Another of these techniques is a Continuous Curvilinear Capsulorhexis (CCC). CCC uses the same type of bent needle to begin the tear in the anterior lens capsule and then uses this needle and/or special forceps which are guided under the edge of the cut to tear a circular hole in the lens capsule. CCC, in comparison to the can opener approach, reduces the ragged edge around the opening in the lens that occurred with using the can opener technique. However CCC does not eliminate the formation of irregularities in the shape of the edge and the presence of these irregularities is dependent upon surgical skill and technique.

The use of a Fugo plasma blade to create the hole in the anterior capsule may also be used. This technique is referred to as a capsulotomy. The Fugo plasma blade is a hand held device and was originally utilized in dentistry. It is an electromagnetic device that focuses its energy on a blunt cutting filament. Information regarding the Fugo plasma blade can be found in FDA PMA K063468, K001498, K041019, and K050933 and U.S. Pat. No. 5,413,574.

SUMMARY

The novel and improved methods and systems for the performance of incisions in the natural crystalline human lens, also at times referred to herein as the lens, the natural lens, the human lens, and the crystalline lens, which include aspects of the present inventions and which are set forth in detail in the present patent specification, may provide for better implementation of other methods and systems for delivering laser beams to the lens of the eye, such as those disclosed in published applications US 2007/173794A1, US 2007/173795A1, US 2007/185475A1, WO 2007/084694 A2 (now U.S. Ser. No. 12/217,295), and WO 2007/084627A2 (now U.S. Ser. No. 12/217,285) the entire disclosure of each of which is incorporated herein by reference.

Provided herein are embodiments of the present invention. There is provided a system for providing laser shot patterns to the natural human crystalline lens of an eye for softening the natural human lens, having a therapeutic laser for producing a laser beam; a laser shot pattern for performing a capsulotomy; a laser shot pattern having a first and a second area for sectioning a natural human lens of the eye, where the first area of the laser shot pattern has a different shot and/or cut density from the second area of the laser shot pattern; and in this way upon delivery of the shot pattern to the lens of the eye the shots will cause the lens to have different softness and apparent densities, which differences will correspond to the first and second areas.

Moreover, in this system the number of shots for the first area may be denser than the number of shots for the second area, the number of shots for the second area may be denser than the number of shots for first area, and the shot pattern may further have patterns for creating a number of volumetric shapes. These volumetric shapes for the first area may be denser than the number of volumetric shapes for the second area and the number of volumetric shapes for the second area may be denser than the number of volumetric shapes for first area. The patterns may consist essentially of volumetric shapes such as cubes and spheres.

Moreover, in this system the pattern of shots for the first area may be denser than the pattern of shots for the second area, the pattern of shots for the second area may be denser than the pattern of shots for first area, and the shot pattern may further have patterns for creating a number of volumetric shapes. These volumetric shapes for the first area may be more densely packed than the volumetric shapes for the second area and the volumetric shapes for the second area may be more densely packed than the volumetric shapes for the first area. The pattern of shots may consist essentially of a plurality of volumetric shapes such as cubes and spheres.

There is also provided a method of providing laser shot patterns to the natural human crystalline lens of an eye for softening the natural human lens, having a therapeutic laser for producing a laser beam; a laser shot pattern for performing a capsulotomy; a laser shot pattern having a first and a second area for sectioning a natural human lens of the eye, where the first area of the laser shot pattern has a different shot and/or cut density from the second area of the laser shot pattern; and in this way upon delivery of the shot pattern to the lens of the eye the shots will cause the lens to have different softness and apparent densities, which differences will correspond to the first and second areas.

Moreover in this method the pattern of shots for the first area may be denser than the pattern of shots for the second area, the pattern of shots for the second area may be denser than the pattern of shots for the first area, and the shot pattern may further have patterns for creating a number of volumetric shapes. These volumetric shapes for the first area may be more densely packed than the volumetric shapes for the second area and the volumetric shapes for the second area may be more densely packed than the volumetric shapes for first area. The pattern of shots may consist essentially of a series of volumetric shapes such as cubes and spheres.

Moreover in this method the number of shots for the first area may be denser than the number of shots for the second area, the number of shots for the second area may be denser than the number of shots for first area, and the shot pattern may further have patterns for creating a number of volumetric shapes. These volumetric shapes for the first area may be denser than the number of volumetric shapes for the second area and the number of volumetric shapes for the second area may be denser than the number of volumetric shapes for first area. The patterns may consist essentially of volumetric shapes such as cubes and spheres.

There is yet further provided a system and a method for providing laser shot patterns to the natural human crystalline lens of an eye for differentially softening the natural human crystalline lens, the system including: a therapeutic laser for producing a laser beam; a laser shot pattern for sectioning the natural human crystalline lens of the eye, including a first, a second and a third area; each area consisting essentially of a plurality of a volumetric shapes; at least two of the areas having different densities of the volumetric shapes; so that at least two of the areas when delivered to the natural human lens provide lens areas having different softnesses. In this system and method the shape of any one of the volumetric shapes may be in the shape of an aspiration tube or needle that is commonly used to remove lens material from the capsular bag. Further the shape of at least one of the areas may be based upon, or follow in whole or in part, the shape of such an aspiration tube or needle.

There is further provided a system and method for providing a laser beam shot pattern to a natural human crystalline lens of an eye, the system including a laser for providing a laser beam, a controller having associated with it a shot pattern. This shot pattern including a pattern for proving a multiplicity of independent spheres in the lens of the eye. Thus, pursuant to this system and method the shot pattern may include a pattern for providing at least five independent spheres along an axis of the lens of the eye, it may have a pattern for populating substantially the entire lens with spheres and it may comprise a pattern and sequence of delivery of the shots in the pattern that provide for the formation of a layer of bubbles at least partially surrounding a sphere. Additionally, this shot pattern may have associated therewith further patterns for performing capsulotomies.

Additionally, there is provided a method and a system for providing lubrication to lubricate natural human crystalline lens material for removal from an eye, the system and method have the following processes and components which include a laser for providing a laser beam, a controller having associated with it a shot pattern, the shot pattern having a pattern for providing a multiplicity of spheres in the lens of the eye; and, the placement of the shots in the shot pattern in the lens of the eye such that bubble formation occurring during the delivery of the laser beam associates itself with the spheres and provides lubrication for the removal of the spheres.

Moreover, there is provided a system and method for providing laser shot patterns to section the natural human crystalline lens of an eye and for softening and lubricating sections of the natural human lens, the system and method including: a therapeutic laser for producing a laser beam; a laser shot pattern for performing a capsulotomy; a laser shot pattern for sectioning a natural human lens of the eye; the laser shot pattern consisting essentially of a plurality of spheres; the laser shot pattern including a first area and a second area; and the first area of the laser shot pattern having a different shot and/or cut density from the second area of the laser shot pattern so that when the area shot pattern is delivered to the natural human crystalline lens provides a lens that is softened and lubricated for more easy removal.

There is also provided a system for providing laser shot patterns to the natural human crystalline lens of an eye for differentially softening the natural human crystalline lens, the system including a therapeutic laser for producing a laser beam laser shot pattern for sectioning the natural human crystalline lens of the eye, including a first and a second pattern, the first pattern consisting of a plurality of laser shots to create a plurality of radial cuts in the lens, the second pattern consisting of a plurality of laser shots to create a plurality of cylindrical cuts. Wherein the cylindrical cuts are concentrically positioned in the area of the radial cuts. Still further, the first pattern may have a plurality of laser shots to create a plurality of radial cuts in the lens, the radial cuts sharing a common center point, the second pattern may have a plurality of laser shots to create a plurality of cylindrical cuts, and the cylindrical cuts may be substantially concentric and substantially sharing an common center point. Wherein the cylindrical cuts may be concentrically positioned in the area of the radial cuts and the radial common center and cylindrical common center points are substantially coincident. An improvement to the above pattern of cuts is one in which radial cuts are absent in the central cylinder of the concentric series of cylindrical cuts. Such a pattern of cuts has the advantage that it eliminates the high density of laser shots from the plurality of radial cuts which otherwise would intersect at or near the center of the pattern. The elimination of the central section of radial cuts in turn prevents a buildup of bubbles in the center of the pattern and improves the safety profile of the pattern by avoiding generation of a high level of radiant exposure of laser light in the central region of the cornea or retina.

Additionally there is provided a system for providing laser shot patterns to the natural human crystalline lens of an eye for differentially softening the natural human crystalline lens, the system including: a therapeutic laser for producing a laser beam; a laser shot pattern for sectioning the natural human crystalline lens of the eye, including a first and a second pattern; the first pattern having a plurality of laser shots to create a plurality of radial cuts in the lens; the second pattern having a plurality of laser shots to create a plurality of cylindrical cuts; and, wherein the cylindrical cuts are positioned in the area of the radial cuts.

Moreover there are provided systems and method for providing a laser beam shot pattern to a natural human crystalline lens of an eye, the system including having or providing a laser for providing a therapeutic laser beam; the laser having a controller associated with it, the controller having a shot pattern associated with it; the shot pattern including a pattern for proving a multiplicity of substantially rods of a square or rectangular cross section in the lens of the eye; and, delivering or being capable of delivering the shot pattern to the lens of the eye. Further these provided embodiments may have shot pattern includes a pattern for providing at least 2, at least 3, at least 4 and at least 5 substantially independent rods, that may further be are substantially rectangular or tubular or combinations of both. Alternatively the square or rectangular cross section tubes may be contiguous such that they form a space filling volume which occupies the central volume within the crystalline lens.

One of ordinary skill in the art will recognize, based on the teachings set forth in these specifications and drawings, that there are various embodiments and implementations of these teachings to practice the present invention. Accordingly, the embodiments in this summary are not meant to limit these teachings in any way.

DESCRIPTION OF THE PREFERRED EMBODIMENTS

Figure 1:
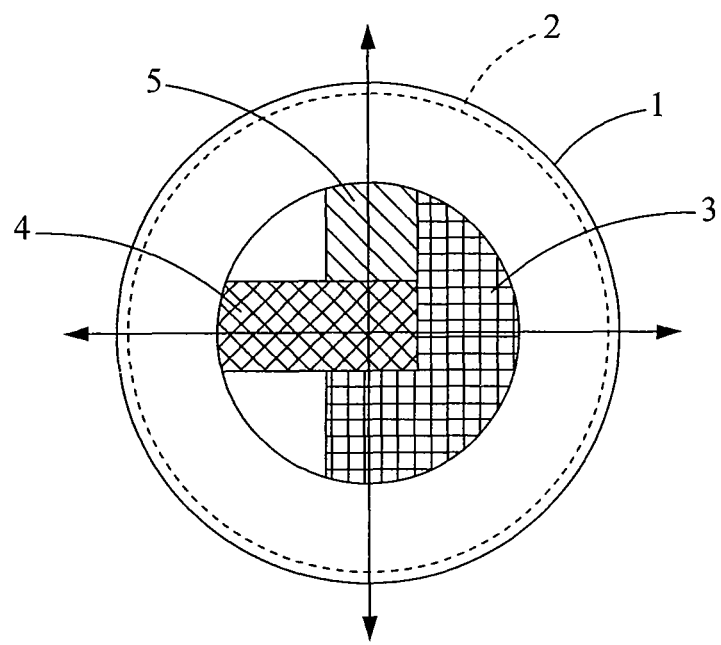
FIG. 1 is a diagram showing a shot pattern for the sectioning and removal of lens material.

In general, the present inventions relate to methods and systems for providing a laser to the lens of the eye to address and improve procedures relating to the removal of the natural crystalline lens and replacement of that lens with lens replacement material, and more specifically to improvements in systems and methods related to cataract surgery. In particular, the present inventions relate to methods and systems for providing predetermined laser shot patterns to the natural crystalline lens of the eye, which shots patterns have different densities of shots and cuts. These shot patterns when delivered to the lens effecting a softening of the lens material making it easier to remove from the lens capsule. Thus, the present invention provides the ability to customize and predetermine the relative amounts of force that are needed to remove specific sections of the lens material during cataract surgery.

The present methods and systems can be used with the novel and innovative laser system techniques that are the subject of the co-pending patent applications that are cited herein and which have been incorporated herein by reference, and the present methods and systems may possibly be used with other laser delivery systems for the removal of lens material to the extent such systems may be developed in the future. Preferably, the present methods and systems can be incorporated into and used in conjunction with the systems of the co-pending applications that have been incorporated herein by reference. In this way a single system, with a single therapeutic laser, can function as a start to finish device for performing the cuts necessary to remove and replace the natural lens.

Novel and pioneering laser systems and methods for the removal and replace of lens material are disclosed in U.S. provisional and regular patent applications: Ser. No. 61/228,506, System and Method for Performing a Jigsaw Capsulotomy: Ser. No. 61/228,484, System and Method for Performing and Sealing Limbal Area Incisions in the Eye; Ser. No. 61/228,514, System and Method for Performing Corrective Arcuate Incisions in the Eye; Ser. No. 12/509,412, Method and System for Removal and Replacement of Lens Material from the Lens of an Eye; and, Ser. No. 12/509,211, Method and System for Creating a Bubble Shield for Laser Lens Procedures, which were filed on Jul. 24, 2009, and the entire contents of each of which are incorporated herein by reference.

Thus, there is provided a system and method for the structural modification of the lens to make it easier to remove while potentially increasing the safety of the procedure by reducing and/or eliminating the need to use high frequency ultrasonic energy used in phaco emulsification. In general, the use of photodisruption cutting in specific volumetric shape patterns is utilized to create a sectioned lens, i.e., to carve up the lens into sectioned volumetric shapes. Moreover, the size, shape and distribution of these volumetric shapes can be placed in the lens of the eye in such a way as to create areas of varying density, apparent density, or softness, which areas may have different and predetermined shapes.

As used herein when the lens is referred to as becoming softer, or softening, when lens material is becoming easier to remove from the lens capsule and thus will require less force and effort to be removed. Thus, as disclosed herein the lens becomes softer after it has interacted with a laser using a given shot density, and/or a given cut density. Thus, as used herein softness increases for the region of treatment as the cut density increases. Similarly, as softness increases, the amount of force and effort to remove the lens decreases. In general, if the similar shape cuts and patterns are being used, patterns with a greater density of shots and patterns with a greater number of cuts will result in lens that has greater increases in softness and requires less force and effort to be removed.

Figure 4:
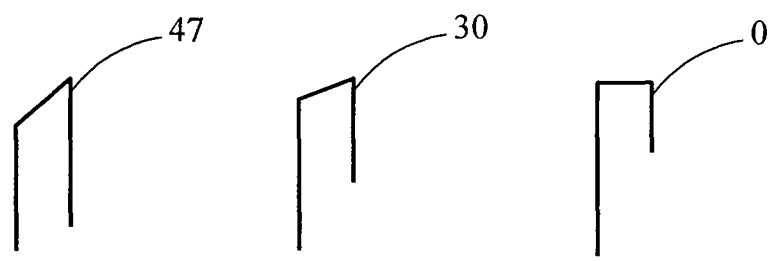
FIG. 4 is a cross sectional diagram showing three types of aspiration needles for removal of lens material.

The shapes of these areas can be varied to coincide with the shape of the tip of the aspiration needles that are used to remove the lens material from the capsule, either with or without phaco emulsification. Typically, these needles have tips which have a 47°, 30° or a 0° edge. These tips are illustrated in FIG. 4 as tip 47, 30 and 0 respectively.

A shot pattern for providing areas of varying density is provided in FIG. 1. Thus, there is shown a plan view schematic of a natural human lens and thereon is provided a lens having a lens capsule 1 and an area of hydrodissection 2. There is further provided, by way of example, three areas of varying shot density, a first area 3, a second area 4 and a third area 5.

There is provided a first area of varying shot and/or cut density 3. This area of varying density is formed by cutting the lens into volumetric shapes such as cubes, spheres as provided in greater detail in this specification, cones, rods, etc. The density of these volumetric shapes (as well as the laser shots and cuts used to form them) in this first area is low.

There is provided a second area of varying shot and/or cut density 4. This area of varying density is formed by cutting the lens into volumetric shapes such as cubes, spheres as provided in greater detail in this specification, cones, rods, etc. The volumetric shapes of this second area may be the same as or they may be different from the volumetric shapes of the first area. The density of these volumetric shapes (as well as the laser shots and cuts used to form them) in the second area 4 is greater than the density of volumetric shapes in the first area 3.

There is provided a third area of varying shot and/or cut density 5. This area of varying density is formed by cutting the lens into volumetric shapes such as cubes, spheres as provided in greater detail in this specification, cones, rods, etc. The volumetric shapes of this third area may be the same as or they may be different from the volumetric shapes of the first area or the volumetric shapes of the second area. The density of these volumetric shapes (as well as the laser shots and cuts used to form them) in the third area 5 is greater than the density of volumetric shapes in the second area 4.

Thus, in FIG. 1 there is provided three shot patterns having varying shot and cut density, when applied to the lens of an eye these shot patterns will result in three areas of lens, having corresponding shapes and having varying softness as described above.

Figure 2:
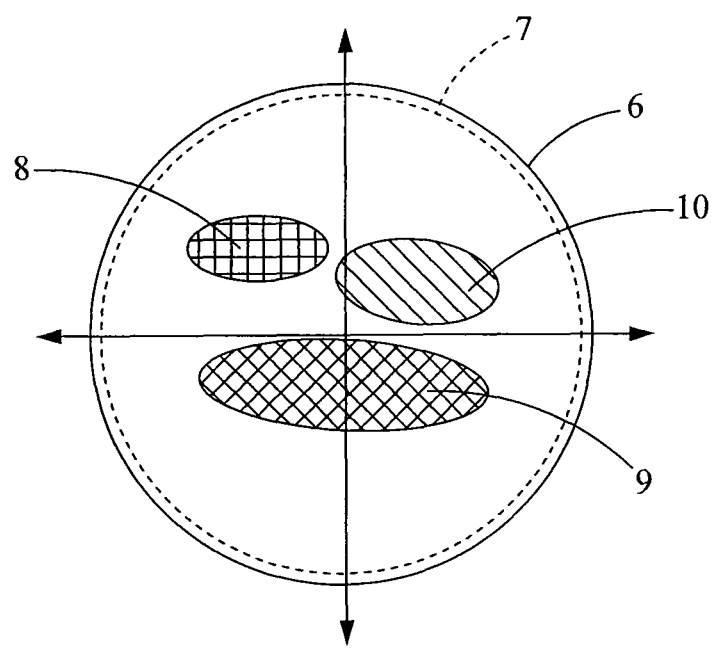
FIG. 2 is a diagram showing a shot pattern for the sectioning and removal of lens material.

A shot pattern for providing areas of varying shot and/or cut density is provided in FIG. 2. Thus, there is shown a plan view schematic of a natural human lens and thereon is provided a lens having a lens capsule 6 and an area of hydrodissection 7. There is further provided, by way of example, three areas of varying shot density, a first area 8, a second area 9 and a third area 10.

There is provided a first area of varying shot and/or cut density 8. This area of varying density is formed by cutting the lens into volumetric shapes such as cubes, spheres as provided in greater detail in this specification, cones, rods, etc. The density of these volumetric shapes (as well as the laser shots and cuts used to form them) in this first area is low.

There is provided a second area of varying shot and/or cut density 9. This area of varying density is formed by cutting the lens into volumetric shapes such as cubes, spheres as provided in greater detail in this specification, cones, rods, etc. The volumetric shapes of this second area may be the same as or they may be different from the volumetric shapes of the first area 8. The density of these volumetric shapes (as well as the laser shots and cuts used to form them) in the second area 9 is greater than the density of volumetric shapes in the first area 10.

There is provided a third area of varying density 10. This area of varying density is formed by cutting the lens into volumetric shapes such as cubes, spheres as provided in greater detail in this specification, cones, rods, etc. The volumetric shapes of this third area may be the same as or they may be different from the volumetric shapes of the first area or the volumetric shapes of the second area. The density of these volumetric shapes (as well as the laser shots and cuts used to form them) in the third area 10 is greater than the density of volumetric shapes in the second area 9. Thus, the apparent density of the lens in this third area 10 will be lower than the apparent density of lens in the second area 9, and in turn, the apparent density of the lens in the second area 9 will be lower than the apparent density of lens in the first area 8, which in turn is lower than the apparent density in the lens before sectioning.

As used herein when referring to the apparent density of sectioned lens in an area varying density; lower apparent density lens areas correspond to softer and more easily aspirated material, while higher apparent density lens areas correspond to firmer and more difficult to aspirate material. As used herein when referring to areas of varying density, the use of the term first, second, and third are relative terms with respect to density of a particular pattern and do not refer to the sequence of order in which those patterns are placed on the lens. Moreover, as used herein the term area refers to and includes 3-dimensional, i.e., volumetric, shapes.

Figure 3:
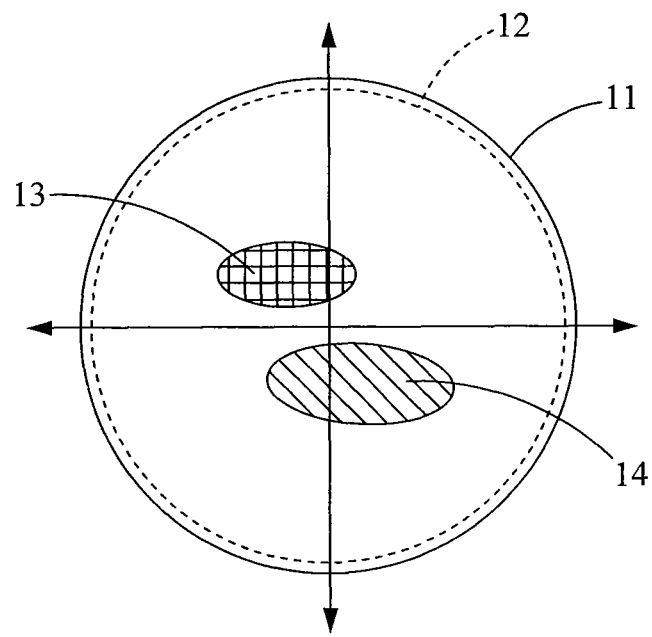
FIG. 3 is a diagram showing a shot pattern for the sectioning and removal of lens material.

A shot pattern for providing areas of varying shot and/or cut density is provided in FIG. 3. Thus, there is shown a plan view schematic of a natural human lens and thereon is provided a lens having a lens capsule 11 and an area of hydrodissection 12. There is further provided, by way of example, two areas of varying shot density, a first area 13 and a second area 14.

There is provided a first area of varying shot and/or cut density 13. This area of varying density is formed by cutting the lens into volumetric shapes such as cubes, spheres as provided in greater detail in this specification, cones, rods, etc. The density of these volumetric shapes (as well as the laser shots and cuts used to form them) in this first area is low.

There is provided a second area of varying shot and/or cut density 14. This area of varying shot and/or cut density is formed by cutting the lens into volumetric shapes such as cubes, spheres as provided in greater detail in this specification, cones, rods, etc. The volumetric shapes of this second area may be the same as or they may be different from the volumetric shapes of the first area. The density of these volumetric shapes (as well as the laser shots and cuts used to form them) in the second area 14 is greater than the density of volumetric shapes in the first area 13.

Figure 5:
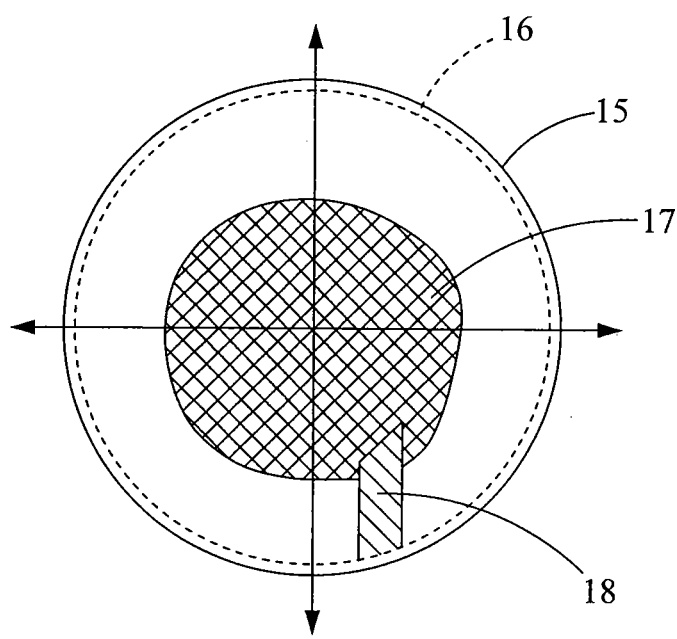
FIG. 5 is a diagram showing a shot pattern for the sectioning and removal of lens material.

There is provided in FIG. 5 a shot pattern for providing areas of varying shot and/or cut density in which the shape of the area of highest shot and/or cut density is in the shape of and thus corresponds to the shape of a 47° aspiration tube. Thus, there is shown a plan view schematic of a natural human lens and thereon is provided a lens having a lens capsule 16 and an area of hydrodissection 16. There is further provided, by way of example, two areas of varying shot density, a first area 17 and a second area 18.

There is provided a first area of varying shot and/or cut density 17. This area of varying density is formed by cutting the lens into volumetric shapes such as cubes, spheres as provided in greater detail in this specification, cones, rods, etc. The density of these volumetric shapes (as well as the laser shots and cuts used to form them) in this first area is low.

There is provided a second area of varying shot and/or cut density 18. This area of varying density is formed by cutting the lens into volumetric shapes such as cubes, spheres as provided in greater detail in this specification, cones, rods, etc. The shape of this area of varying density corresponds to the shape of a 47° aspiration tube or needle, i.e., FIG. 4 tube shape 47. The volumetric shapes of this second area may be the same as or they may be different from the volumetric shapes of the first area. The density of these volumetric shapes (as well as the laser shots and cuts used to form them) in the second area 18 is greater than the density of volumetric shapes in the first area 17. Thus, the lens where the second shot pattern is applied will be softer than the lens in the first area. In this way there is created by the application of these two patterns an area of softened lens that provides for the easier, safer and less traumatic initial insertion of the aspiration tube or needle. Accordingly, by first aspirating the material from area 18, a surgeon can then insert the aspiration tip into area 17 to hold and/or gain better access to area 17 and further help propagate the manipulation of the lens for removal.

While the second area 18 is illustrated in FIG. 5 as corresponds to the shape of a 47° aspiration tube 47 (of FIG. 4) it should be understood that this shape could also correspond to the other shapes of aspiration tubes currently used, for example the current shape of aspiration tubes are shown in FIG. 4 (in which shape 47 illustrates the shape of a 47° aspiration tube, shape 30 illustrates the shape of a 30° aspiration tube shape 0 illustrates the shape of a 0° aspiration tube), or shapes developed in the future.

Figure 6A:
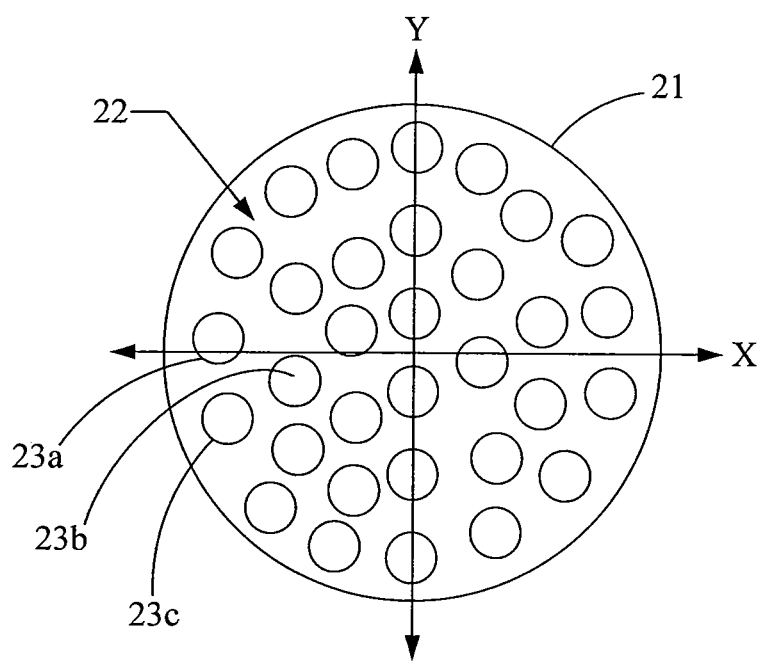
FIGS. 6A and 6B are plan and cross sectional diagrams of a lens showing a multiplicity of spheres shot pattern.
Figure 6B:
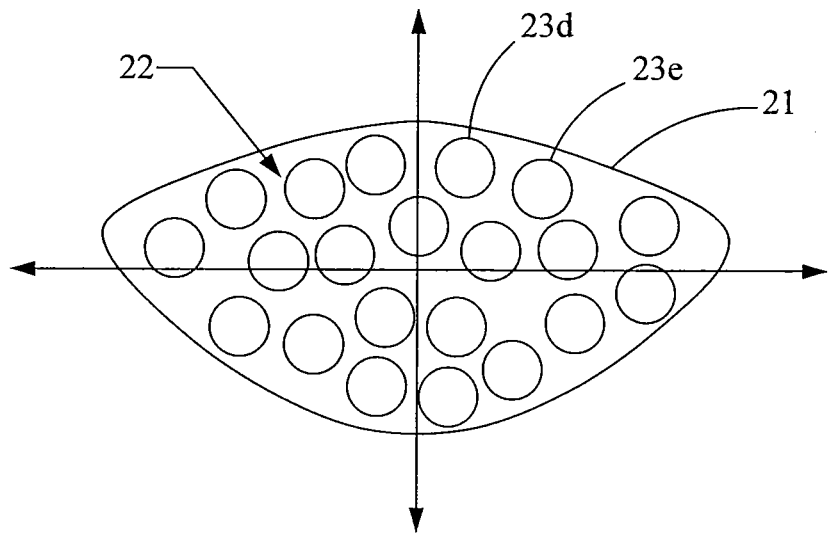

A shot pattern is provided in FIGS. 6A and 6B. FIG. 6A is a plan view of the lens of an eye having a multiplicity of spheres shot pattern thereon and FIG. 6B is a cross sectional view of the same lens having the same multiplicity of spheres pattern thereon. FIGS. 6A and 6B by way of example and without limitation illustrate a pattern where when applied to the lens will cut the lens so that substantially all of the lens has been populated with independent spheres. Although not shown a hydrodissection may be used with this shot pattern. There is provided a lens capsule 21 and a multiplicity of spherical laser shot patterns 22, which has a plurality of individual sphere patterns 23, (only a few of the spheres 23 are numbered, i.e., 23a, 23b, 23c, 23d, and 23e, to avoid making the figure confusing) which sphere patterns do not touch and are separated by lens material.

In this particular embodiment the spheres are of a size that provides for the placement of six spheres along the y axis of the lens. The size of the spheres may vary provided that space is left between them and that a sufficient number of spheres are cut into the lens to soften the lens for extraction.

Figure 6C:
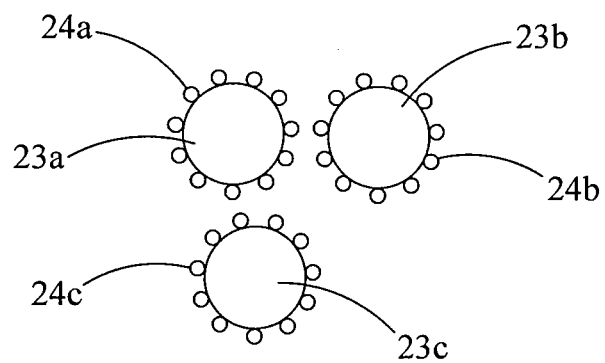
FIG. 6C is a diagram of some of the spheres from the pattern of FIGS. 6A & 6B.

The creation of these spheres in the lens of the eye will cause the formation of bubbles. These bubbles will be associated with the spheres and it is theorized that they may be present around the sphere, i.e., on the surface of the sphere. These bubbles will serve as lubrication for the movement of the spheres into the aspiration needle for removal. The bubble layer is provided by way of illustration in FIG. 6C. Thus, there are shown spheres 23a, 23b, and 23c, from the plurality of spheres in FIGS. 6A & 6B. These spheres each have bubble layers, 24a, 24b and 24c associated respective with them. These bubble layers can be made up of individual bubbles that have not coalesced, bubbles that have coalesced into a film, and combinations thereof.

The sequence of laser shots in the patterns herein may be executed from posterior to anterior, as in most of the patterns disclosed herein, to obtain more predictable results by reducing the variation caused by shooting through gas bubbles. However, it may be desirable to shoot cataracts from the anterior to the posterior for the purpose of choosing the lesser of two undesirable effects. Thus, it may be advantageous to shoot through the gas bubbles, or let them dissipate, rather than shooting through cataractous tissue, which much more severely scatters the light and more quickly prevents photodisruption compared to gas bubble interference. Accordingly, it is proposed to photodisrupt the most anterior sections of the cataract first, then move posteriorally, shooting through gas bubble remnants of cataractous tissue, to the next layer of cataract tissue below. In addition to shooting the laser in anterior z planes then moving posterior, it is further provided to essentially drill down anterior to posterior, which is called herein the z axis and then move in x/y and drill down again. These shot patterns may also be applied to a clear lens and that lens is subsequently removed. It is desirable when dealing with a clear lens that shooting from posterior to anterior is utilized.

Figure 7:
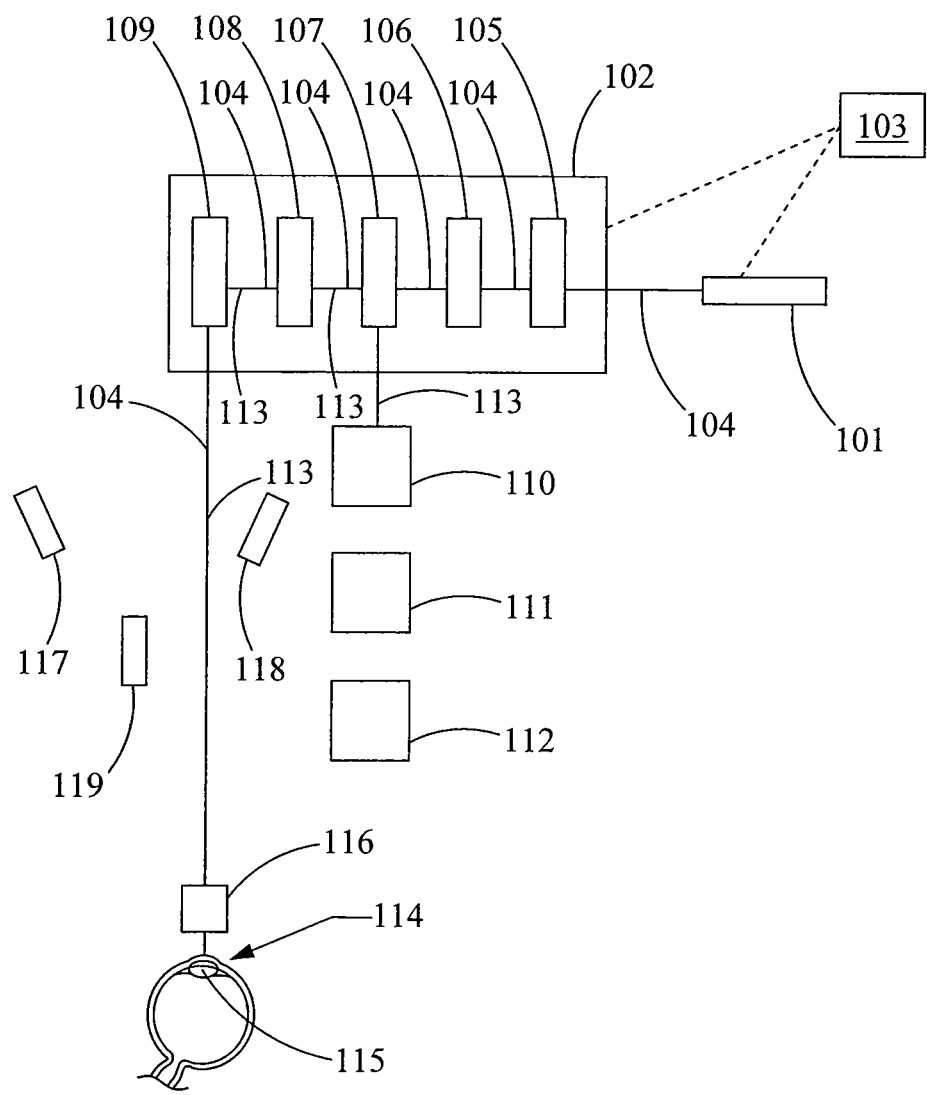
FIG. 7 is a schematic diagram of a type of system for delivering a laser beam shot pattern, such as the shot patterns of FIGS. 1-3, 5, 9 and 11-17, to the lens of an eye.

In general a preferred laser system, i.e., a laser device, for treating patients is provided as shown by way of example in FIG. 7. In this system there is provided a treatment laser 101; optics 102 for delivering the laser beam 104; a control system 103 for delivering the laser beam to the lens in a particular pattern 103, which control system 103 is associated with and/or interfaces with the other components of the system, as shown for example by dashed lines in FIG. 7, and/or other control systems not shown in FIG. 7.

In general, a laser system for providing the softening of the natural crystalline lens by generating laser incisions in the lens has by way of example and referring to FIG. 7 a treatment laser 101 which should provide a beam 104 that is of a wavelength that transmits through the cornea, aqueous and lens. The beam should be of a short pulse width, together with the energy and beam size, to produce photodisruption. Thus, as used herein, the term laser shot or shot refers to a laser beam pulse delivered to a location that results in photodisruption. As used herein, the term photodisruption essentially refers to the creation of a microscopic shock wave at laser beam focus and conversion of matter to a gas by the laser. The term photodisruption has also been generally associated with Laser Induced Optical Breakdown (LIOB). In particular, wavelengths of about 300 nm to 2500 nm may be employed. Pulse widths from about 1 femtosecond to 100 picoseconds may be employed. Energies from about a 1 nanojoule to 1 millijoule may be employed. The pulse rate (also referred to as pulse repetition frequency (PRF) and pulses per second measured in Hertz) may be from about 1 KHz to several GHz. Generally, lower pulse rates correspond to higher pulse energy in commercial laser devices. A wide variety of laser types may be used to cause photodisruption of ocular tissues, dependent upon pulse width and energy density. Thus, examples of such lasers are disclosed in 2007/084694 A2 and WO 2007/084627A2 (now U.S. Ser. No. 12/217,285), the entire contents of each of which are incorporated herein by reference. These and other similar lasers may be used a therapeutic lasers.

In general, the optics for delivering 102 the laser beam 104 to the structures of the eye including the natural lens of the eye should be capable of providing a series of shots to the natural lens in a precise and predetermined pattern in the x, y and z dimensions. The z dimension as used herein refers to that dimension which has an axis that corresponds to, or is essentially parallel with the optical (AP) axis of the eye. The optics should also provide a predetermined beam spot size to cause photodisruption with the laser energy reaching the natural lens, or other structure of the eye intended to be cut.

In general, the control system 103 for delivering the laser beam 104 may be any computer, controller, and/or software hardware combination that is capable of selecting and controlling x-y-z scanning parameters and laser firing. These components may typically be associated at least in part with circuit boards that interface to the x-y scanner, the z focusing device and/or the laser. The control system may also, but does not necessarily, have the further capabilities of controlling the other components of the system, as well as, maintaining data, obtaining data and performing calculations. Thus, the control system may contain the programs that direct the laser through one or more laser shot patterns. Similarly, the control system may be capable of processing data from the biometric slit scanned laser and/or from a separate controller for the slit scanned laser system. The slit scanned laser system is a system used to measure the position of optical surfaces within the eye, such as the anterior and posterior lens and corneal surfaces or other eye features such as crystalline lens cataracts. Such measurements are used by the control system to generate patterns of laser shots to perform the desired crystalline lens incisions.

The laser optics for delivering 102 the laser beam 104 comprise a beam expander telescope 105, a z focus mechanism 106, a beam combiner 107, an x-y scanner 108, and focusing optics 109. There is further provided relay optics 110, camera optics 111, which include a zoom, and a first ccd camera 112.

Optical images 113 of the eye 114 and in particular optical images of the natural lens 115 of the eye 114 are conveyed along a path 113. This path 113 follows the same path as the laser beam 104 from the natural lens 115 through the laser patient interface 116, the focusing optics 109, the x-y scanner 108 and the beam combiner 107. There is further provided a laser patient interface 116, and a structured light source 117 and a structured light camera 118, including a lens. Examples of patient interface and related apparatus that are useful with the present system are provided in U.S. application Ser. No. 12/509,021, Liquid Filled Index Matching Device for Ophthalmic Laser Procedures, Ser. No. 61/228,457, Liquid Holding Interface Device for Ophthalmic Laser Procedures, filed Jul. 24, 2009, Ser. No. 12/840,818, Liquid Holding Interface Device for Ophthalmic Laser Procedures, filed Jul. 21, 2010 the entire disclosure of each of which is incorporated herein by reference.

A structured light source 117 may be a slit illumination having focusing and structured light projection optics, such as a Schafter+Kirchhoff Laser Macro Line Generator Model 13LTM+90CM, (Type 13LTM-250S-41+90CM-M60-780-5-Y03-C-6) or a StockerYale Model SNF-501L-660-20-5, which is also referred to as a slit scanned laser. In this embodiment the structured illumination source 117 also includes slit scanning means 119.

When using a scanned slit illumination the operation includes positioning the slit on one side of the lens, taking an image then moving the slit approximately one slit width, then taking another image, and then repeating this sequence until the entire lens is observed. For example, a 100 μm slit width can scan a nominal 9 mm dilated pupil diameter in 90 images, which takes approximately 3 seconds using a 30 Hz frame rate camera. To obtain images of the anterior surface in a single image without overlap, the slit should be at an angle to the axis of the structured light camera 118, i.e., it should not be parallel to that axis. The nominal slit angle can be approximately 30-60 degrees from the structured light camera axis. Any visible or near IR wavelength source within the sensitivity of the camera may be used. Low coherence length sources are preferable to reduce speckle noise in the structured camera image.

The structured light illumination source 117 and the structured light camera 118 are arranged in an angled relationship. The angled relationship, which may include angling the detector of the structure light camera with respect to the axis of the camera optics may be but is not required to be in the so-called Scheimpflug configuration, which is well-known.

The structured light source 117, in conjunction with the slit scanning means 119, projects a line and or a plurality of lines onto the cornea and crystalline lens 115 at an angle or plurality of angles. The light scattered from these objects is focused by the lens 115 onto the camera system 118. Since the slit illuminated image of the cornea and lens 115 is at a large angle with respect to the camera 118, this presents a large depth of field to the camera and the entire slit image may not be in sharp focus at the camera. By tilting the camera at an angle or plurality of angles the image along the illuminated plane can be in sharper focus. To the extent that a sharper focus is not obtained, arithmetic data evaluation means are further provided herein to determine a more precise location of the illuminated structures with respect to the laser device.

Alternatively, the structured light illumination source may be a focused beam whose point of focus is scanned throughout the regions of interest within the eye. The scanned path of the beam might simulate the area illuminated by the scanned slit illumination described above by executing a raster scan of a plane of the eye analogous to that illuminated by the slit laser. In this context, raster scan refers to a process in which the beam focus is scanned, row by row, to illuminate a section of the eye. In this case, the camera's detector would be exposed to the scattered light from the scanned beam for the whole duration of the raster scan.

The images from the camera 118 may be conveyed to the controller 103 for processing and further use in the operation of the system. They may also be sent to a separate processor and/or controller, which in turn communicates with the controller 103. The structured light source 117, the camera 118 and the slit scanning means 119 includes a means for determining the position crystalline lens and corneal surfaces in relation to the laser system and thus includes a means for determining the position and apex of the lens in relation to the laser system.

The delivery of laser shot patterns for the removal of lens is provided. Thus, there are provided methods and systems for producing cuts, i.e., incisions in the anterior lens capsule. These cuts are created by the therapeutic laser beam 104 being delivered to the anterior lens capsule in precise predetermined and highly reproducible patterns, delivery results in precise predetermined and highly reproducible shaped cuts in patterns as described and taught herein, or as may be called for by the use of a particular IOL or other device or material to be inserted within the lens capsule. As used herein geometric shaped patterns or cuts referrer to circular and elliptical shaped patterns or cuts. As used herein non-geometric shaped patterns or cuts refers to all other shapes that are not circular or elliptical.

The methods and systems to create these cuts in the anterior capsule provide superior results to the handheld methods and apparatus previously known for performing capsulorhexus and capsulotomy, and thus, the methods and systems disclosed herein are considered to be a substantial advancement in these techniques. In addition the delivery of the laser beam shots in a manner that greatly reduces the risk of a missed cut, which depending upon the particular application may be very significant is provided. Moreover, anterior capsule cuts are envisioned and provided that may be a continuous cuts, cuts and lands (uncut capsule portions between cuts) and perforations. Thus, as used herein the terms "missed cut" or "missed cuts" refer to a cut that was intended to be carried out by the delivery of a particular laser shot pattern, but which did not occur because the laser beam missed the lens capsule or targeted lens material or the targeted material was hit but not cut. Thus, in a cut and land pattern the lands would not be considered missed cuts, if they were intended to be left uncut by the laser pattern.

The cuts in the lens anterior surface are for the purpose of creating an opening in the lens capsule for the remove of the interior structures of the lens. To facilitate this removal there are provided various laser shot patterns that cut the interior structure of the lens into small volumes, which volumes can then be removed from the lens capsule. These small volumes can range from about 0.1 mm$^3$ to about 30 mm$^3$ and more preferably from about 0.4 mm$^3$ to about 1 mm$^3$. Thus a grid laser shot pattern within the interior structures of the lens, which creates cube shaped volumes of interior lens material, can be employed. These cubes can range in size from a side having a length of about 100 μm to about 3 mm, to about 4 mm, with about 500 μm to 2 mm being a preferred size. An ideal size for the volumetric shapes is one in which the dimensions of the volumetric shape roughly match the size of the opening at the distal end of the aspiration tube. This enables the individual volumetric shape pieces to be easily aspirated into the aspiration tube without or with minimal use of ultrasound energy. Volumetric shape pieces that are substantially smaller than the opening in the aspiration tube require more laser shots without added significant benefit. Additionally, this invention is not limited to the formation of cubes and other volumetric shapes of similar general size may be employed. For example, in addition to the spheres that are provided herein and illustrated in FIGS. 6A-6C, arrangement of other shapes such as triangles and pie sliced volumes may be employed.

The laser cut in the anterior capsule is used to create a small opening in the lens anterior surface of the lens capsule for removal of the sectioned volumes of interior material. Thus, this procedure may be used to treat cataracts. This procedure may also be used to remove a lens having opacification that has not progressed to the point of being cataractous. This procedure may further be used to remove a natural lens that is clear, but which has lost its ability to accommodate. In all of the above scenarios, it being understood that upon removal of the lens the lens capsule would subsequently house a suitable replacement, such as an IOL, accommodative IOL, or synthetic lens refilling materials. Moreover, the size and the shape of the opening is variable and precisely controlled and preferably for presently known lens refilling materials and IOLs is 2 mm or less diameter for lens refilling applications and about 5 mm for IOLs.

The creation of capsulotomy for the surgeon to access the lens to remove the lens is illustrated in FIGS. 10 A-D. In these figures there is provided an outer surface 801, which surface is formed by the lens capsule, and thus an outer shape of the lens. There is further provided a ring shaped band cut 802 and shot pattern. This shot pattern is provided by placing the laser beam in a series of tightly placed shots around the ring at the deepest depth (most posterior ring) and then continuing that sequence as the depth of the ring is decreased. Thus, in general the shot will be distributed entirely around the ring at a particular depth before moving to a shallower depth. Thus, the figure shows the cross section view of this cylindrical incision and accordingly provides for two sides 802 of the ring. The ring shaped capsulotomy cuts of 100 μm deep, approximately centered on the apex as determined by the above referenced method of the anterior lens capsule surface and precisely 5 mm in diameter. The diameter of the capsulotomy can be varied between about 0.1 mm to about 9 mm diameter.

Since the lens capsule is approximately 5 to 15 μm thick, it is desirable for the depth of the cut to be typically between 5 and several hundred um, although there is not much penalty for cutting several millimeters. With greater precision regarding the location and shape of the lens and lens apex the thickness of the band and in particular the amount of the band that is above the lens capsule and in the aqueous can be reduced. The shape of the capsulotomy can be elliptical with the x-axis different then the y-axis or other shapes. Thus, the shape of the capsulotomy can be any shape that provides a benefit for a particular IOL, for example the shape of the capsulotomy can be circular, elliptical, square, rectangular, or a non-geometric shape. The shape will be based at least in part upon and be determined at least in part by, the aspects of IOLs and in particular accommodating IOLs and IOLs that reduce and/or eliminate the need for spectacles. A particular IOL, such as FDA approved IOLs discussed herein, may benefit from and/or may require a particular capsulotomy shape and opening smoothness.

Figure 8:
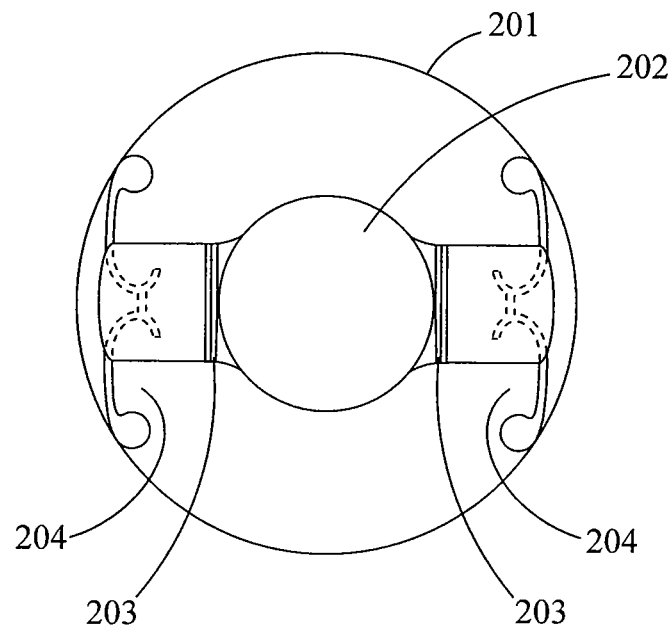
FIG. 8 is a diagram of an accommodating IOL.
Figure 9:
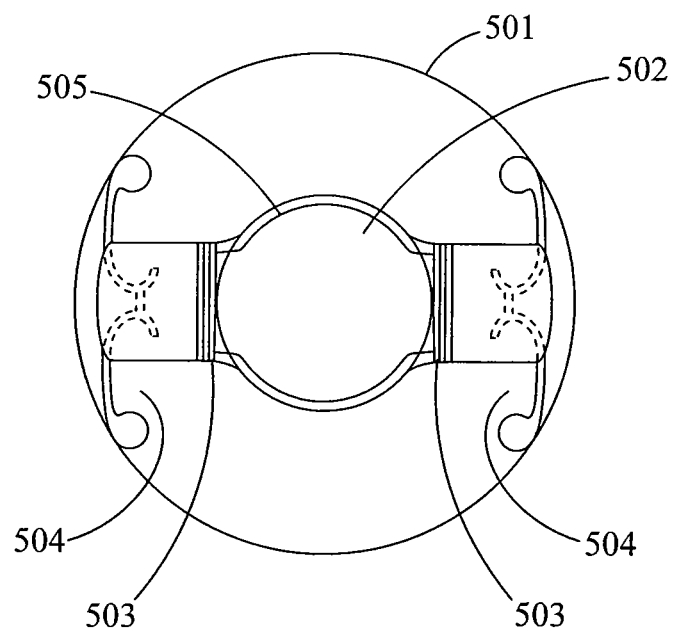
FIG. 9 is a diagram showing a shot pattern positioned on the lens of the eye in relation to the accommodating IOL of FIG. 8.
Figure 10A:
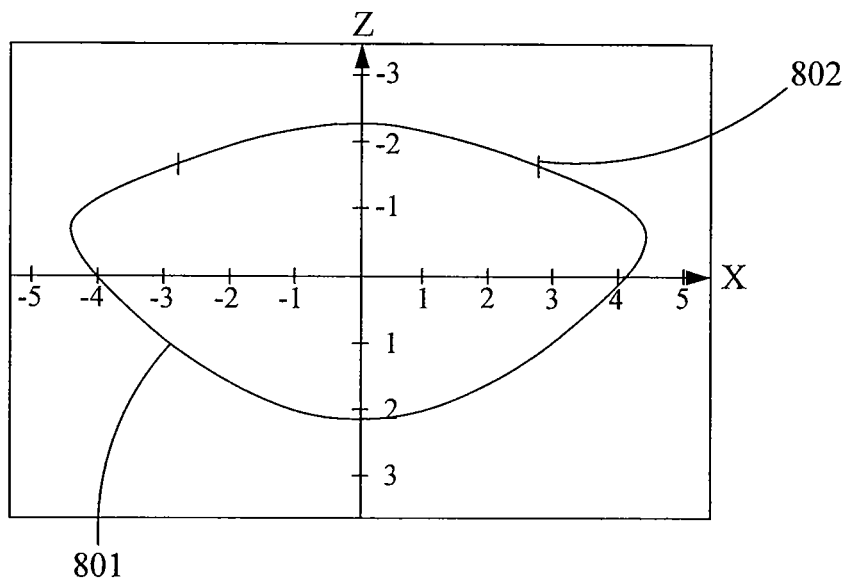
FIGS. 10 A-D are diagrams illustrating a band cut circular capsulotomy.
Figure 10B:
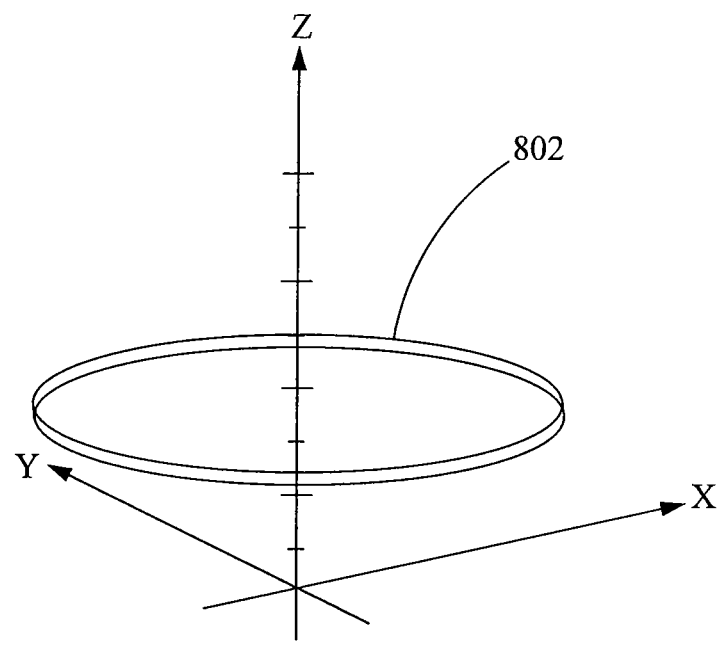
Figure 10C:
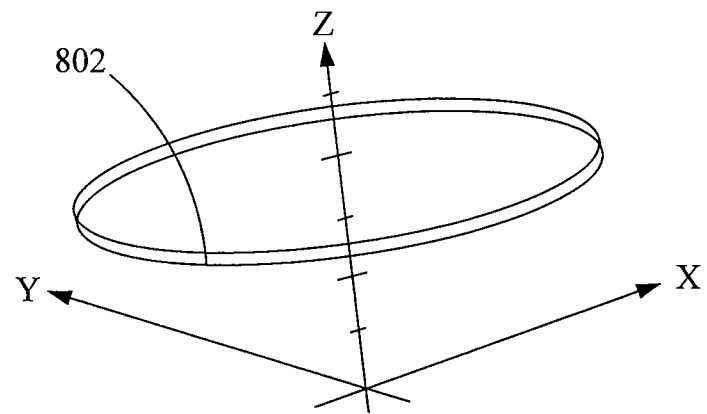
Figure 10D:
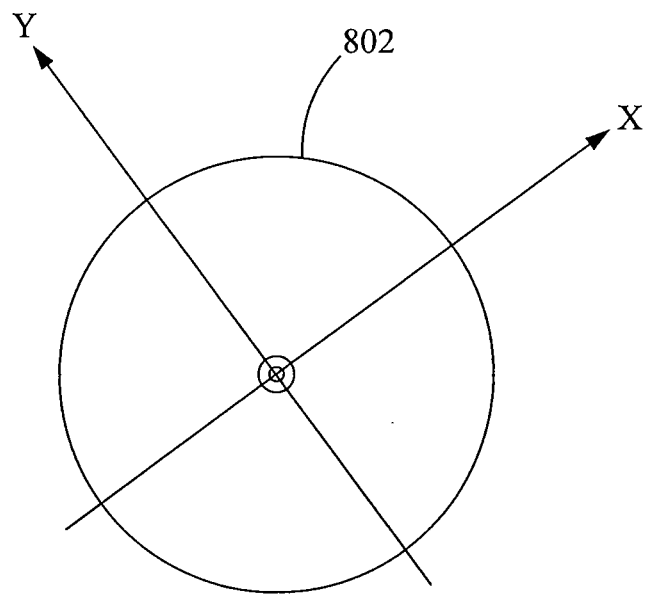

FIG. 9 illustrates a precise predetermined non-geometric cut that can be created by implementing the predetermined shot pattern in relation to the type of IOL shown in FIG. 8. Thus, there is provided an IOL lens structure 502, hinges 503 located adjacent to the lens structure 502, and haptics 504, which contact the lens capsule 501. There is further provided a precise predetermined non-geometric capsulotomy 505, having two non-linear, i.e., curved sections and two essentially linear, i.e., straight sections. The positioning of these sections is further illustrated in FIG. 9, with the essentially straight sections being positioned inside of the hinges, i.e., so that the remaining lens capsule covers at least in part the haptics, and with the curved section being inside of the lens structure 502, i.e. the remaining lens capsule covers the outer edge of the lens structure 502. This type of capsulotomy is referred to as an ALL-ON. This cut and pattern would be an example of a cut, opening, capsulotomy and pattern that essentially follow the shape of an IOL.

The order in which these activities are performed may depend upon the particular characteristics of the internal lens structure, the density of the cataract, the position of the cataract, the type of device used to remove the internal lens material once it has been sectioned into small volumes, the type and power of the laser used, the amount and size of gas bubbles that are produced by the laser, and other factors. Thus, although the examples herein provide for an order of performing the activity of cutting the anterior surface of the lens and sectioning the interior structures of the lens, it should be recognized that this order can be changed, as well as, performed essentially simultaneously or simultaneously.

The preferred laser system for treating patients is capable of making precise and predetermined cuts in the capsule of the lens thus giving rise to capsulotomies that are of precise and predetermined shapes. Thus, there is provided the method of obtaining and analyzing the shape and structure of an IOL, and in particular obtaining and analyzing the shape and structure of an accommodating IOL, an IOL that reduces and/or eliminates the need for spectacles, and/or an IOL for near, intermediate and distance vision, including but limited to FDA approved versions of said IOLs. Based upon this analysis an optimized shape and position for the capsulotomy for use with a particular IOL, or grouping of similarly shaped IOLs, is determined. A predetermined shot pattern for making this optimized shaped capsulotomy is then provided to the laser system, preferably by providing the shot pattern to the control system 103. The laser system can then be used for an one or all of the following procedures, determining the shape and position of the anterior surface of the lens, and in particular the anterior surface of the lens capsule, determining the apex of the lens capsule in relation to the laser system, performing a laser capsulotomy having the precise and predetermined shape selected for a particular type of IOL, and removal of the natural lens material.

Thus, there is provided techniques, systems and apparatus to deliver a laser beam in a shot pattern to the lens of the eye and in particular to the capsule of the lens of the eye in a precise and predetermined manner to provided for a precise predetermined capsulotomy. The shape of these patterns may be delivered using either the jigsaw or ring delivery sequences.

When performing laser assisted cataract surgery the process of cutting the nucleus with a photodisruption laser can cause a buildup of gas bubbles sufficiently near the soft cortex to allow the gas bubbles to propagate toward the capsule. In those situations where bubbles collect in close proximity to the anterior capsule, when the laser attempts to cut the capsulotomy, the sudden release of bubbles my change the position of the anterior capsule during the delivery of the laser shot pattern causing the laser to miss the capsule resulting in missed cuts, at least partially around the circumference of the capsulotomy. To solve this problem, there is provided herein a special cutting pattern that is less dependent of capsule position versus time and provides cutting of the capsule despite position changes of the capsule during the laser capsulotomy procedure. Thus, resulting in substantially reduced or no missed cuts.

There is further provided herein the use of laser shot patterns having a large range of Z swept at a high rate of speed, while the X-Y position is moved in a circular, or elliptical or other pattern or desired shape, more slowly so that the laser cutting action occurs multiple times over essentially the same X-Y position. Thus, it could be envisioned that the laser beam is operating like the tip of a jigsaw blade moving up and down rapidly compared to the X-Y positioning to create the cut shape. In this way, if the anterior capsule shifts during the cut, due to gas bubble propagation or any other reason, the cut will still be made to the capsule, albeit perhaps outside the center region of the z direction up-down distribution of shots, and more to the anterior or posterior ends of that distribution. For laser cutting of the nucleus where a great deal of bubble buildup is created, a Z range, or up-down range of the cut should be approximately 1 mm in extent, nominally centered on the anterior capsule which would allow approximately +/−475 µm of capsule movement and still provide cutting of a 25 µm thick capsule.

In addition to enabling cutting of a capsule that moves during the procedure, this procedure can be used to compensate for static errors in capsule position due to for example measurement errors. In this way the extent of the Z range may be increased by the known error of the system.

In addition to the large Z range sweeps disclosed herein, there is also contemplated the use of a smaller Z range of cut motion for the case where the uncertainty in capsule position from both static measurement error and anticipated change in position might be smaller, perhaps in the range of hundreds of µm or in the case of highly precise measurement data and near zero movement of the capsule during surgery. In such a case the Z range could be tens of µm—enough range to cut through the capsule thickness.

The Z range sweep in the capsulotomy shot pattern provides for the ability to optimize laser surgery efficiency in cataract removal procedures. Thus, the nucleus of the lens can be sectioned into small volumes before the capsulotomy is performed. In this way any gas bubbles that are formed by the sectioning of the nucleus will be trapped within the capsule. By keeping the gas bubbles inside of the capsule, their effect on laser delivery is reduced, when compared to their effect if they escape from the capsule and migrate into the aqueous or collect and build up next to the posterior of the cornea. The detrimental effect of shooting the laser beam through a bubble increases as the distance that the beam has to travel after passing through the bubble before reaching its intended point increases. Thus, by trapping the bubble in the capsule this distance is keep to an absolute minimum and thus the detrimental effect of shooting through the bubbles is similarly minimized.

The accumulation of bubbles within the capsule, however, increases the likelihood that the lens and/or capsule will shift during the capsulotomy as the bubbles escape through the cuts in the lens capsule. As noted above this shifting could result in missed cuts and an incomplete capsulotomy. Thus, the Z range sweep avoids any missed cuts from lens or capsule movement and accordingly provides the synergistic advantages of increased laser efficiency, reduced detrimental effect of gas bubbles, and reduced missed cuts in the capsulotomy.

Thus there is provided a system and method to optimize laser surgery efficiency in an embodiment of the invention by allowing the nucleus to be cut first, and the gas bubbles formed from such cutting contained within the capsule, until the capsulotomy is performed. The containing of the gas bubbles within the capsule avoids having to shoot through bubbles in the anterior chamber caused but creating the capsulotomy first. This solution, however, can lead to the accumulation of bubbles inside the fibrous mass of the lens which may cause the capsule to move during capsulotomy. To address this potential movement the invention further provides for the varying z direction movement of the laser beam. However, it is also understood that, one case where the uncertainty of capsule movement is small is the case where the capsulotomy is laser cut prior to the cutting of the nucleus material and no bubbles have been placed in the lens. In this case if the uncertainty in position is sufficiently small that the extent of the z range is sufficiently small, so that only a superficial amount of bubbles may be present in the anterior chamber which may not interfere with laser cutting of the nucleus. It should further be understood that when referring to a sequence of cutting structures, such as described in this paragraph, that the sequence is meet when a substantial majority of the cuts are performed in the one structure before another structure, i.e., the placement of a few laser shots in an other structures during delivery of the shot pattern to the first structure will not prevent the first structure from being considered the first structure in the sequence.

Further methods and systems to define a high accuracy position measurement of structures of the eye and in particular the anterior capsule, so as to provide in general greater accuracy, precisions and reproducibility from patient to patient for procedures on the eye and in particular capsulotomies, is provided in application Ser. No. 12/509,412 (Method and System for Removal and Replacement of Lens Material from the Lens of an Eye) filed on Jul. 24, 2009 and the entire disclosure of which is incorporated herein by reference.

A further optimization of the method and system to enhance flexibility regarding the aspiration of lens material from the lens capsule is provided. In sectioning the lens material it is possible that some of the cut fragments of the fibrous mass may escape the capsular bag, either by floating or because of gas bubbles or just naturally, unless means of preventing such escape are provided. Therefore another aspect of the present method and system is to provide a means to restrain these fragments until they are ready to be aspirated out. Such a means is provided by performing only a partial cut of the capsule, leaving the capsule flap attached to serve as a restraint, preventing and/or reducing the escape of sectioned lens material. Once aspiration is called for the partial cut to the capsule can be completed, i.e., the capsulotomy is completed, and the sectioned lens material aspirated out of the lens capsule.

In the laser shot patterns provided herein it is preferred that the laser shot patterns generally follow the shape of the lens and placement of individual shots with respect to adjacent shots in the pattern are sufficiently close enough to each other, such that when the pattern is complete a sufficiently continuous layer and/or line and/or volume of lens material has been removed. Shot spacing of lesser or greater distances are contemplated herein and including overlap as necessary to obtain the desired results. Shot spacing considerations include gas bubble dissipation, volume removal efficiency, sequencing efficiency, scanner performance, and cleaving efficiency among others. For example, by way of illustration, for a 5 μm size spot with an energy sufficient to cause photodisruption, a spacing of 20 μm or greater results in individual gas bubbles, which are not coalesced and dissipate more quickly, than with close shot spaces with the same energy, which result in gas bubble coalescence. As the shot spacing gets closer together volume efficiency increases. As shot spacing gets closer together bubble coalescence also increases. Further, there comes a point where the shot spacing becomes so close that volume efficiency dramatically decreases. For example, by way of illustration, for a 450 femtosecond pulse width and 2 microjoules energy and about a 5 μm spot size with a 10 μm separation results in cleaving of transparent ocular tissue. As used herein, the term cleaving means to substantially separate the tissue. Moreover, the forgoing shot spacing considerations are interrelated to a lesser or greater extent and one of skill in the art will know how to evaluate these conditions based upon the teachings of the present disclosure to accomplish the objectives herein. Finally, it is contemplated that the placement of individual shots with respect to adjacent shots in the pattern may in general be such that they are as close as possible, typically limited by the size and time frame of photodisruption physics, which would include among other things gas bubble expansion of the previous shot. As used herein, the time frame of photodisruptive physics referrers to the effects that take place surrounding photodisruption, such as plasma formation and expansion, shock wave propagation, and gas bubble expansion and contraction. Thus, the timing of sequential pulses such that they are timed faster than some of, elements of, or all of those effects, can increase volumetric removal and/or cleaving efficiency. Accordingly, we propose using pulse repetition frequencies from 50 MHz to 5 GHz, which could be accomplished by a laser with the following parameters: a mode lock laser of cavity length from 3 meters to 3 cm. Such high PRF lasers can more easily produce multiple pulses overlapping a location allowing for a lower energy per pulse to achieve photodisruption.

The terms first, second, third, etc. as used herein are relative terms and must be viewed in the context in which they are used. They do not relate to timing, unless specifically referred to as such. Thus, a first cut may be made after a second cut. In general, it is preferred to fire laser shots in general from posterior points in the laser pattern to anterior points, to avoid and/or minimize the effect of the gas bubbles resulting from prior laser shots. However, because of the varied laser shot patterns that are provided herein, it is not a requirement that a strict posterior to anterior shot sequence be followed. Moreover, in the case of cataracts it may be advantageous to shoot from anterior to posterior, because of the inability of the laser to penetrate substantially beyond the cataract.

Figure 11:
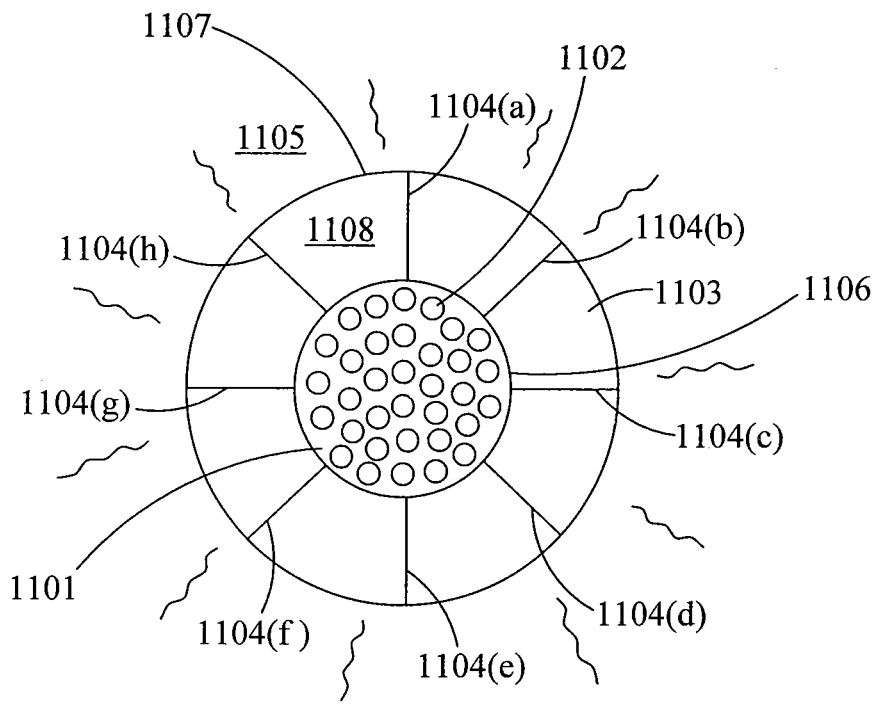
FIGS. 11 and 12 are illustrations of shot patterns utilizing radial and spherical patterns and combinations thereof.

In FIG. 11 there is shown the lens 1108 as seen as if looking through the pupil edge 1107 of the iris 1105. In this figure there is provided two regions of shots and/or cuts. There is provided a central region 1101 having a high cut density pattern, for example of small spheres, e.g., 1102, of 0.25 to 0.75 mm in diameter. This figure also has an outer region 1103 with radial cuts 1104(a)-1104(h). These cuts act as a pre-cut to the lens material in the vicinity of the iris 1105. In this way the pre-cut radials may tend to propagate out to the equator with some external applied force. This external force may be a mechanical manipulator or hand held instrument or it may be through the insertion of BSS or other safe liquid to cause the pre-cuts to propagate out to the equator.

Figure 12:
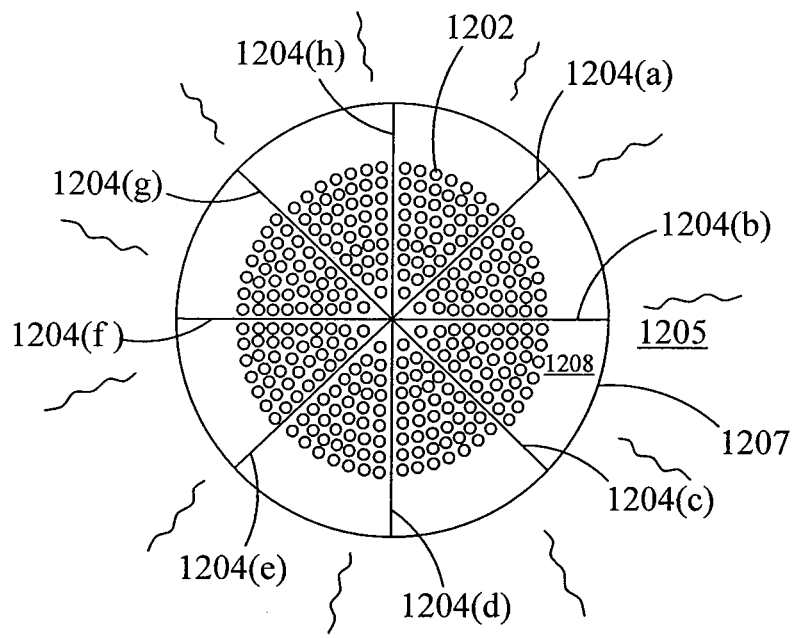

In FIG. 12 there is shown the lens 1208 as seen as if looking through the pupil edge 1207 of the iris 1205. In this figure there is shown a similar pattern to FIG. 11, except the radial cuts 1204(a)-1204(h) extend through the center of the lens and are done first by the laser to assure the cutting attributes are not interfered with by any high density cuts for example spheres, e.g., 1202. It is presently preferred and believed to be advantageous to assure that the radial cuts are complete and then to make the smaller cuts like spheres in between the radial cuts. The net effect of either the patterns of 11 or 12 is to have a control region where aspiration can more easily be accomplished as a peripheral region where radial cuts may have the opportunity to be extended to the equator by the application of external force.

Figure 13A:
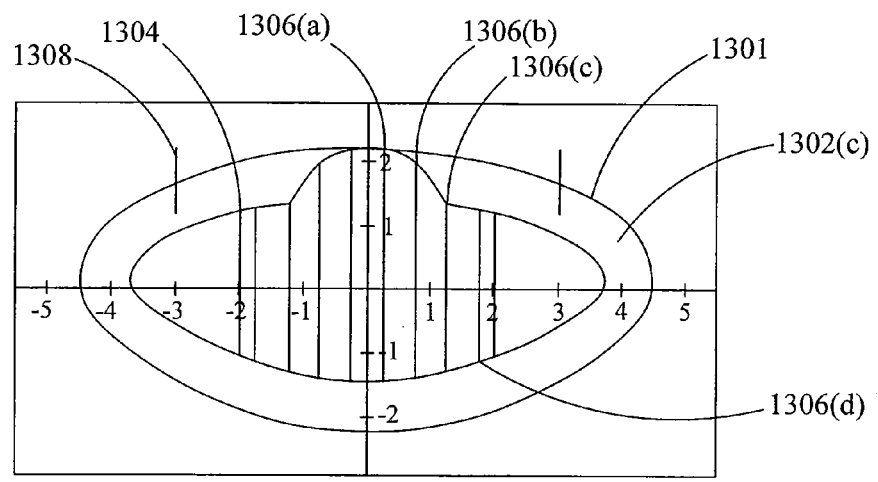
FIGS. 13A-C are diagrams illustrating laser shot patterns.
Figure 13B:
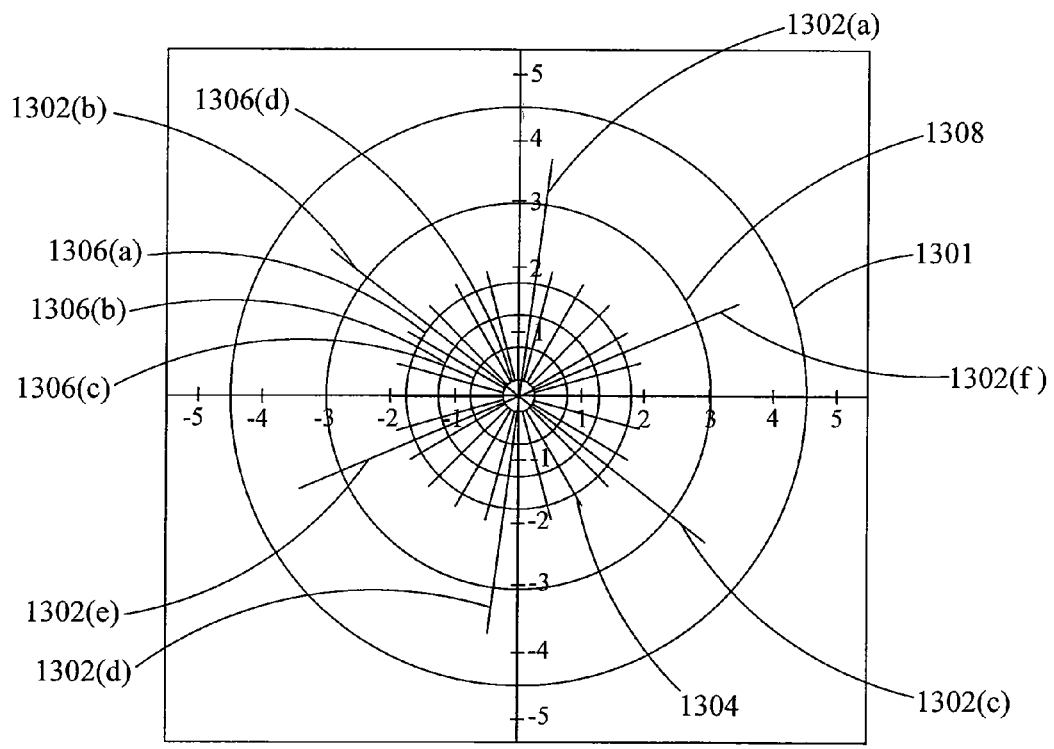
Figure 13C:
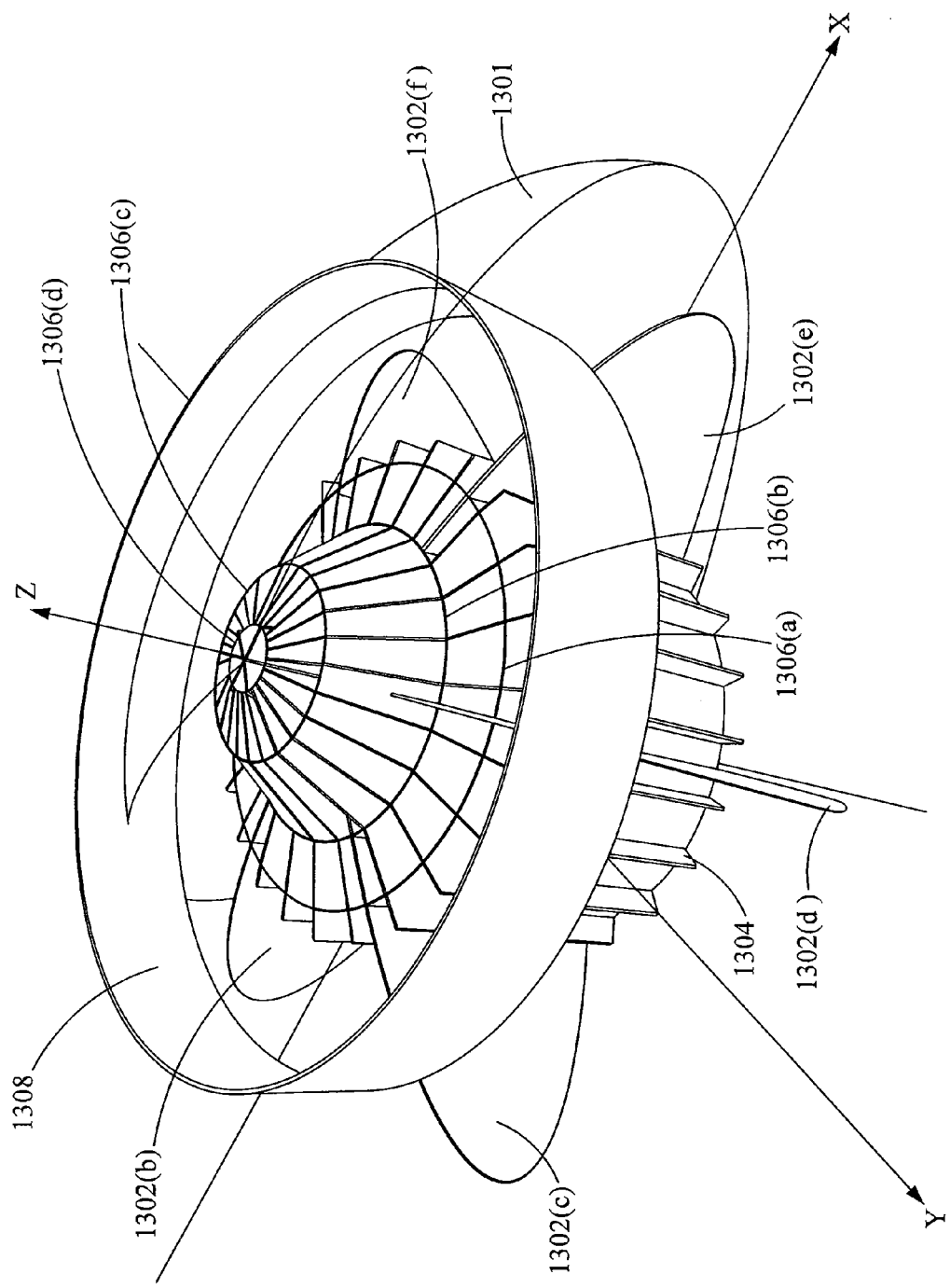

In FIGS. 13A and 13B there are shown a side cross-section and a top cross section of a lens, respectively, having the same laser shot pattern. FIG. 13C provides a prospective, relief, view of the same lens and shot pattern. Thus, there is shown the lens capsule 1301. There is shown a series of elliptical radial cuts 1302(a) to 1302(f), a series of other differently shaped radial cuts 1304 (only one of these cuts has been numbered for clarity). These radial cuts to a certain extent can be envisioned as is cuts made in slicing a pie. There is further shown a series of cylindrical cuts 1306(a) to 1306(d). There is shown a capsulotomy cut 1308.

Figure 14A:
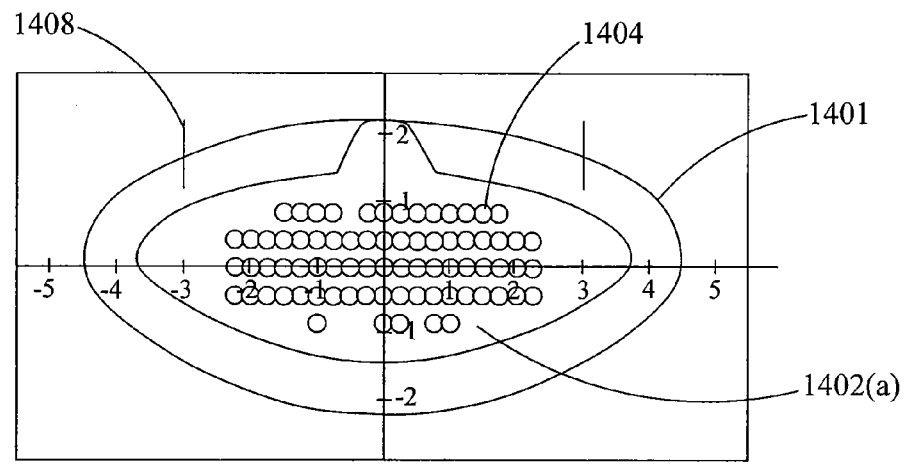
FIGS. 14A-C are diagrams illustrating laser shot patterns.
Figure 14B:
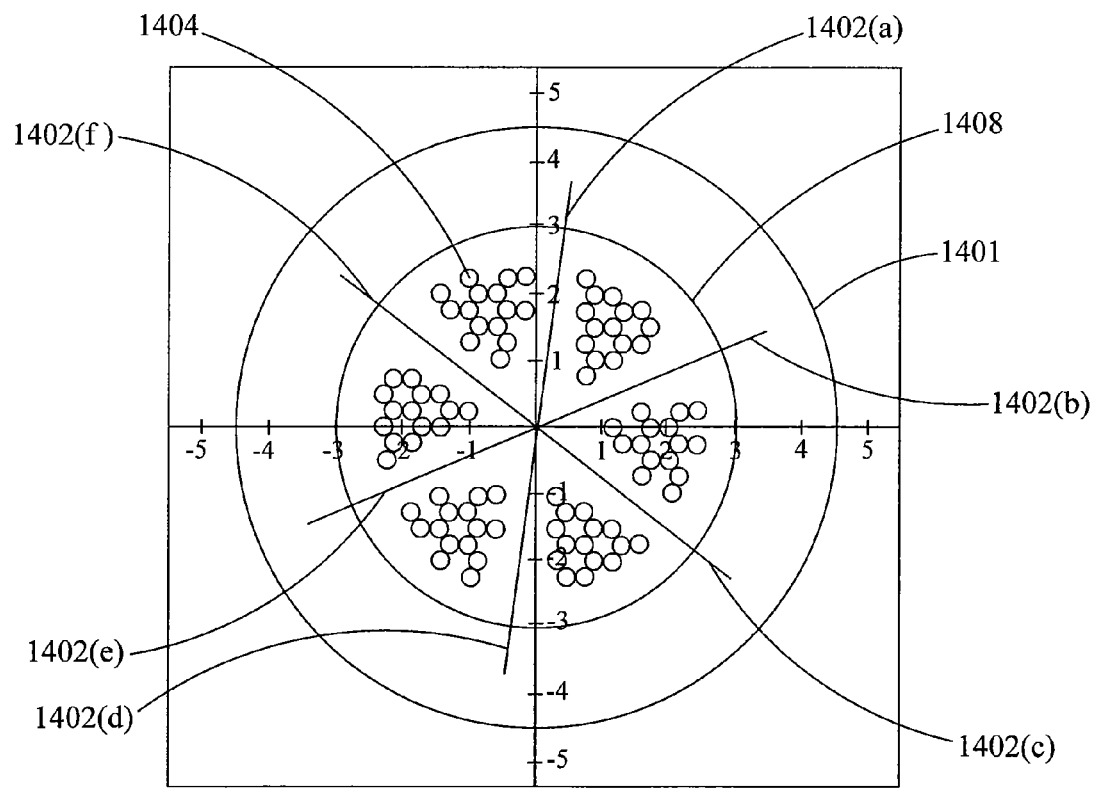
Figure 14C:
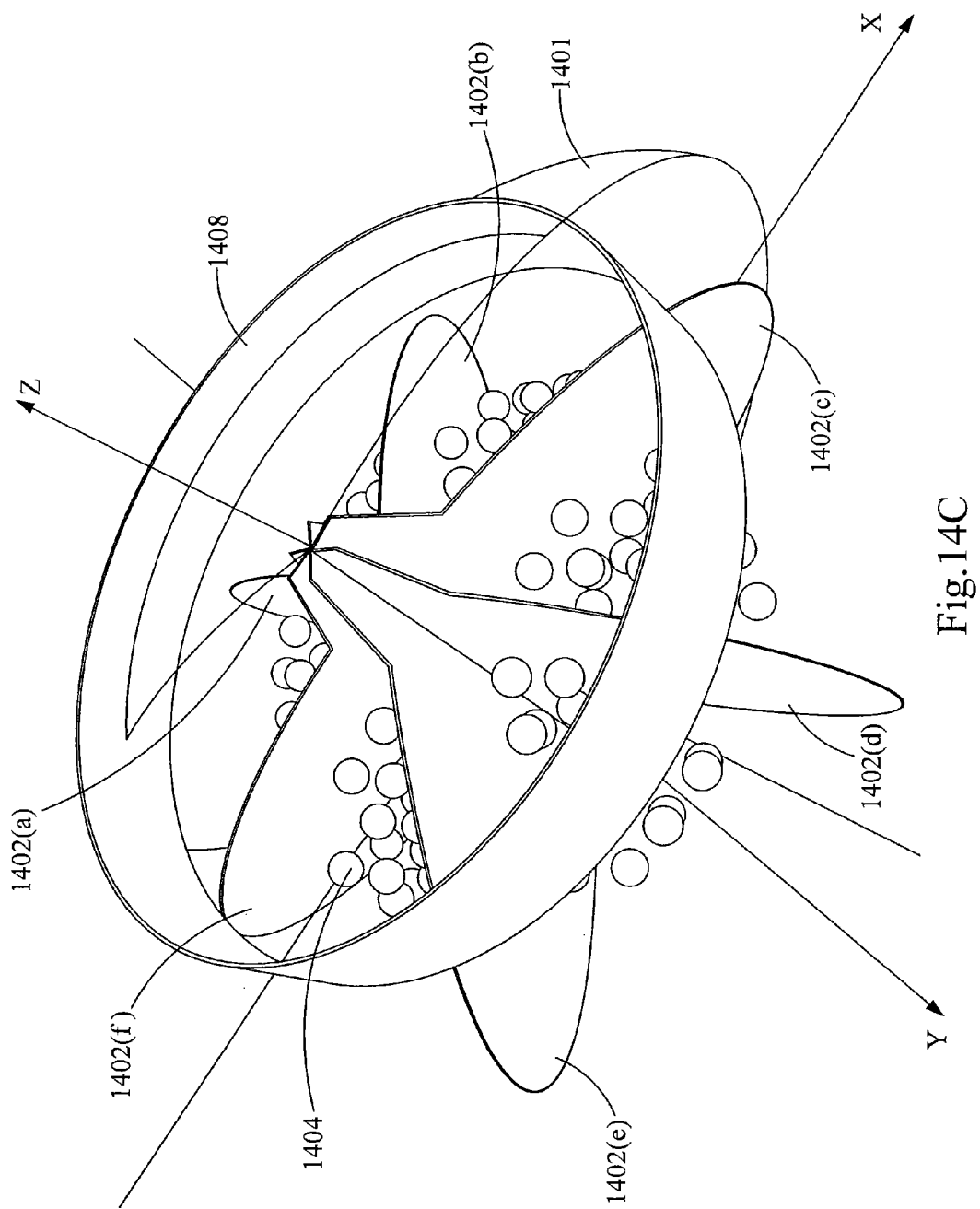

In FIGS. 14A and 14B there are shown a side cross-section and a top cross section of a lens, respectively, having the same laser shot pattern. FIG. 14C provides a prospective, relief, view of the same lens and shot pattern. Thus, there is shown the lens capsule 1401. There is shown a series of elliptical radial cuts 1402(a) to 1402(f), a series of spherical cuts 1404 (only one of these cuts has been numbered for clarity). There is shown a capsulotomy cut 1408.

Figure 15A:
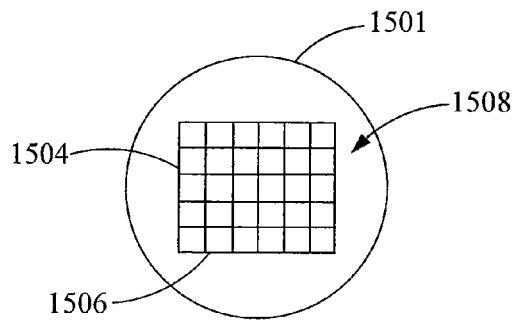
FIGS. 15A and B are diagrams illustrating laser shot patterns.
Figure 15B:
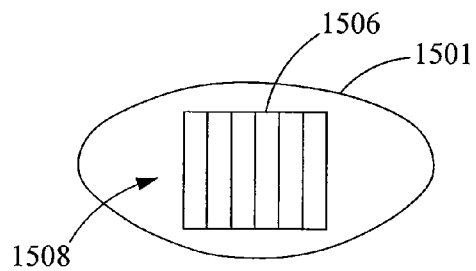

In FIGS. 15A and 15B there are shown a top cross section and a side cross-section of a lens, respectively, having the same laser shot pattern 1508. There is shown the lens capsule 1501. There is shown a laser shot pattern or cut pattern 1508 having a grid pattern of vertical 1504 and horizontal 1506 cuts (as viewed in the drawing of the figure). This shot pattern results in the lens being sectioned into a series of elongated rectangular rods. The shape of these rods can be sized to match, or be slightly smaller than the size of the opening of the aspiration tube used to remove the sectioned lens material. Thus, the size of the rectangles in the grid pattern is based upon the opening size of the aspiration tube, which presently ranges from about 0.4 mm to 1 mm. The ability to match the size of the rectangles in the grid pattern, and thus the size of the rectangular sections of lens material created by delivery of the shot pattern to the lens, to the size of the opening in the aspiration tube enhances the ability to safely and efficiently extract the lens material during lens replacement procedures.

Figure 16A:
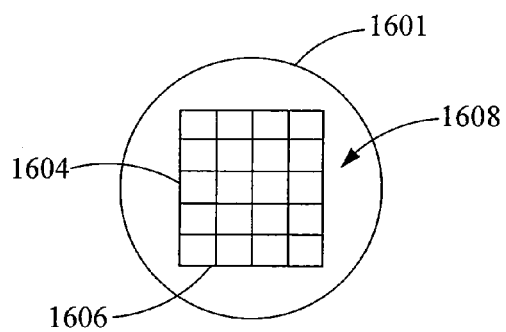
FIGS. 16A and B are diagrams illustrating laser shot patterns.
Figure 16B:
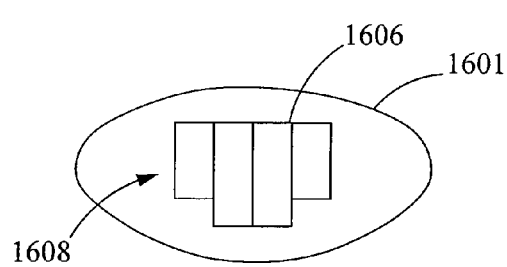

In FIGS. 16A and 16B there are shown a top cross section and a side cross-section of a lens, respectively, having the same laser shot pattern 1608. There is shown the lens capsule 1601. There is shown a laser shot pattern or cut pattern 1608 having a grid pattern of vertical 1604 and horizontal 1606 cuts (as viewed in the drawing of the figure). This shot pattern results in the lens being sectioned into a series of elongated rectangular rods. The shape of these rods can be sized to match, or be slightly smaller than the size of the opening of the aspiration tube used to remove the sectioned lens material. Thus, the size of the rectangles in the grid pattern is based upon the opening size of the aspiration tube, which presently ranges from about 0.4 mm to 1 mm. The ability to match the size of the rectangles in the grid pattern, and thus the size of the rectangular sections of lens material created by delivery of the shot pattern to the lens, to the size of the opening in the aspiration tube enhances the ability to safely and efficiently extract the lens material during lens replacement procedures. In this figure there is further shown that the shape of the sectioned materials follow the shape of the anterior capsule of the lens.

Figure 17A:
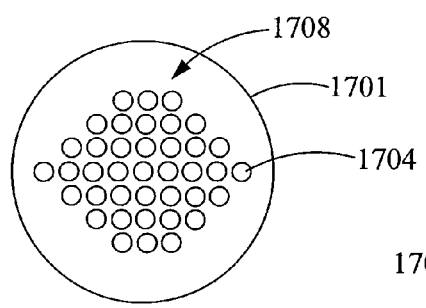
FIGS. 17A and B are diagrams illustrating laser shot patterns.
Figure 17B:
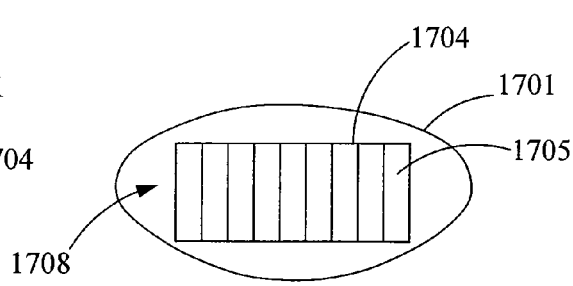

In FIGS. 17A and 17B there are shown a top cross section and a side cross-section of a lens, respectively, having the same laser shot pattern 1708. There is shown the lens capsule 1701. There is shown a laser shot pattern or cut pattern 1708 having a grid like pattern of circular 1704 cuts that form a series of tube like shapes 1705. This shot pattern results in the lens being sectioned into a series of elongated tubular rods. The shape of these rods can be sized to match, or be slightly smaller than the size of the opening of the aspiration tube used to remove the sectioned lens material. Thus, the size of the rectangles in the grid pattern is based upon the opening size of the aspiration tube, which presently ranges from about 0.4 mm to 1 mm. The ability to match the size of the rectangles in the grid pattern, and thus the size of the rectangular sections of lens material created by delivery of the shot pattern to the lens, to the size of the opening in the aspiration tube enhances the ability to safely and efficiently extract the lens material during lens replacement procedures. In this figure there is further shown that the shape of the sectioned materials follow the shape of the anterior capsule of the lens.

From the foregoing description, one skilled in the art can readily ascertain the essential characteristics of this invention, and without departing from the spirit and scope thereof, can make various changes and/or modifications of the invention to adapt it to various usages and conditions.

Accordingly, the invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing description.

What is claimed:

1. A method for providing laser shot patterns to the natural human lens of an eye for softening natural human lens material, the method comprising:
   a. providing a laser shot pattern, based-in-part on a density of a natural human lens, for changing the hardness of the natural human lens material, the shot pattern comprising a first pattern a second pattern, and a third pattern;
   b. the first pattern of the laser shot pattern having a different shot density from the second pattern of the laser shot pattern;
   c. delivering the first pattern to a first location of the natural human lens, the second pattern to a second location of the natural human lens, and the third pattern to a third location of the natural human lens, and wherein each location is a different location in the natural human lens; and
   e. wherein the first pattern creates a cut in the natural human lens material, and wherein the second and third shot patterns soften the natural human lens material at the second and third locations of the natural human lens.

2. The method of claim 1 wherein the cut is a planar cut.

3. The method of claim 2 wherein the cut is a plurality of radial planar cuts.

4. The method of claim 1 wherein the cut is an elliptical radial cut.

5. The method of claim 4 wherein the second pattern has a shot density and the third pattern has a shot density, and wherein the shot densities are essentially the same.

6. The method of claim 4 wherein the second pattern has a shot density and the third pattern has a shot density, and wherein the shot densities are different.

7. The method claim 1 wherein the second pattern has a shot density and the third pattern has a shot density, and wherein the shot densities are different.

8. The method of claim 1 wherein the second pattern has a shot density and the third pattern has a shot density, and wherein the shot densities are essentially the same.

9. The method of claim 1, wherein
   the first, the second or both shot patterns comprising a grid-like pattern for providing a multiplicity of substantially rectangular rods in a natural human lens of an eye, wherein the grid-like pattern consists essentially of consecutive rows containing an odd number of substantially rectangular rods.

10. The method of claim 9, wherein the first, the second or both shot patterns comprises a pattern for providing at least 5 substantially independent rods.

11. A method for differentially softening a natural human lens of an eye to assist in the removal and replacement of the natural human lens, the method comprising:
   a. determining a position in a natural human lens of an eye;
   b. delivering a laser shot pattern to the determined position of the natural human lens of an eye for changing the density of the natural human lens material, the pattern comprising a first area, a second area and a third area, wherein at least one of the areas is based-in-part on the determined position of the natural human lens;
   c. each of the first, second and third areas consisting essentially of a plurality of laser shots;
   d. at least two of the first, second and third areas having different densities of laser shots; and,
   e. thereby creating locations of differentially softened lens material, the locations of differentially softened lens material corresponding to at least two of the first, second and third laser shot pattern areas.

12. The method of claim 11 wherein the method comprises delivering a laser shot pattern for performing a capsulotomy.

13. The method of claim 11 wherein at least one of the first, second and third areas is shaped substantially similarly to a shape of an aspiration tube.

14. The method of claim 11 wherein a shape of the first area is based upon an aspiration tube.

15. The method of claim 11, wherein the first laser shot pattern area comprises a plurality of laser shots to create a plurality of radial cuts; and wherein the second shot pattern area comprises a plurality of laser shots to create a cylindrical cut.

16. A method for providing laser shot patterns to a natural human lens of an eye for differentially softening a natural human lens material, the method comprising:
   providing a therapeutic laser for producing a laser beam;
   delivering a laser shot pattern for sectioning a natural human lens material, the shot pattern comprising laser shots in an elliptical radial cut pattern;

whereby an elliptical radial cut is made in the natural human lens;

wherein the shot pattern comprises a grid-like pattern for providing a multiplicity of substantially cylindrical tubular rods defining a diameter in a natural human lens of the eye, and wherein the diameter of the substantially cylindrical tubal rods is a most a size of an opening of an aspiration tube used to remove material from the natural human lens; and wherein the grid-like pattern comprises consecutive rows containing an odd number of substantially cylindrical tubular rods.

17. The method of claim 16, wherein adjoining rows of the consecutive rows have different numbers of substantially cylindrical tubular rods.

18. The method of claim 16, comprising removing material from the substantially cylindrical tubular rods.

19. The method of claim 16 wherein elliptical radial cut pattern comprises a plurality of elliptical radial cuts having a common axis and wherein a second laser shot pattern is delivered to the natural human crystalline lens material, whereby the second shot pattern softens the natural human lens material.

20. A method for providing a laser beam shot pattern to an eye for safer and easier initial aspiration of lens material from the eye, the method comprising:
   a. providing a laser for providing a laser beam, the laser having a controller, the controller having associated with it a shot pattern;
   b. the controller having information about a structure of a natural human lens;
   c. the shot pattern comprising a pattern for changing a density of a first area and a second area of the natural human lens based-in-part on the information about the structure of the natural human lens;
   d. delivering the shot pattern to a lens of an eye thereby changing density of the first area and the second areas; wherein the density of the first area is different from the density of the second area and wherein the first area has a shape corresponding to an aspiration needle used for removal of the natural human lens.

21. The method of claim 20 wherein in the controller has associated with it a capsulotomy shot pattern.

22. The method of claim 20, wherein
the laser shot pattern comprises a plurality of laser shots to create a plurality of radial cuts.

23. A method for providing a laser beam shot pattern to a natural human lens of an eye, the method comprising:
   a. providing a laser for providing a laser beam;
   b. the laser having a controller having associated with it, the controller having a shot pattern associated with it; and,
   c. the shot pattern comprising a location and sequence of laser shots for providing a multiplicity of spheres in a lens of an eye, spaced between a plurality of elliptical coaxial radial cuts.

24. A method for delivering laser shot patterns to section a natural human lens of an eye for softening and lubricating sections of the natural human lens material, the method comprising:
   providing a therapeutic laser for producing a laser beam;
   delivering a laser shot pattern for performing a capsulotomy;
   delivering a laser shot pattern for sectioning a natural human lens of the eye;
      i. the laser shot pattern consisting essentially of a plurality of spheres;
      ii. the laser shot pattern comprising a first area and a second area;
      iii. the first area of the laser shot pattern having a different shot and/or cut density from the second area of the laser shot pattern; and,
   e. the delivered laser shot pattern sectioning the natural human lens and creating lubricity between the sections in the natural human lens.

* * * * *